US012807600B2

(12) United States Patent
McLaughlin et al.

(10) Patent No.: US 12,807,600 B2
(45) Date of Patent: Nov. 24, 2026

(54) METHOD FOR PREPARING ENANTIOMERICALLY ENRICHED 2-[2-(2-CHLOROTHIAZOL-5-YL)-2-HYDROXY-ETHYL]SULFANYL-6-HYDROXY-3-METHYL-5-PHENYL-PYRIMIDIN-4-ONE BY HYDROGENATION OF THE 2-OXO DERIVATIVE IN THE PRESENCE OF A CHIRAL TRANSITION METAL CATALYST

(71) Applicant: BASF SE, Ludwigshafen (DE)

(72) Inventors: Martin John McLaughlin, Liestal (CH); Christopher Koradin, Ludwigshafen (DE); Rahul Kaduskar, Navi Mumbai (IN); Harish Shinde, Navi Mumbai (IN); Roland Goetz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 543 days.

(21) Appl. No.: 18/282,874

(22) PCT Filed: Mar. 25, 2022

(86) PCT No.: PCT/EP2022/057968
§ 371 (c)(1),
(2) Date: Sep. 19, 2023

(87) PCT Pub. No.: WO2022/200594
PCT Pub. Date: Sep. 29, 2022

(65) Prior Publication Data

US 2024/0262816 A1 Aug. 8, 2024

(30) Foreign Application Priority Data

Mar. 25, 2021 (EP) .................................... 21164908

(51) Int. Cl.
*C07D 417/12* (2006.01)
*B01J 31/18* (2006.01)

(52) U.S. Cl.
CPC .......... *C07D 417/12* (2013.01); *B01J 31/189* (2013.01)

(58) Field of Classification Search
CPC ............................ C07D 417/12; B01J 31/189
See application file for complete search history.

(56) References Cited

FOREIGN PATENT DOCUMENTS

WO WO-2007/104690 A1 9/2007
WO WO-2014/167084 A1 10/2014
WO WO-2018/177970 A1 10/2018
WO WO-2018/197541 A1 11/2018
WO WO-2018/202654 A1 11/2018
WO WO2022157316 A1 * 7/2022

OTHER PUBLICATIONS

International Application No. PCT/EP2022/057968, International Search Report and Written Opinion, mailed Jul. 18, 2022.

* cited by examiner

*Primary Examiner* — Valerie Rodriguez-Garcia
*Assistant Examiner* — Karen Cheng
(74) *Attorney, Agent, or Firm* — MARSHALL, GERSTEIN & BORUN LLP

(57) ABSTRACT

The present invention relates to a method for preparing an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula (I) by hydrogenation of 2-[2-(2-chlorothia-201-5-yl)-2-oxo-ethyl]sulfanyl-6-hydroxy-3-methyl-5-phenyl-pyrimidin-4-one (1) in the presence of a chiral transition metal catalyst.

(I)

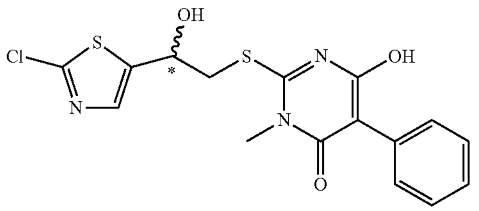

1

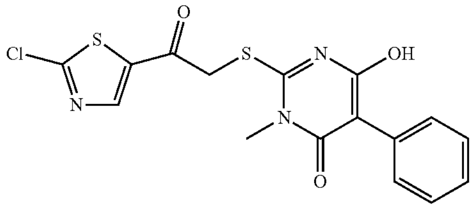

21 Claims, No Drawings

METHOD FOR PREPARING ENANTIOMERICALLY ENRICHED 2-[2-(2-CHLOROTHIAZOL-5-YL)-2-HYDROXY-ETHYL]SULFANYL-6-HYDROXY-3-METHYL-5-PHENYL-PYRIMIDIN-4-ONE BY HYDROGENATION OF THE 2-OXO DERIVATIVE IN THE PRESENCE OF A CHIRAL TRANSITION METAL CATALYST

CROSS-REFERENCE TO RELATED APPLICATIONS

This is the U.S. national phase of International Application No. PCT/EP2022/057968, filed Mar. 25, 2022, which claims the benefit of European Patent Application No. 21164908.2, filed Mar. 25, 2021.

The present invention relates to a method for preparing 2-[2-(2-chlorothiazol-5-yl)-2-hydroxy-ethyl]sulfanyl-6-hydroxy-3-methyl-5-phenyl-pyrimidin-4-one of the formula (I) as depicted below or a tautomer thereof or enantiomerically enriched forms thereof.

TECHNICAL BACKGROUND

2-[2-(2-Chlorothiazol-5-yl)-2-hydroxy-ethyl]sulfanyl-6-hydroxy-3-methyl-5-phenyl-pyrimidin-4-one (I) (or its tautomer) has been found to be a valuable intermediate in the preparation of 2,3-dihydrothiazolo[3,2-a]pyrimidinium compounds, and more specifically of 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof if 2-[2-(2-chlorothiazol-5-yl)-2-hydroxy-ethyl]sulfanyl-6-hydroxy-3-methyl-5-phenyl-pyrimidin-4-one is used in an enantiomerically enriched form. Said pyriminidium compounds have insecticidal properties and are known, for example, from WO 2018/177970 or WO 2014/167084.

The methods thus far known for the preparation of these pyriminidium compounds are cumbersome and not yet satisfactory.

In WO 2018/177970, WO 2018/197541 and WO 2018/202654, non-racemic 2,3-dihydrothiazolo[3,2-a]pyrimidinium compounds are prepared by reaction of a non-racemic 4-heteroaryl-substituted thiazolidin-2-imine with a 2-substituted malonic acid derivative. In WO 2018/177970 and WO 2018/197541, the non-racemic 4-heteroaryl-substituted thiazolidin-2-imine is in turn prepared by catalytic asymmetric hydrogenation of a 1-heteroaryl-substituted ethanimine carrying in 2-position a leaving group. The resulting amine is then reacted with an isothiocyanate to the thiazolidin-2-imine. The reaction sequence is described in WO 2018/197541 as follows:

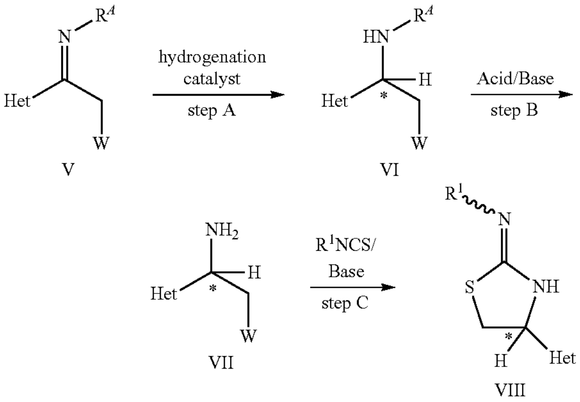

V VI VII VIII

-continued

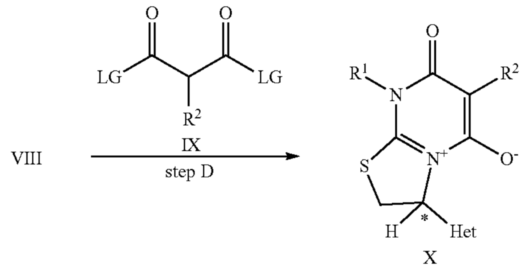

VIII IX X $R^A$ is a sulfanyl or sulfinyl, phosphoroxy, alkoxy or benzyl group; Het is optionally substituted pyridin-3-yl, thiazol-5-yl or pyrimidin-5-yl, W and LG are leaving groups, $R^1$ is a (cyclo)aliphatic group and $R^2$ is 5- or 6-membered carbo- or heterocyclic ring. In WO 2018/177970 the amine VII is obtained via another reaction path from the corresponding sulfinylimine.

WO 2018/177970 and WO 2018/202654 describe a further access to the non-racemic 4-heteroaryl-substituted thiazolidin-2-imine. This is here prepared starting from a heteroarylmethyl ketone, where the methyl group carries a leaving group, conversion of this leaving group into an alkylcarbonyloxy group, hydrolysis of the latter to a hydroxyl group, reaction of the resulting heteroarylhydroxymethyl ketone with a sulfamoyl halide to a 4-heteroaryl-5H-oxathiazole 2,2-dioxide, submission of the latter to a catalytic asymmetric hydrogenation to yield a non-racemic 4-heteroaryloxathiazolidine 2,2-dioxide and reaction thereof with an isothiocyanate to the thiazolidin-2-imine. The reaction sequence is described in WO 2018/202654 as follows:

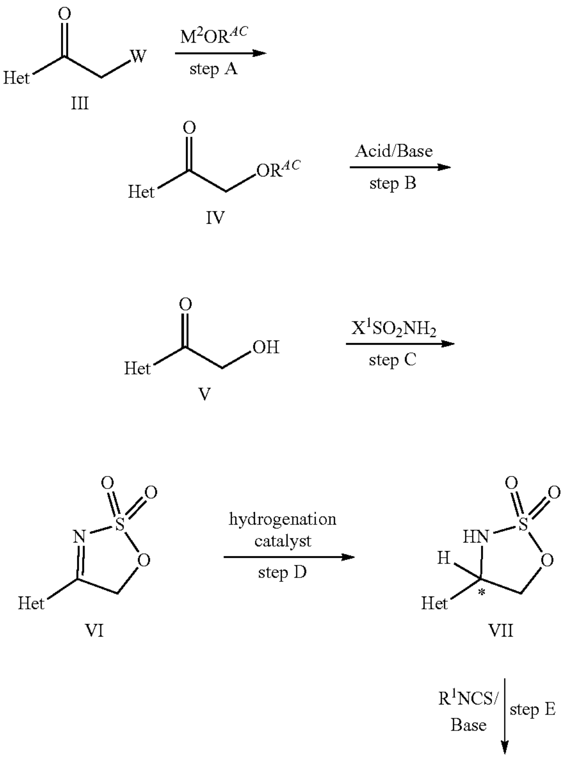

III IV V VI VII

-continued

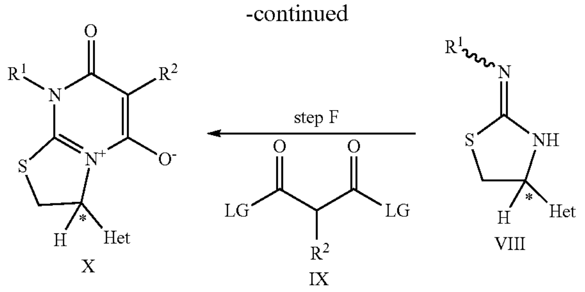

Het is optionally substituted pyridin-3-yl, thiazol-5-yl or pyrimidin-5-yl, W and LG are leaving groups, $M^2$ is Li, Na, K, Al, Ba, Cs, Ca or Mg, $R^{AC}$ is alkylcarbonyl, $X^1$ is halogen, $R^1$ is a (cyclo)aliphatic group and $R^2$ is 5- or 6-membered carbo- or heterocyclic ring.

These methods are however not very economic. Some reagents are expensive, recycling of some of the reagents which are not or not entireyl consumed is difficult, the overall yield is not satisfactory and too many reaction steps are involved.

SUMMARY OF THE INVENTION

It was the object of the present invention to provide an economic process for the preparation of 2-[2-(2-chlorothiazol-5-yl)-2-hydroxy-ethyl]sulfanyl-6-hydroxy-3-methyl-5-phenyl-pyrimidin-4-one and especially a process for the preparation of an enantiomerically enriched form thereof which yields the S or R enantiomer with high selectivity.

The problem is solved by a method for preparing an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula (I):

(I)

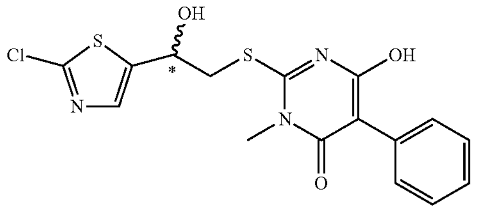

where the asterisk * shows the stereogenic center; or a tautomer thereof;

which method comprises reducing 2-[2-(2-chlorothiazol-5-yl)-2-oxo-ethyl]sulfanyl-6-hydroxy-3-methyl-5-phenyl-pyrimidin-4-one of the formula 1

1

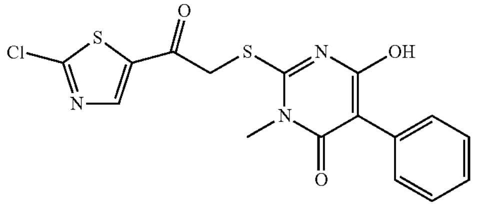

or a tautomer thereof with hydrogen in the presence of a chiral transition metal catalyst; to obtain an enantiomerically enriched form of the pyrimidinone of the formula (I) or of a tautomer thereof.

DETAILED DESCRIPTION OF THE INVENTION

Definitions

"Enantiomerically enriched form" of 2-[2-(2-chlorothiazol-5-yl)-2-hydroxy-ethyl]sulfanyl-6-hydroxy-3-methyl-5-phenyl-pyrimidin-4-one of the formula (I) or the compound (I) "in enantiomerically enriched form" and similar terms denote a non-racemic compound (I) in which either the S enantiomer or the R enantiomer predominates or is even present as only stereoisomer. The compound (I) has a single stereogenic center which is at the aliphatic carbon atom carrying the OH group and marked with an asterisk.

The organic moieties mentioned below are—like the term halogen—collective terms for individual listings of the individual group members. The prefix Cn-Cm indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy refers to saturated straight-chain (linear) or branched hydrocarbon radicals having 1 to 3 ("$C_1$-$C_3$-alkyl"), 1 to 4 ("$C_1$-$C_4$-alkyl"), 1 to 6 ("$C_1$-$C_6$-alkyl"), 3 to 4 ("$C_3$-$C_4$-alkyl") or 3 to 6 ("$C_3$-$C_6$-alkyl") carbon atoms. $C_1$-$C_3$-Alkyl denotes a saturated linear or branched aliphatic radical with 1 to 3 carbon atoms. Examples are methyl, ethyl, n-propyl or isopropyl. $C_1$-$C_4$-Alkyl denotes a saturated linear or branched aliphatic radical with 1 to 4 carbon atoms. Examples are methyl, ethyl, n-propyl, isopropyl, n-butyl, sec-butyl, isobutyl and tert-butyl. $C_1$-$C_6$-Alkyl denotes a saturated linear or branched aliphatic radical with 1 to 6 carbon atoms. Examples are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_3$-$C_4$-Alkyl denotes a saturated linear or branched aliphatic radical with 3 or 4 carbon atoms. Examples are n-propyl, isopropyl, n-butyl, sec-butyl, isobutyl and tert-butyl. $C_3$-$C_6$-Alkyl denotes a saturated linear or branched aliphatic radical with 3 to 6 carbon atoms. Examples are, in addition to those mentioned for $C_3$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_4$-haloalkyl" as used herein, which can also be expressed as "alkyl which is partially or fully halogenated", refers to straight-chain or branched alkyl groups having 1 to 4 carbon atoms (as mentioned above), where some or all of the hydrogen atoms in these groups are replaced by halogen atoms as mentioned above. Examples are chloromethyl, bromomethyl, dichloromethyl, trichloromethyl, fluoromethyl, difluoromethyl, trifluoromethyl, chlorofluoromethyl, dichlorofluoromethyl, chlorodi-fluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, hep-tafluoropropyl, 1,1,1-trifluoroprop-2-yl, 3-chloropropyl, 4-chlorobutyl and the like.

The term "$C_3$-$C_6$-cycloalkyl" as used herein refers to monocyclic saturated hydrocarbon radicals having 3 to 6 carbon atoms as (only) ring members. Examples are cyclopropyl, cyclobutyl, cyclopentyl and cyclohexyl.

The term "$C_1$-$C_4$-alkoxy" refers to a $C_1$-$C_4$-alkyl group, as defined above, attached via an oxygen atom to the remainder of the molecule. Examples are methoxy, ethoxy, n-propoxy, 1-methylethoxy (isopropoxy), n-butoxy, 1-methylpropoxy (sec-butoxy), 2-methylpropoxy (isobutoxy) or 1,1-dimethylethoxy (tert-butoxy).

If not specified otherwise, amino is $NH_2$.

$C_1$-$C_4$-Alkylamino is a group —NHR, where R is a $C_1$-$C_4$-alkyl group, as defined above.

Di-($C_1$-$C_4$-alkyl)-amino is a group —NRR', where R and R', independently of each other, are a $C_1$-$C_4$-alkyl group, as defined above.

Imino is a group containing a C═N double bond. The C═N bond can also be part of a heterocycle.

In chiral ligands which comprise just one phosphino group and additionally at least one of a phosphine oxide group, an amino group or an imino group, the amino and imino groups are nitrogen-containing groups in which the nitrogen atom can coordinate to a central metal in a complex. In this context, unlike defined above, the amino group is not limited to $NH_2$, but is a group —NRR', where R and R', independently of each other, are hydrogen or an organic radical. Moreover, the amino or imino group can also be part of a heterocyclic ring, as is for example the case in ligand L.5 (depicted below). A phosphino group in this context is a group —PRR', where R and R', independently of each other, are hydrogen or an organic radical; and a phosphine oxide group is a group —P(═O)RR', where R and R', independently of each other, are hydrogen or an organic radical.

The 5- or 6-membered heteroaromatic ring having 1, 2 or 3 heteroatoms selected from O, N and S are ring members may be attached to the remainder of the molecule via a carbon ring member or via a nitrogen ring member. As a matter of course, the heteroaromatic ring contains at least two carbon ring atoms. The heteroaromatic ring contains 1, 2 or 3 nitrogen atoms as ring members, or contains 1 oxygen atom and optionally one or two nitrogen atoms as ring members, or contains one sulfur atom and optionally one or two nitrogen atoms as ring members. Examples are 2-furyl, 3-furyl, 2-thienyl, 3-thienyl, 1-pyrrolyl, 2-pyrrolyl, 3-pyrrolyl, 1-pyrazolyl, 37-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, 1,2,5-thiadiazol-3-yl, 1,2,3-thiadiazol-4-yl, 1,2,3-thiadiazol-5-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, and the like.

If $R^3$ and $R^4$, together with the nitrogen atom to which they are bonded, form a 5- or 6-membered saturated heterocyclic ring (see below definition), the $NR_3R^4$ group is 1-pyrrolidinyl or 1-piperidinyl.

Group VIII metal catalysts refer to catalysts having a metal from group VIII of the periodic system of elements as central metal. Group VIII relates to the IUPAC group definition valid before 1985 and corresponds to groups 8, 9 and 10 of the current IUPAC group designation.

The compound (I) can be present as a tautomer thereof or as a mixture of different tautomeric forms. An example for a tautomeric form of the compound of the formula (I) as depicted above is the following formula:

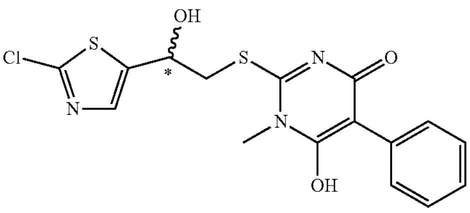 [SMILES: Cn1c(SCC(O)c2cnc(Cl)s2)nc(=O)c(-c2ccccc2)c1O]

Mixtures of different tautomeric forms are for example mixtures of this tautomer and the tautomer depicted above as formula (I).

Also compound 1 can be present as a tautomer thereof or as a mixture of different tautomeric forms. An example for a tautomeric form of the compound of the formula 1 as depicted above is the following formula:

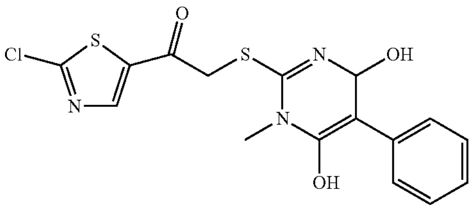 [SMILES: CN1C(SCC(=O)c2cnc(Cl)s2)=NC(O)C(c2ccccc2)=C1O]

Mixtures of different tautomeric forms are for example mixtures of this tautomer and the tautomer depicted above as formula 1.

For the sake of simplicity, in the following only compounds (I) and 1 are mentioned. Nevertheless, all embodiments also relate to their tautomers and mixtures of different tautomeric forms thereof.

Embodiments (E.x) of the Invention

General and preferred embodiments E.x are summarized in the following, non-exhaustive list. Further preferred embodiments become apparent from the paragraphs following this list.

E.1. A method for preparing an enantiomerically enriched form of 2-[2-(2-chlorothiazol-5-yl)-2-hydroxy-ethyl]sulfanyl-6-hydroxy-3-methyl-5-phenyl-pyrimidin-4-one of the formula (I):

(I)

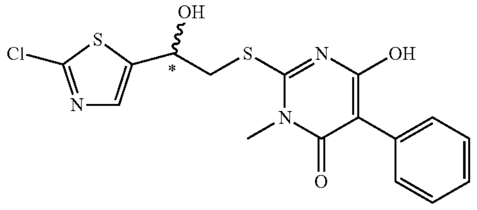

where the asterisk * shows the stereogenic center; or of a tautomer thereof;

which method comprises reducing 2-[2-(2-chlorothiazol-5-yl)-2-oxo-ethyl]sulfanyl-6-hydroxy-3-methyl-5-phenyl-pyrimidin-4-one of the formula 1

1

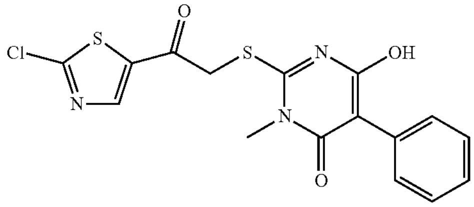

or a tautomer thereof with hydrogen in the presence of a chiral transition metal catalyst to obtain an enantiomerically enriched form of the pyrimidinone of the formula (I) or of a tautomer thereof.

E.2. The method according to embodiment 1, where the chiral transition metal catalyst is selected from group VIII metal catalysts.

E.3. The method according to embodiment 2, where the chiral transition metal catalyst is selected from group 8 or 9 metal catalysts.

E.4. The method according to embodiment 3, where the chiral transition metal catalyst is selected from Ru, Rh and Ir catalysts.

E.5. The method according to embodiment 4, where the chiral transition metal catalyst is selected from Rh and Ir catalysts.

E.6. The method according to any of the preceding embodiments, where the chiral transition metal catalyst, calculated on the basis of the transition metal content, is used in an amount of 0.01 to 10 mol %, relative to 1 mol of the compound 1.

E.7. The method according to embodiment 6, where the chiral transition metal catalyst, calculated on the basis of the transition metal content, is used in an amount of from 0.05 to 5 mol-%, relative to 1 mol of the compound 1.

E.8. The method according to embodiment 7, where the chiral transition metal catalyst, calculated on the basis of the transition metal content, is used in an amount of from 0.1 to 5 mol-%, relative to 1 mol of the compound 1.

E.9. The method according to embodiment 8, where the chiral transition metal catalyst, calculated on the basis of the transition metal content, is used in an amount of from 1 to 5 mol-%, relative to 1 mol of the compound 1.

E. 10. The method according to any of the preceding embodiments, where the chiral transition metal catalyst contains one or more chiral ligands coordinated to a transition metal.

E.11. The method according to any of the preceding embodiments, where the chiral transition metal catalyst is either preformed and contains one or more chiral ligands coordinated to a transition metal; or is formed in situ by reaction of a transition metal precursor compound and one or more chiral ligands.

E.12. The method according to any of the preceding embodiments, where the chiral transition metal catalyst comprises one or more chiral ligands coordinated to a transition metal, where the chiral ligands are chiral phosphine ligands comprising one or more phosphino groups, where in case that the chiral ligands comprise just one phosphino group, they comprise additionally at least one of a phosphine oxide group or an amino group or an imino group.

E.13. The method according to embodiment 12, where the chiral transition metal catalyst comprises one or more chiral ligands coordinated to a transition metal, where the chiral ligands are selected from the group consisting of the chiral forms of the ligands of formulae L.1 to L.15:

L.1

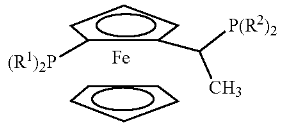

L.2

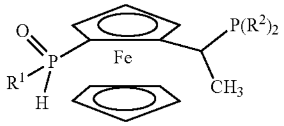

L.3

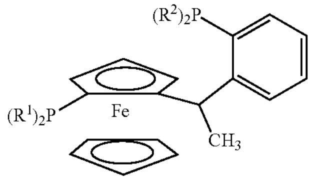

L.4

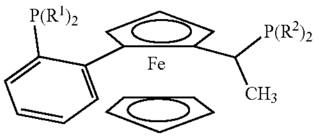

L.5

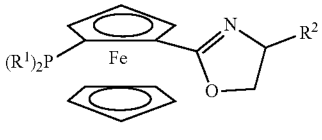

L.6

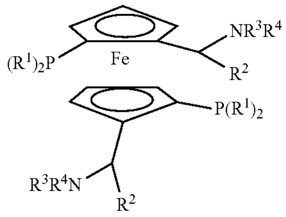

L.7

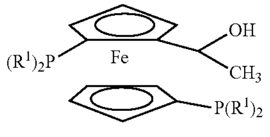

-continued

L.8

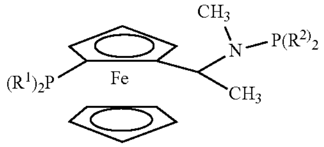

L.9

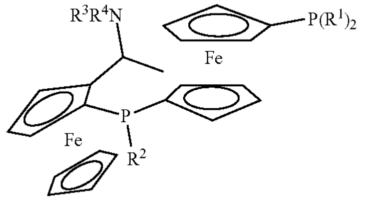

L.10

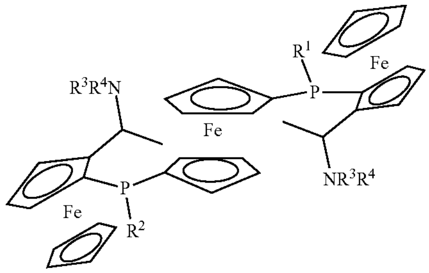

L.11

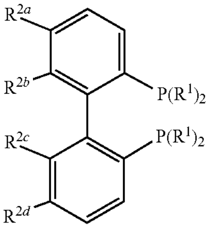

L.12

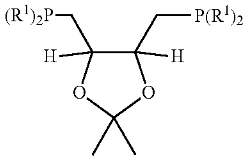

L.13

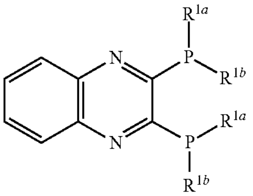

L.14.1

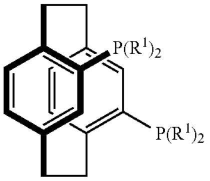

L.14.2

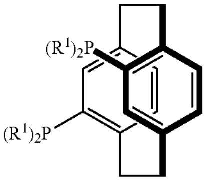

-continued

L.15

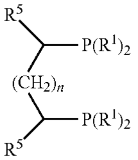

where in L.1:

$R^1$ and $R^2$, independently of each other and independently of each occurrence, are selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl;

in L.2:

$R^1$ and $R^2$, independently of each other and independently of each occurrence, are selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl;

in L.3:

$R^1$ and $R^2$, independently of each other and independently of each occurrence, are selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and $R^3$ and $R^4$ are methyl;

in L.4:

$R^1$ and $R^2$, independently of each other and independently of each occurrence, are selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

in L.5:

$R^1$ is phenyl or naphthyl, where phenyl and naphthyl may carry 1, 2 or 3 substituents selected from the group consisting of $C_1$-$C_4$-alkyl and $C_1$-$C_4$-haloalkyl; and $R^2$ is $C_1$-$C_4$-alkyl;

in L.6:

$R^1$ is selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

$R^2$ is phenyl; and $R^3$ and $R^4$, independently of each other, are $C_1$-$C_4$-alkyl;

in L.7:

$R^1$ is phenyl;

in L.8:

$R^1$ and $R^2$ are phenyl;

in L.9:

$R^1$ is $C_3$-$C_6$-cycloalkyl;

$R^2$ is phenyl; and $R^3$ and $R^4$, independently of each other, are $C_1$-$C_4$-alkyl;

in L.10:

$R^1$ and $R^2$ are phenyl; and $R^3$ and $R^4$, independently of each other, are $C_1$-$C_4$-alkyl;

in L.11:

each $R^1$ is independently selected from the group consisting of $C_1$-$C_6$-alkyl, phenyl which may carry 1, 2 or 3 substituents selected from the group consisting of $C_1$-$C_4$-alkyl, $C_1$-$C_4$-alkoxy, amino, $C_1$-$C_4$-alkylamino and di-($C_1$-$C_4$-alkyl)-amino; and a 5- or 6-membered heteroaromatic ring having 1, 2 or 3 heteroatoms selected from O, N and S are ring members;

$R^{2a}$ and $R^{2d}$ are hydrogen; and $R^{2b}$ and $R^{2c}$ are $C_1$-$C_4$-alkoxy;

or $R^{2a}$ and $R^{2b}$ form together a bridging group —CH═CH—CH═CH— or —O—$CH_2$—O—; and $R^{2c}$ and $R^{2d}$ form together a bridging group —CH═CH—CH═CH— or —O—$CH_2$—O—;

in L.12:

each $R^1$ is independently phenyl which may carry 1, 2 or 3 substituents selected from the group consisting of $C_1$-$C_4$-alkyl and $C_1$-$C_4$-alkoxy, in L.13:

each $R^{1a}$ is independently $C_1$-$C_6$-alkyl;

each $R^{1b}$ is independently $C_1$-$C_6$-alkyl;

where $R^{1a}$ and $R^{1b}$ bound on the same P atom are not identical;

in L.14.1 and L.14.2:

$R^1$ is phenyl;

in L.15:

each $R^1$ is independently phenyl which may carry 1, 2 or 3 substituents selected from the group consisting of $C_1$-$C_4$-alkyl and $C_1$-$C_4$-alkoxy;

each $R^5$ is independently H or methyl; and n is 0, 1 or 2.

E.14. The method according to embodiment 13, where:

in L.1:

the two radicals $R^1$ are identical and selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl; and the two radicals $R^2$ are identical and selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl;

in L.2:

$R^1$ is selected from the group consisting of $C_1$-$C_6$-alkyl and phenyl which may carry 1, 2 or 3 substituents selected from the group consisting of $C_1$-$C_4$-alkyl; and the two radicals $R^2$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl;

in L.3:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

the two radicals $R^2$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and $R^3$ and $R^4$ are methyl;

in L.4:

the two radicals $R^1$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

the two radicals $R^2$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

in L.5:

the two radicals $R^1$ are identical and selected from the group consisting of phenyl or naphthyl, where phenyl and naphthyl may carry 1, 2 or 3 substituents selected from the group consisting of $C_1$-$C_4$-alkyl and $C_1$-$C_4$-haloalkyl; and $R^2$ is $C_1$-$C_4$-alkyl;

in L.6:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

$R^2$ is phenyl; and $R^3$ and $R^4$ are identical and are $C_1$-$C_4$-alkyl;

in L.7:

$R^1$ is phenyl;

in L.8:

$R^1$ and $R^2$ are phenyl;

in L.9:

the two radicals $R^1$ are identical and are $C_3$-$C_6$-cycloalkyl;

$R^2$ is phenyl; and $R^3$ and $R^4$ are identical and are $C_1$-$C_4$-alkyl;

in L.10:

$R^1$ and $R^2$ are phenyl; and $R^3$ and $R^4$ are identical and are $C_1$-$C_4$-alkyl;

in L.11:

the four radicals $R^1$ are identical and selected from the group consisting of $C_1$-$C_6$-alkyl, phenyl which may carry 1, 2 or 3 substituents selected from the group consisting of $C_1$-$C_4$-alkyl, $C_1$-$C_4$-alkoxy, amino, $C_1$-$C_4$-alkylamino and di-($C_1$-$C_4$-alkyl)-amino; and a 5- or 6-membered heteroaromatic ring having 1, 2 or 3 heteroatoms selected from O, N and S are ring members;

$R^{2a}$ and $R^{2d}$ are hydrogen; and $R^{2b}$ and $R^{2c}$ are identical and are $C_1$-$C_4$-alkoxy; or $R^{2a}$ and $R^{2b}$ form together a bridging group —CH═CH—CH═CH—; and simultaneously $R^{2c}$ and $R^{2d}$ form together a bridging group —CH═CH—CH═CH—; or $R^{2a}$ and $R^{2b}$ form together a bridging group —O—$CH_2$—O—; and simultaneously $R^{2c}$ and $R^{2d}$ form together a bridging group —O—$CH_2$—O—;

in L.12:

the four radicals $R^1$ are identical and are phenyl which may carry 1, 2 or 3 substituents selected from the group consisting of $C_1$-$C_4$-alkyl and $C_1$-$C_4$-alkoxy, in L.13:

the two radicals $R^{1a}$ are identical and are $C_1$-$C_6$-alkyl;

the two radicals $R^{1b}$ are identical and are $C_1$-$C_6$-alkyl;

where $R^{1a}$ and $R^{1b}$ bound on the same P atom are not identical;

in L.14.1 and L.14.2:

$R^1$ is phenyl;

in L.15:

the four radicals $R^1$ are identical and are phenyl which may carry 1, 2 or 3 substituents selected from the group consisting of $C_1$-$C_4$-alkyl and $C_1$-$C_4$-alkoxy;

each $R^5$ is independently H or methyl; and n is 0, 1 or 2.

E. 15. The method according to embodiment 14, where:

in L.1:

the two radicals $R^1$ are identical and selected from the group consisting of $C_3$-$C_6$-alkyl, cyclohexyl, phenyl which may carry 1, 2 or 3 substituents selected from the group consisting of $C_1$-$C_4$-alkyl and $C_1$-$C_4$-haloalkyl; and naphthyl; and the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl and $C_1$-$C_4$-haloalkyl;

in L.2:

$R^1$ is selected from the group consisting of $C_3$-$C_6$-alkyl and phenyl which may carry 1, 2 or 3 substituents selected from the group consisting of $C_1$-$C_4$-alkyl; and the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl;

in L.3:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

the two radicals $R^2$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and $R^3$ and $R^4$ are methyl;

in L.4:

the two radicals $R^1$ are identical and selected from the group consisting of $C_3$-$C_6$-alkyl, cyclohexyl and phenyl;

the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl and $C_1$-$C_4$-haloalkyl;

in L.5:

the two radicals $R^1$ are identical and are naphthyl; and $R^2$ is $C_3$-$C_4$-alkyl;

in L.6:

the two radicals $R^1$ are identical and selected from the group consisting cyclohexyl and phenyl which may carry 1, 2 or 3 substituents selected from the group consisting of $C_1$-$C_4$-alkyl and $C_1$-$C_4$-alkoxy;

$R^2$ is phenyl; and $R^3$ and $R^4$ are methyl;

in L.7:

$R^1$ is phenyl;

in L.8:

$R^1$ and $R^2$ are phenyl;

in L.9:

the two radicals $R^1$ are identical and are cyclohexyl;

$R^2$ is phenyl; and $R^3$ and $R^4$ are methyl;

in L.10:

$R^1$ and $R^2$ are phenyl; and $R^3$ and $R^4$ are methyl;

in L.11:

the four radicals $R^1$ are identical and selected from the group consisting of $C_3$-$C_6$-alkyl, phenyl which may carry 1, 2 or 3 substituents selected from the group consisting of $C_3$-$C_4$-alkyl, $C_1$-$C_4$-alkoxy and di-($C_1$-$C_4$-alkyl)-amino; and furyl;

$R^{2a}$ and $R^{2d}$ are hydrogen; and $R^{2b}$ and $R^{2c}$ are identical and are $C_1$-$C_4$-alkoxy; or $R^{2a}$ and $R^{2b}$ form together a bridging group —CH═CH—CH═CH—; and simultaneously $R^{2c}$ and $R^{2d}$ form together a bridging group —CH═CH—CH═CH—; or $R^{2a}$ and $R^{2b}$ form together a bridging group —O—$CH_2$—O—; and simultaneously $R^{2c}$ and $R^{2d}$ form together a bridging group —O—$CH_2$—O—;

in L.12:

the four radicals $R^1$ are identical and are phenyl which may carry 1, 2 or 3 substituents selected from the group consisting of $C_1$-$C_4$-alkyl and $C_1$-$C_4$-alkoxy, in L.13:

the two radicals $R^{1a}$ are identical and are $C_3$-$C_6$-alkyl;

the two radicals $R^{1b}$ are identical and are $C_1$-$C_6$-alkyl;

where $R^{1a}$ and $R^{1b}$ bound on the same P atom are not identical;

in L.14.1 and L.14.2:

$R^1$ is phenyl;

in L.15:

the four radicals $R^1$ are identical and are phenyl which may carry 1, 2 or 3 substituents selected from the group consisting of $C_1$-$C_4$-alkyl and $C_1$-$C_4$-alkoxy;

each $R^5$ is independently H or methyl; and n is 0, 1 or 2.

E. 16. The method according to any of embodiments 13 to 15, where the chiral ligands are selected from the group consisting of the chiral forms of the ligands of formulae L.1, L.2, L.3, L.4, L.5, L.10 and L.11; and specifically L.2.

E.17. The method according to embodiment 13, where the chiral ligands are selected from the group consisting of the ligands of formulae L.1.1 to L.15.2:

L.1.1

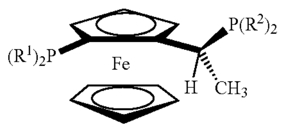

L.1.2

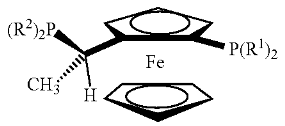

L.1.3

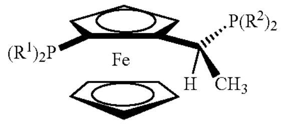

L.1.4

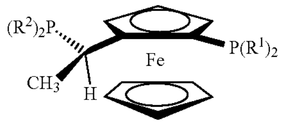

L.2.1

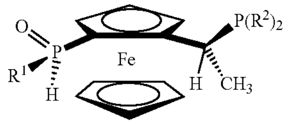

L.2.2

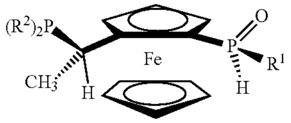

L.2.3

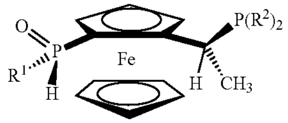

-continued
L.2.4
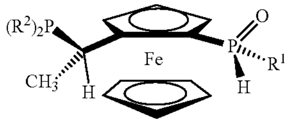
L.2.5
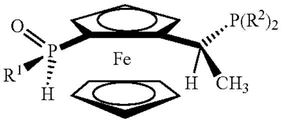
L.2.6
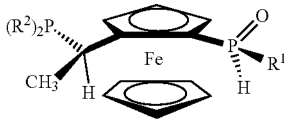
L.2.7
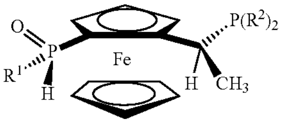
L.2.8
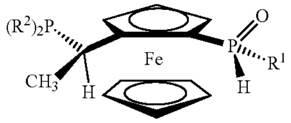
L.3.1
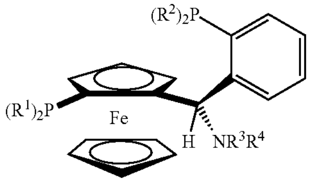
L.3.2
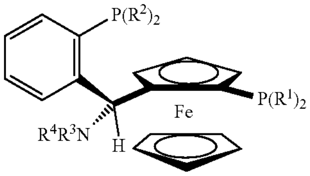
L.3.3
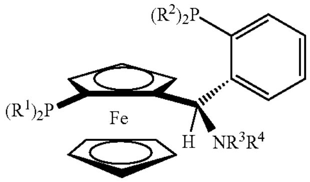
L.3.4
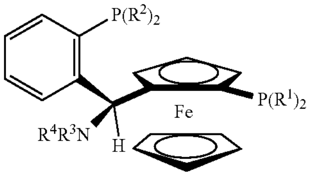
L.4.1
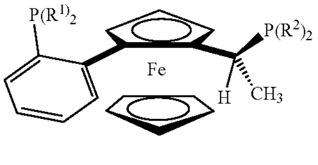
-continued
L.4.2
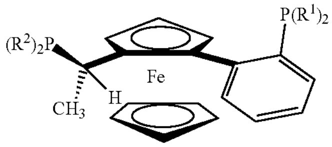
L.4.3
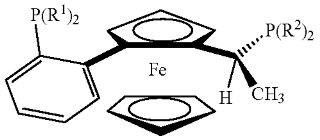
L.4.4
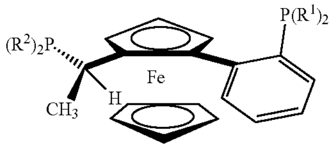
L.5.1
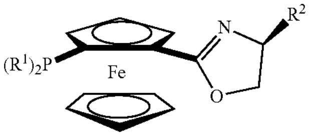
L.5.2
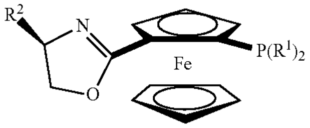
L.5.3
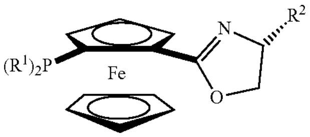
L.5.4
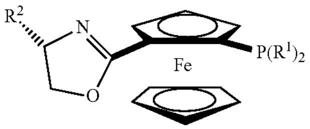
L.6.1
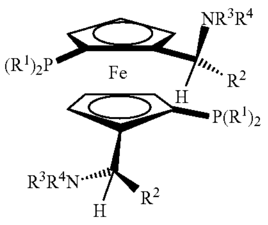
L.6.2
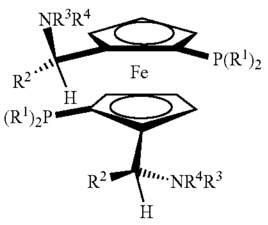

-continued
L.6.3
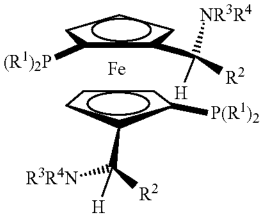
L.6.4
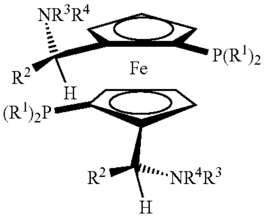
L.6.5
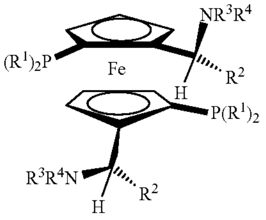
L.6.6
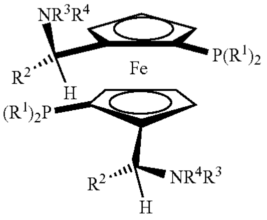
L.6.7
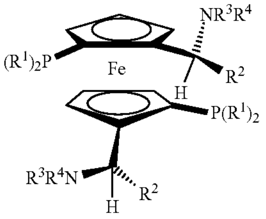
L.6.8
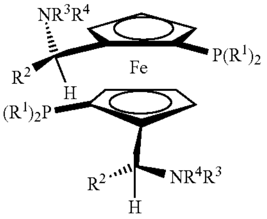
L.7.1
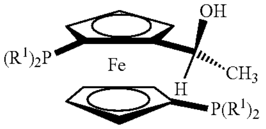
L.7.2
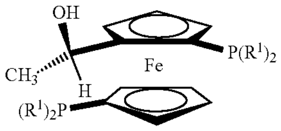
-continued
L.7.3
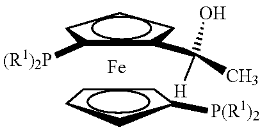
L.7.4
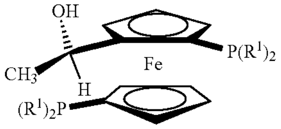
L.8.1
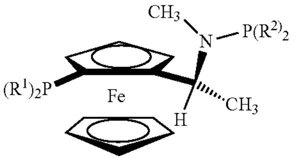
L.8.2
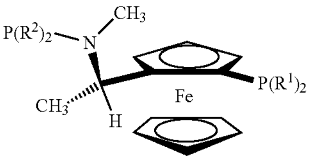
L.8.3
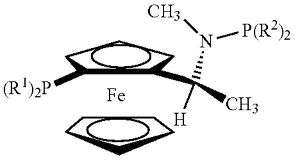
L.8.4
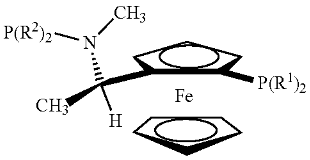
L.9.1
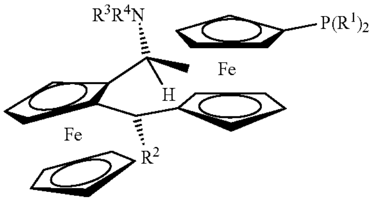
L.10.1
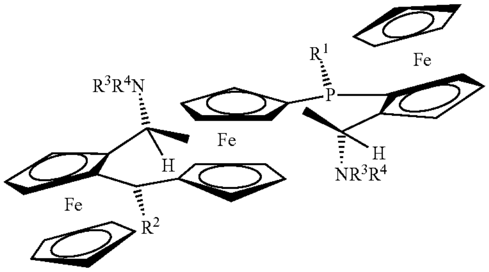

-continued

L.11.1

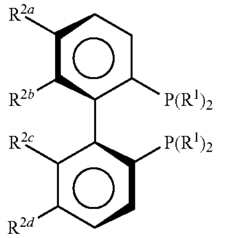

L.11.2

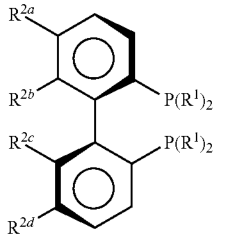

L.12.1

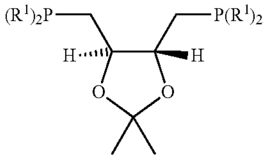

L.12.2

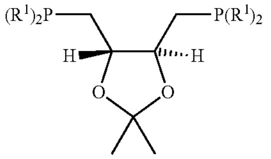

L.13.1

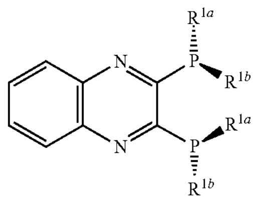

L.13.2

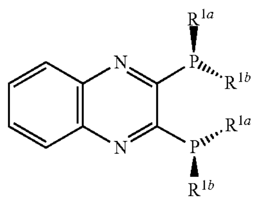

L.14.1

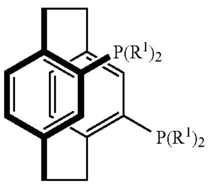

L.14.2

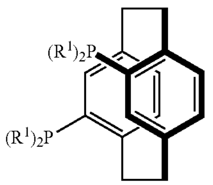

-continued

L.15.1

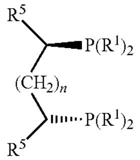

L.15.2

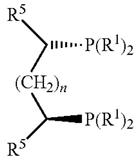

where $R^1$, $R^2$, $R^3$, $R^4$, $R^5$ and n are as defined in embodiment 13.

E.18. The method according to embodiment 17, where:

in L.1.1, L.1.2, L.1.3 and L.1.4:

the two radicals $R^1$ are identical and selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl; and the two radicals $R^2$ are identical and selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl;

in L.2.1, L.2.2, L.2.3, L.2.4, L.2.5, L.2.6, L.2.7 and L.2.8:

$R^1$ is selected from the group consisting of $C_1$-$C_6$-alkyl and phenyl which may carry 1, 2 or 3 substituents selected from the group consisting of $C_1$-$C_4$-alkyl; and the two radicals $R^2$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl;

in L.3.1, L.3.2, L.3.3 and L.3.4:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

the two radicals $R^2$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and $R^3$ and $R^4$ are methyl;

in L.4.1, L.4.2, L.4.3 and L.4.4:

the two radicals $R^1$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

the two radicals $R^2$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

in L.5.1, L.5.2, L.5.3 and L.5.4:

the two radicals $R^1$ are identical and selected from the group consisting of phenyl or naphthyl, where phenyl and naphthyl may carry 1, 2 or 3 substituents selected from the group consisting of $C_1$-$C_4$-alkyl and $C_1$-$C_4$-haloalkyl; and $R^2$ is $C_1$-$C_4$-alkyl;

in L.6.1, L.6.2, L.6.3, L.6.4, L.6.5, L.6.6, L.6.7 and L.6.8:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

$R^2$ is phenyl; and $R^3$ and $R^4$ are identical and are $C_1$-$C_4$-alkyl;

in L.7.1, L.7.2, L.7.3 and L.7.4:

$R^1$ is phenyl;

in L.8.1, L.8.2, L.8.3 and L.8.4:

$R^1$ and $R^2$ are phenyl;

in L.9.1:

the two radicals $R^1$ are identical and are $C_3$-$C_6$-cycloalkyl;

$R^2$ is phenyl; and $R^3$ and $R^4$ are identical and are $C_1$-$C_4$-alkyl;

in L.10.1:

$R^1$ and $R^2$ are phenyl; and $R^3$ and $R^4$ are identical and are $C_1$-$C_4$-alkyl;

in L.11.1 and L.11.2:

the four radicals $R^1$ are identical and selected from the group consisting of $C_1$-$C_6$-alkyl, phenyl which may carry 1, 2 or 3 substituents selected from the group consisting of $C_1$-$C_4$-alkyl, $C_1$-$C_4$-alkoxy, amino, $C_1$-$C_4$-alkylamino and di-($C_1$-$C_4$-alkyl)-amino; and a 5- or 6-membered heteroaromatic ring having 1, 2 or 3 heteroatoms selected from O, N and S are ring members;

$R^{2a}$ and $R^{2d}$ are hydrogen; and $R^{2b}$ and $R^{2c}$ are identical and are $C_1$-$C_4$-alkoxy;

or $R^{2a}$ and $R^{2b}$ form together a bridging group —CH═CH—CH═CH—; and simultaneously $R^{2c}$ and $R^{2d}$ form together a bridging group —CH═CH—CH═CH—;

or $R^{2a}$ and $R^{2b}$ form together a bridging group —O—$CH_2$—O—; and simultaneously $R^{2c}$ and $R^{2d}$ form together a bridging group —O—$CH_2$—O—;

in L.12.1 and L.12.2:

the four radicals $R^1$ are identical and are phenyl which may carry 1, 2 or 3 substituents selected from the group consisting of $C_1$-$C_4$-alkyl and $C_1$-$C_4$-alkoxy, in L.13.1 and L.13.2:

the two radicals $R^{1a}$ are identical and are $C_1$-$C_6$-alkyl;

the two radicals $R^{1b}$ are identical and are $C_1$-$C_6$-alkyl;

where $R^{1a}$ and $R^{1b}$ bound on the same P atom are not identical;

in L.14.1 and L.14.2:

$R^1$ is phenyl;

in L.15:

the four radicals $R^1$ are identical and are phenyl which may carry 1, 2 or 3 substituents selected from the group consisting of $C_1$-$C_4$-alkyl and $C_1$-$C_4$-alkoxy;

each $R^5$ is independently H or methyl; and n is 0, 1 or 2.

E.19. The method according to embodiment 18, where:

in L.1.1, L.1.2, L.1.3 and L.1.4:

the two radicals $R^1$ are identical and selected from the group consisting of $C_3$-$C_6$-alkyl, cyclohexyl, phenyl which may carry 1, 2 or 3 substituents selected from the group consisting of $C_1$-$C_4$-alkyl and $C_1$-$C_4$-haloalkyl; and naphthyl; and the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl and $C_1$-$C_4$-haloalkyl;

in L.2.1, L.2.2, L.2.3, L.2.4, L.2.5, L.2.6, L.2.7 and L.2.8:

$R^1$ is selected from the group consisting of $C_3$-$C_6$-alkyl and phenyl which may carry 1, 2 or 3 substituents selected from the group consisting of $C_1$-$C_4$-alkyl; and the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl;

in L.3.1, L.3.2, L.3.3 and L.3.4:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

the two radicals $R^2$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and $R^3$ and $R^4$ are methyl;

in L.4.1, L.4.2, L.4.3 and L.4.4:

the two radicals $R^1$ are identical and selected from the group consisting of $C_3$-$C_6$-alkyl, cyclohexyl and phenyl;

the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl and $C_1$-$C_4$-haloalkyl;

in L.5.1, L.5.2, L.5.3 and L.5.4:

the two radicals $R^1$ are identical and are naphthyl; and $R^2$ is $C_3$-$C_4$-alkyl;

in L.6.1, L.6.2, L.6.3, L.6.4, L.6.5, L.6.6, L.6.7 and L.6.8:

the two radicals $R^1$ are identical and selected from the group consisting cyclohexyl and phenyl which may carry 1, 2 or 3 substituents selected from the group consisting of $C_1$-$C_4$-alkyl and $C_1$-$C_4$-alkoxy;

$R^2$ is phenyl; and $R^3$ and $R^4$ are methyl;

in L.7.1, L.7.2, L.7.3 and L.7.4:

$R^1$ is phenyl;

in L.8.1, L.8.2, L.8.3 and L.8.4:

$R^1$ and $R^2$ are phenyl;

in L.9.1:

the two radicals $R^1$ are identical and are cyclohexyl;

$R^2$ is phenyl; and $R^3$ and $R^4$ are methyl;

in L.10.1:

$R^1$ and $R^2$ are phenyl; and $R^3$ and $R^4$ are methyl;

in L.11.1 and L.11.2:

the four radicals $R^1$ are identical and selected from the group consisting of $C_3$-$C_6$-alkyl, phenyl which may carry 1, 2 or 3 substituents selected from the group consisting of $C_3$-$C_4$-alkyl, $C_1$-$C_4$-alkoxy and di-($C_1$-$C_4$-alkyl)-amino; and furyl;

$R^{2a}$ and $R^{2d}$ are hydrogen; and $R^{2b}$ and $R^{2c}$ are identical and are $C_1$-$C_4$-alkoxy; or $R^{2a}$ and $R^{2b}$ form together a bridging group —CH═CH—CH═CH—; and simultaneously $R^{2c}$ and $R^{2d}$ form together a bridging group —CH═CH—CH═CH—; or $R^{2a}$ and $R^{2b}$ form together a bridging group —O—$CH_2$—O—; and simultaneously $R^{2c}$ and $R^{2d}$ form together a bridging group —O—$CH_2$—O—;

in L.12.1 and L.12.2:

the four radicals $R^1$ are identical and are phenyl which may carry 1, 2 or 3 substituents selected from the group consisting of $C_1$-$C_4$-alkyl and $C_1$-$C_4$-alkoxy, in L.13.1 and L.13.2:

the two radicals $R^{1a}$ are identical and are $C_3$-$C_6$-alkyl;

the two radicals $R^{1b}$ are identical and are $C_1$-$C_6$-alkyl;

where $R^{1a}$ and $R^{1b}$ bound on the same P atom are not identical;

in L.14.1 and L.14.2:

$R^1$ is phenyl;

in L.15:

the four radicals $R^1$ are identical and are phenyl which may carry 1, 2 or 3 substituents selected from the group consisting of $C_1$-$C_4$-alkyl and $C_1$-$C_4$-alkoxy;

each $R^5$ is independently H or methyl; and n is 0, 1 or 2.

E.20. The method according to any of embodiments 17 to 19, where the chiral ligands are selected from the group consisting of the ligands of formulae L.1.1, L.1.2, L.2.1, L.2.2, L.2.3, L.2.4, L.3.1, L.3.2, L.3.3, L.3.4, L.4.1, L.4.2, L.5.1, L.5.2, L.6.1, L.6.2, L.7.1, L.7.2, L.8.1, L.8.2, L.9.1, L.10.1, L.11.1, L.11.2, L.12.1, L.12.2, L.13.1, L.13.2, L.14.1, L.14.2, L.15.1 and L.15.2.

E.21. The method according to embodiments 20, where the chiral ligands are selected from the group consisting of the ligands of formulae L.2.1, L.2.3, L.3.1, L.3.2, L.3.3, L.3.4, L.4.1, L.4.2, L.5.1, L.5.2, L.10.1, L.11.1 and L.11.2.

E.22. The method according to any of the preceding embodiments, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I—S)

(I-S)

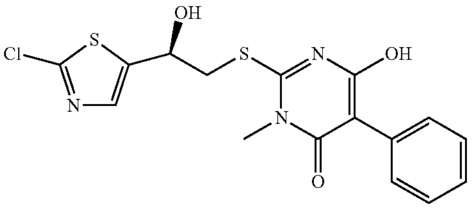

or a tautomer thereof in an enantiomeric excess of at least 50% ee, where a chiral transition metal catalyst is used which comprises a chiral ligand selected from following ligands:

L.1.1, wherein $R^1$ and $R^2$ have the following meanings:

| No. | $R^1$ | $R^2$ |
|---|---|---|
| L.1.1.1 | phenyl | tert-butyl |
| L.1.1.2 | cyclohexyl | phenyl |
| L.1.1.3 | 3,5-di-(trifluoromethyl)-phenyl | cyclohexyl |
| L.1.1.4* | 4-(trifluoromethyl)-phenyl | tert-butyl |
| L.1.1.5 | 1-naphthyl | tert-butyl |

*with Ir

L.1.2, wherein $R^1$ and $R^2$ have the following meanings:

| No. | $R^1$ | $R^2$ |
|---|---|---|
| L.1.2.1 | 1-naphthyl | tert-butyl |
| L.1.2.2 | tert-butyl | 2-methylphenyl |
| L.1.2.3 | phenyl | tert-butyl |
| L.1.2.4 | cyclohexyl | cyclohexyl |
| L.1.2.5** | 4-(trifluoromethyl)-phenyl | tert-butyl |

*with Rh

L.2.1, wherein $R^1$ and $R^2$ have the following meanings:

| No. | $R^1$ | $R^2$ |
|---|---|---|
| L.2.1.1 | tert-butyl | phenyl |
| L.2.1.2 | phenyl | tert-butyl |
| L.2.1.3 | phenyl | phenyl |
| L.2.1.4 | tert-butyl | 3,5-dimethylphenyl |
| L.2.1.5 | tert-butyl | tert-butyl |
| L.2.1.6 | tert-butyl | cyclohexyl |

L.2.2, wherein $R^1$ and $R^2$ have the following meanings:

| No. | $R^1$ | $R^2$ |
|---|---|---|
| L.2.2.1 | tert-butyl | phenyl |

L.2.3, wherein $R^1$ and $R^2$ have the following meanings:

| No. | $R^1$ | $R^2$ |
|---|---|---|
| L.2.3.1 | tert-butyl | phenyl |
| L.2.3.2 | phenyl | phenyl |
| L.2.3.3 | tert-butyl | 3,5-dimethylphenyl |
| L.2.3.4 | tert-butyl | tert-butyl |
| L.2.3.5 | tert-butyl | cyclohexyl |

L.2.4, wherein $R^1$ and $R^2$ have the following meanings:

| No. | $R^1$ | $R^2$ |
|---|---|---|
| L.2.4.1 | phenyl | tert-butyl |

L.3.1, wherein $R^1$, $R^2$, $R^3$ and $R^4$ have the following meanings:

| No. | $R^1$ | $R^2$ | $R^3$ | $R^4$ |
|---|---|---|---|---|
| L.3.1.1 | phenyl | phenyl | methyl | methyl |
| L.3.1.2* | cyclohexyl | cyclohexyl | methyl | methyl |

*with Ir

L.3.2, wherein $R^1$, $R^2$, $R^3$ and $R^4$ have the following meanings:

| No. | $R^1$ | $R^2$ | $R^3$ | $R^4$ |
|---|---|---|---|---|
| L.3.2.1** | cyclohexyl | cyclohexyl | methyl | methyl |

**with Rh

L.3.4, wherein $R^1$, $R^2$, $R^3$ and $R^4$ have the following meanings:

| No. | $R^1$ | $R^2$ | $R^3$ | $R^4$ |
|---|---|---|---|---|
| L.3.4.1 | 3,5-dimethyl-4-methoxyphenyl | 3,5-dimethyl-4-methoxyphenyl | methyl | methyl |

L.4.1, wherein $R^1$ and $R^2$ have the following meanings:

| No. | $R^1$ | $R^2$ |
|---|---|---|
| L.4.1.1 | phenyl | tert-butyl |
| L.4.1.2 | tert-butyl | tert-butyl |
| L.4.1.3 | cyclohexyl | 3,5-di-(trifluoromethyl)-phenyl |

L.4.2, wherein $R^1$ and $R^2$ have the following meanings:

| No. | $R^1$ | $R^2$ |
|---|---|---|
| L.4.2.1 | phenyl | cyclohexyl |

L.5.2, wherein $R^1$ and $R^2$ have the following meanings:

| No. | $R^1$ | $R^2$ |
|---|---|---|
| L.5.2.1 | 1-naphthyl | isopropyl |

L.6.1, wherein $R^1$, $R^2$, $R^3$ and $R^4$ have the following meanings:

| No. | $R^1$ | $R^2$ | $R^3$ | $R^4$ |
|---|---|---|---|---|
| L.6.1.1 | cyclohexyl | phenyl | methyl | methyl |
| L.6.1.2 | 3,5-dimethyl-4-methoxyphenyl | phenyl | methyl | methyl |

L.7.1, wherein $R^1$ is phenyl(ligand no. L.7.1.1)

L.8.1, wherein $R^1$ and $R^2$ are phenyl(ligand no. L.8.1.1)

L.9.1, wherein $R^1$ is cyclohexyl, $R^2$ is phenyl and $R^3$ and $R^4$ are methyl(ligand no. L.9.1.1)

L.10.1, wherein $R^1$ is phenyl, $R^2$ is phenyl and $R^3$ and $R^4$ are methyl(ligand no. L.10.1.1)

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.1 | H | $OCH_3$ | $OCH_3$ | H | 3,5-di-(tert-butyl)-4-methoxyphenyl |
| L.11.1.2* | H | $OCH_3$ | $OCH_3$ | H | 2-furyl |

*with Ru

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.2.1 | H | $OCH_3$ | $OCH_3$ | H | isopropyl |
| L.11.2.2 | H | $OCH_3$ | $OCH_3$ | H | 3,5-diisopropyl-4-(dimethylamino)-phenyl |
| L.11.2.3** | H | $OCH_3$ | $OCH_3$ | H | 2-furyl |
| L.11.2.4 | $—O—CH_2—O—$ | | $—O—CH_2—O—$ | | xylyl |
| L.11.2.5 | —CH=CH—CH=CH— | | —CH=CH—CH=CH— | | phenyl |

**with Ir

L.12.2, wherein $R^1$ is 3,5-dimethyl-4-methoxyphenyl(ligand no. L.12.2.1)

L.13.1, wherein $R^{1a}$ is tert-butyl and $R^{1b}$ is methyl(ligand no. L.13.1.1)

L.14.1, wherein $R^1$ is phenyl(ligand no. L.14.1.1)

L.15.2, wherein $R^1$ is phenyl, $R^5$ is methyl and n is 1 (ligand no. L.15.2.1)

E.23. The method according to embodiment 22, where the chiral transition metal catalyst comprises a chiral ligand selected from following ligands in combination with the transition metal as central metal as indicated in each case:

L.1.1, wherein $R^1$ and $R^2$ have the following meanings:

| No. | $R^1$ | $R^2$ | metal |
|---|---|---|---|
| L.1.1.1 | phenyl | tert-butyl | Ir |
| L.1.1.2 | cyclohexyl | phenyl | Ir, Rh |
| L.1.1.3 | 3,5-di-(trifluoromethyl)-phenyl | cyclohexyl | Ir, Rh |
| L.1.1.4 | 4-(trifluoromethyl)-phenyl | tert-butyl | Ir |
| L.1.1.5 | 1-naphthyl | tert-butyl | Ir |

L.1.2, wherein $R^1$ and $R^2$ have the following meanings:

| No. | $R^1$ | $R^2$ | metal |
|---|---|---|---|
| L.1.2.1 | 1-naphthyl | tert-butyl | Ir |
| L.1.2.2 | tert-butyl | 2-methylphenyl | Ir, Rh |
| L.1.2.3 | phenyl | tert-butyl | Ir, Rh |
| L.1.2.4 | cyclohexyl | cyclohexyl | Ir, Rh |
| L.1.2.5 | 4-(trifluoromethyl)-phenyl | tert-butyl | Rh |

L.2.1, wherein $R^1$ and $R^2$ have the following meanings:

| No. | $R^1$ | $R^2$ | metal |
|---|---|---|---|
| L.2.1.1 | tert-butyl | phenyl | Ir, Rh |
| L.2.1.2 | phenyl | tert-butyl | Ir, Rh |
| L.2.1.3 | phenyl | phenyl | Ir |
| L.2.1.4 | tert-butyl | 3,5-dimethylphenyl | Ir |
| L.2.1.5 | tert-butyl | tert-butyl | Ir |
| L.2.1.6 | tert-butyl | cyclohexyl | Ir |

L.2.2, wherein $R^1$ and $R^2$ have the following meanings:

| No. | $R^1$ | $R^2$ | metal |
|---|---|---|---|
| L.2.2.1 | tert-butyl | phenyl | Ir, Rh |

L.2.3, wherein $R^1$ and $R^2$ have the following meanings:

| No. | $R^1$ | $R^2$ | metal |
|---|---|---|---|
| L.2.3.1 | tert-butyl | phenyl | Ir |
| L.2.3.2 | phenyl | phenyl | Ir |
| L.2.3.3 | tert-butyl | 3,5-dimethylphenyl | Ir |
| L.2.3.4 | tert-butyl | tert-butyl | Ir |
| L.2.3.5 | tert-butyl | cyclohexyl | Ir |

L.2.4, wherein $R^1$ and $R^2$ have the following meanings:

| No. | $R^1$ | $R^2$ | metal |
|---|---|---|---|
| L.2.4.1 | phenyl | tert-butyl | Ir |

L.3.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.1.1 | phenyl | phenyl | methyl | methyl | Rh |
| L.3.1.2 | cyclohexyl | cyclohexyl | methyl | methyl | Ir |

L.3.2, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.2.1 | cyclohexyl | cyclohexyl | methyl | methyl | Rh |

L.3.4, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.4.1 | 3,5-dimethyl-4-methoxyphenyl | 3,5-dimethyl-4-methoxyphenyl | methyl | methyl | Rh |

L.4.1, wherein $R^1$ and $R^2$ have the following meanings:

| No. | $R^1$ | $R^2$ | metal |
|---|---|---|---|
| L.4.1.1 | phenyl | tert-butyl | Rh |
| L.4.1.2 | tert-butyl | tert-butyl | Rh |
| L.4.1.3 | cyclohexyl | 3,5-di-(trifluoromethyl)-phenyl | Rh |

L.4.2, wherein $R^1$ and $R^2$ have the following meanings:

| No. | $R^1$ | $R^2$ | metal |
|---|---|---|---|
| L.4.2.1 | phenyl | cyclohexyl | Ir, Rh |

L.5.2, wherein $R^1$ and $R^2$ have the following meanings:

| No. | $R^1$ | $R^2$ | metal |
|---|---|---|---|
| L.5.2.1 | 1-naphthyl | isopropyl | Ir |

L.6.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.6.1.1 | cyclohexyl | phenyl | methyl | methyl | Rh |
| L.6.1.2 | 3,5-dimethyl-4-methoxyphenyl | phenyl | methyl | methyl | Rh |

L.7.1, wherein $R^1$ is phenyl(ligand no. L.7.1.1); metal=Ir

L.8.1, wherein $R^1$ and $R^2$ are phenyl(ligand no. L.8.1.1); metal=Ir, Rh

L.9.1, wherein $R^1$ is cyclohexyl, $R^2$ is phenyl and $R^3$ and $R^4$ are methyl(ligand no. L.9.1.1); metal=Ir, Rh L.10.1, wherein $R^1$ is phenyl, $R^2$ is phenyl and $R^3$ and $R^4$ are methyl(ligand no. L.10.1.1); metal=Ir L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.1 | H | $OCH_3$ | $OCH_3$ | H | 3,5-di-(tert-butyl)-4-methoxyphenyl | Rh |
| L.11.1.2 | H | $OCH_3$ | $OCH_3$ | H | 2-furyl | Ru |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.2.1 | H | $OCH_3$ | $OCH_3$ | H | isopropyl | Ir, Rh |
| L.11.2.2 | H | $OCH_3$ | $OCH_3$ | H | 3,5-diisopropyl-4-(dimethylamino)-phenyl | Ir |
| L.11.2.3 | H | $OCH_3$ | $OCH_3$ | H | 2-furyl | Ir |
| L.11.2.4 | $-O-CH_2-O-$ | | $-O-CH_2-O-$ | | xylyl | Ir |
| L.11.2.5 | $-CH=CH-CH=CH-$ | | $-CH=CH-CH=CH-$ | | phenyl | Ir |

L.12.2, wherein $R^1$ is 3,5-dimethyl-4-methoxyphenyl(ligand no. L.12.2.1); metal=Ir L.13.1, wherein $R^{1a}$ is tert-butyl and $R^{1b}$ is methyl(ligand no. L.13.1.1); metal=Ir L.14.1, wherein $R^1$ is phenyl(ligand no. L.14.1.1); metal=Ir, Rh L.15.2, wherein $R^1$ is phenyl, $R^5$ is methyl and n is 1 (ligand no. L.15.2.1); metal=Ir E.24. The method according to any of embodiments 22 or 23, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I—S) or a tautomer thereof in an enantiomeric excess of at least 55% ee.

E.25. The method according to embodiment 24, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I—S) or a tautomer thereof in an enantiomeric excess of at least 60% ee.

E.26. The method according to embodiment 25, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I—S) or a tautomer thereof in an enantiomeric excess of even more preferably at least 70% ee.

E.27. The method according to embodiment 26, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I—S) or a tautomer thereof in an enantiomeric excess of in particular at least 80% ee.

E.28. The method according to any of embodiments 22 to 27, where the chiral ligands are selected from the group consisting of the ligands of formulae L.2.1, L.3.1, L.4.1, L.10.1 and L.11.1.

E.29. The method according to any of embodiments 22 to 28, where the chiral ligand is selected from following ligands:

L.2.1, wherein $R^1$ and $R^2$ have the following meanings:

| No. | $R^1$ | $R^2$ |
|---|---|---|
| L.2.1.2 | phenyl | tert-butyl |

L.3.1, wherein $R^1$, $R^2$, $R^3$ and $R^4$ have the following meanings:

| No. | $R^1$ | $R^2$ | $R^3$ | $R^4$ |
|---|---|---|---|---|
| L.3.1.1 | phenyl | phenyl | methyl | methyl |

L.4.1, wherein $R^1$ and $R^2$ have the following meanings:

| No. | $R^1$ | $R^2$ |
|---|---|---|
| L.4.1.2 | tert-butyl | tert-butyl |

L.10.1, wherein $R^1$ is phenyl, $R^2$ is phenyl and $R^3$ and $R^4$ are methyl(ligand no. L.10.1.1)

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.1 | H | $OCH_3$ | $OCH_3$ | H | 3,5-di-(tert-butyl)-4-methoxyphenyl |

E.30. The method according to embodiment 29, where the chiral transition metal catalyst comprises a chiral ligand selected from following ligands in combination with the transition metal as central metal as indicated in each case:

L.2.1, wherein $R^1$ and $R^2$ have the following meanings:

| No. | $R^1$ | $R^2$ | metal |
|---|---|---|---|
| L.2.1.2 | phenyl | tert-butyl | Ir |

L.3.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.1.1 | phenyl | phenyl | methyl | methyl | Rh |

L.4.1, wherein $R^1$ and $R^2$ have the following meanings:

| No. | $R^1$ | $R^2$ | metal |
|---|---|---|---|
| L.4.1.2 | tert-butyl | tert-butyl | Rh |

L.10.1, wherein $R^1$ is phenyl, $R^2$ is phenyl and $R^3$ and $R^4$ are methyl(ligand no. L.10.1.1); metal=Ir L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.1 | H | $OCH_3$ | $OCH_3$ | H | 3,5-di-(tert-butyl)-4-methoxyphenyl | Rh |

E.31. The method according to any of embodiments 29 or 30, where the chiral ligand is L.2.1.2.

E.32. The method according to embodiment 31, where the chiral transition metal catalyst is obtainable by reacting the ligand L.2.1.2 with $[Ir(COD)_2]BARF$ in a molar ratio of from 2:1 to 1:2, where COD is cycloocta-1,5-diene and BARF is tetrakis(3,5-bis(trifluoromethyl)phenyl)borate.

E.33. The method according to any of embodiments 1 to 21, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R)

(I-R)

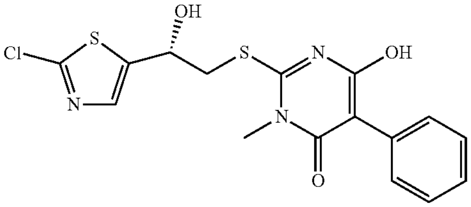

or a tautomer thereof in an enantiomeric excess of at least 50% ee, where a chiral transition metal catalyst is used which comprises a chiral ligand selected from following ligands:

L.1.1, wherein $R^1$ and $R^2$ have the following meanings:

| No. | $R^1$ | $R^2$ |
|---|---|---|
| L.1.1.5 | 1-naphthyl | tert-butyl |
| L.1.1.6 | tert-butyl | 2-methylphenyl |
| L.1.1.1 | phenyl | tert-butyl |
| L.1.1.7 | cyclohexyl | cyclohexyl |
| L.1.1.4* | 4-(trifluoromethyl)-phenyl | tert-butyl |

*with Rh

L.1.2, wherein $R^1$ and $R^2$ have the following meanings:

| No. | $R^1$ | $R^2$ |
|---|---|---|
| L.1.2.3 | phenyl | tert-butyl |
| L.1.2.6 | cyclohexyl | phenyl |
| L.1.2.7 | 3,5-di-(trifluoromethyl)-phenyl | cyclohexyl |
| L.1.2.5** | 4-(trifluoromethyl)-phenyl | tert-butyl |
| L.1.2.1 | 1-naphthyl | tert-butyl |

**with Ir

L.2.1, wherein $R^1$ and $R^2$ have the following meanings:

| No. | $R^1$ | $R^2$ |
|---|---|---|
| L.2.1.1 | tert-butyl | phenyl |

L.2.2, wherein $R^1$ and $R^2$ have the following meanings:

| No. | $R^1$ | $R^2$ |
|---|---|---|
| L.2.2.1 | tert-butyl | phenyl |
| L.2.2.2 | phenyl | tert-butyl |
| L.2.2.3 | phenyl | phenyl |
| L.2.2.4 | tert-butyl | 3,5-dimethylphenyl |
| L.2.2.5 | tert-butyl | tert-butyl |
| L.2.2.6 | tert-butyl | cyclohexyl |

L.2.3, wherein $R^1$ and $R^2$ have the following meanings:

| No. | $R^1$ | $R^2$ |
|---|---|---|
| L.2.3.6 | phenyl | tert-butyl |
| L.2.3.1 | tert-butyl | phenyl |

L.2.4, wherein $R^1$ and $R^2$ have the following meanings:

| No. | $R^1$ | $R^2$ |
|---|---|---|
| L.2.4.2 | tert-butyl | phenyl |
| L.2.4.3 | phenyl | phenyl |
| L.2.4.4 | tert-butyl | 3,5-dimethylphenyl |
| L.2.4.5 | tert-butyl | tert-butyl |
| L.2.4.6 | tert-butyl | cyclohexyl |

L.3.1, wherein $R^1$, $R^2$, $R^3$ and $R^4$ have the following meanings:

| No. | $R^1$ | $R^2$ | $R^3$ | $R^4$ |
|---|---|---|---|---|
| L.3.1.2* | cyclohexyl | cyclohexyl | methyl | methyl |

*with Rh

L.3.2, wherein $R^1$, $R^2$, $R^3$ and $R^4$ have the following meanings:

| No. | $R^1$ | $R^2$ | $R^3$ | $R^4$ |
|---|---|---|---|---|
| L.3.2.2 | phenyl | phenyl | methyl | methyl |
| L.3.2.1** | cyclohexyl | cyclohexyl | methyl | methyl |

**with Ir

L.3.3, wherein $R^1$, $R^2$, $R^3$ and $R^4$ have the following meanings:

| No. | $R^1$ | $R^2$ | $R^3$ | $R^4$ |
|---|---|---|---|---|
| L.3.3.1 | 3,5-dimethyl-4-methoxyphenyl | 3,5-dimethyl-4-methoxyphenyl | methyl | methyl |

L.4.1, wherein $R^1$ and $R^2$ have the following meanings:

| No. | $R^1$ | $R^2$ |
|---|---|---|
| L.4.1.4 | phenyl | cyclohexyl |

L.4.2, wherein $R^1$ and $R^2$ have the following meanings:

| No. | $R^1$ | $R^2$ |
|---|---|---|
| L.4.2.2 | phenyl | tert-butyl |
| L.4.2.3 | tert-butyl | tert-butyl |
| L.4.2.4 | cyclohexyl | 3,5-di-(trifluoromethyl)-phenyl |

L.5.1, wherein $R^1$ and $R^2$ have the following meanings:

| No. | $R^1$ | $R^2$ |
|---|---|---|
| L.5.1.1 | 1-naphthyl | isopropyl |

L.6.2, wherein $R^1$, $R^2$, $R^3$ and $R^4$ have the following meanings:

| No. | $R^1$ | $R^2$ | $R^3$ | $R^4$ |
|---|---|---|---|---|
| L.6.2.1 | cyclohexyl | phenyl | methyl | methyl |
| L.6.2.2 | 3,5-dimethyl-4-methoxyphenyl | phenyl | methyl | methyl |

L.7.2, wherein $R^1$ is phenyl(ligand no. L.7.2.1)

L.8.2, wherein $R^1$ and $R^2$ are phenyl(ligand no. L.8.2.1)

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.3 | H | $OCH_3$ | $OCH_3$ | H | isopropyl |
| L.11.1.4 | H | $OCH_3$ | $OCH_3$ | H | 3,5-diisopropyl-4-(dimethylamino)-phenyl |
| L.11.1.2* | H | $OCH_3$ | $OCH_3$ | H | 2-furyl |
| L.11.1.5 | $-O-CH_2-O-$ | | $-O-CH_2-O-$ | | xylyl |
| L.11.1.6 | $-CH{=}CH-CH{=}CH-$ | | $-CH{=}CH-CH{=}CH-$ | | phenyl |

*with Ir

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.2.6 | H | $OCH_3$ | $OCH_3$ | H | 3,5-di-(tert-butyl)-4-methoxyphenyl |
| L.11.2.3** | H | $OCH_3$ | $OCH_3$ | H | 2-furyl |

**with Ru

L.12.1, wherein $R^1$ is 3,5-dimethyl-4-methoxyphenyl(ligand no. L.12.1.1)

L.13.2, wherein $R^{1a}$ is tert-butyl and $R^{1b}$ is methyl(ligand no. L.13.2.1)

L.14.2, wherein $R^1$ is phenyl(ligand no. L.14.2.1)

L.15.1, wherein $R^1$ is phenyl, $R^5$ is methyl and n is 1 (ligand no. L.15.1.1)

L.15.2, wherein $R^1$ is phenyl, $R^5$ is methyl and n is 1 (ligand no. L.15.2.1)

E.34. The method according to embodiment 33, where the chiral transition metal catalyst comprises a chiral ligand selected from following ligands in combination with the transition metal as central metal as indicated in each case:

L.1.1, wherein $R^1$ and $R^2$ have the following meanings.

| No. | $R^1$ | $R^2$ | metal |
|---|---|---|---|
| L.1.1.5 | 1-naphthyl | tert-butyl | Ir |
| L.1.1.6 | tert-butyl | 2-methylphenyl | Ir, Rh |
| L.1.1.1 | phenyl | tert-butyl | Ir, Rh |
| L.1.1.7 | cyclohexyl | cyclohexyl | Ir, Rh |
| L.1.1.4 | 4-(trifluoromethyl)-phenyl | tert-butyl | Rh |

L.1.2, wherein $R^1$ and $R^2$ have the following meanings:

| No. | $R^1$ | $R^2$ | metal |
|---|---|---|---|
| L.1.2.3 | phenyl | tert-butyl | Ir |
| L.1.2.6 | cyclohexyl | phenyl | Ir, Rh |
| L.1.2.7 | 3,5-di-(trifluoromethyl)-phenyl | cyclohexyl | Ir, Rh |
| L.1.2.5 | 4-(trifluoromethyl)-phenyl | tert-butyl | Ir |
| L.1.2.1 | 1-naphthyl | tert-butyl | Ir |

L.2.1, wherein $R^1$ and $R^2$ have the following meanings:

| No. | $R^1$ | $R^2$ | metal |
|---|---|---|---|
| L.2.1.1 | tert-butyl | phenyl | Ir, Rh |

L.2.2, wherein $R^1$ and $R^2$ have the following meanings:

| No. | $R^1$ | $R^2$ | metal |
|---|---|---|---|
| L.2.2.1 | tert-butyl | phenyl | Ir, Rh |
| L.2.2.2 | phenyl | tert-butyl | Ir, Rh |
| L.2.2.3 | phenyl | phenyl | Ir |
| L.2.2.4 | tert-butyl | 3,5-dimethylphenyl | Ir |
| L.2.2.5 | tert-butyl | tert-butyl | Ir |
| L.2.2.6 | tert-butyl | cyclohexyl | Ir |

L.2.3, wherein $R^1$ and $R^2$ have the following meanings:

| No. | $R^1$ | $R^2$ | metal |
|---|---|---|---|
| L.2.3.6 | phenyl | tert-butyl | Ir |
| L.2.3.1 | tert-butyl | phenyl | Ir |

| No. | $R^1$ | $R^2$ | metal |
|---|---|---|---|
| L.2.4.2 | tert-butyl | phenyl | Ir |
| L.2.4.3 | phenyl | phenyl | Ir |
| L.2.4.4 | tert-butyl | 3,5-dimethylphenyl | Ir |
| L.2.4.5 | tert-butyl | tert-butyl | Ir |
| L.2.4.6 | tert-butyl | cyclohexyl | Ir |

L.2.4, wherein $R^1$ and $R^2$ have the following meanings:

L.3.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.1.2 | cyclohexyl | cyclohexyl | methyl | methyl | Rh |

L.3.2, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.2.2 | phenyl | phenyl | methyl | methyl | Rh |
| L.3.2.1 | cyclohexyl | cyclohexyl | methyl | methyl | Ir |

L.3.3, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.3.1 | 3,5-dimethyl-4-methoxyphenyl | 3,5-dimethyl-4-methoxyphenyl | methyl | methyl | Rh |

L.4.1, wherein $R^1$ and $R^2$ have the following meanings:

| No. | $R^1$ | $R^2$ | metal |
|---|---|---|---|
| L.4.1.4 | phenyl | cyclohexyl | Ir, Rh |

L.4.2, wherein $R^1$ and $R^2$ have the following meanings:

| No. | $R^1$ | $R^2$ | metal |
|---|---|---|---|
| L.4.2.2 | phenyl | tert-butyl | Rh |
| L.4.2.3 | tert-butyl | tert-butyl | Rh |
| L.4.2.4 | cyclohexyl | 3,5-di-(trifluoromethyl)-phenyl | Rh |

L.5.1, wherein $R^1$ and $R^2$ have the following meanings:

| No. | $R^1$ | $R^2$ | metal |
|---|---|---|---|
| L.5.1.1 | 1-naphthyl | isopropyl | Ir |

L.6.2, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.6.2.1 | cyclohexyl | phenyl | methyl | methyl | Rh |
| L.6.2.2 | 3,5-dimethyl-4-methoxyphenyl | phenyl | methyl | methyl | Rh |

L.7.2, wherein $R^1$ is phenyl(ligand no. L.7.2.1); metal=Ir

L.8.2, wherein $R^1$ and $R^2$ are phenyl(ligand no. L.8.2.1); metal=Ir, Rh

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.3 | H | $OCH_3$ | $OCH_3$ | H | isopropyl | Ir, Rh |
| L.11.1.4 | H | $OCH_3$ | $OCH_3$ | H | 3,5-diisopropyl-4-(dimethylamino)-phenyl | Ir |
| L.11.1.2 | H | $OCH_3$ | $OCH_3$ | H | 2-furyl | Ir |
| L.11.1.5 | $—O—CH_2—O—$ | | $—O—CH_2—O—$ | | xylyl | Ir |
| L.11.1.6 | —CH═CH—CH═CH— | | —CH═CH—CH═CH— | | phenyl | Ir |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.2.6 | H | $OCH_3$ | $OCH_3$ | H | 3,5-di-(tert-butyl)-4-methoxyphenyl | Rh |
| L.11.2.3 | H | $OCH_3$ | $OCH_3$ | H | 2-furyl | Ru |

L.12.1, wherein $R^1$ is 3,5-dimethyl-4-methoxyphenyl(ligand no. L.12.1.1); metal=Ir L.13.2, wherein $R^{1a}$ is tert-butyl and $R^{1b}$ is methyl(ligand no. L.13.2.1); metal=Ir L.14.2, wherein $R^1$ is phenyl(ligand no. L.14.2.1); metal=Ir, Rh L.15.1, wherein $R^1$ is phenyl, $R^5$ is methyl and n is 1 (ligand no. L.15.1.1); metal=Ir L.15.2, wherein $R^1$ is phenyl, $R^5$ is methyl and n is 1 (ligand no. L.15.2.1); metal=Ir E.35. The method according to any of embodiments 33 or 34, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) or a tautomer thereof in an enantiomeric excess of at least 55% ee.

E.36. The method according to embodiment 35, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) or a tautomer thereof in an enantiomeric excess of at least 60% ee.

E.37. The method according to embodiment 36, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) or a tautomer thereof in an enantiomeric excess of even more preferably at least 70% ee.

E.38. The method according to embodiment 37, for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R) or a tautomer thereof in an enantiomeric excess of in particular at least 80% ee.

E.39. The method according to any of embodiments 33 to 38, where the chiral ligands are selected from the group consisting of the ligands of formulae L.2.3, L.3.2, L.3.3, L.4.2, L.5.1, L.11.1 and L.11.2.

E.40. The method according to any of embodiments 33 to 39, where the chiral ligand is selected from:

L.2.3, wherein $R^1$ and $R^2$ have the following meanings:

| No. | $R^1$ | $R^2$ |
|---|---|---|
| L.2.3.6 | phenyl | tert-butyl |

L.3.2, wherein $R^1$, $R^2$, $R^3$ and $R^4$ have the following meanings:

| No. | $R^1$ | $R^2$ | $R^3$ | $R^4$ |
|---|---|---|---|---|
| L.3.2.2 | phenyl | phenyl | methyl | methyl |

L.3.3, wherein $R^1$, $R^2$, $R^3$ and $R^4$ have the following meanings:

| No. | $R^1$ | $R^2$ | $R^3$ | $R^4$ |
|---|---|---|---|---|
| L.3.3.1 | 3,5-dimethyl-4-methoxyphenyl | 3,5-dimethyl-4-methoxyphenyl | methyl | methyl |

L.4.2, wherein $R^1$ and $R^2$ have the following meanings:

| No. | $R^1$ | $R^2$ |
|---|---|---|
| L.4.2.4 | cyclohexyl | 3,5-di-(trifluoromethyl)-phenyl |

L.5.1, wherein $R^1$ and $R^2$ have the following meanings:

| No. | $R^1$ | $R^2$ |
|---|---|---|
| L.5.1.1 | 1-naphthyl | isopropyl |

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.3 | H | $OCH_3$ | $OCH_3$ | H | isopropyl |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.2.3** | H | $OCH_3$ | $OCH_3$ | H | 2-furyl |

**with Ru

E.41. The method according to embodiment 40, where the chiral transition metal catalyst comprises a chiral ligand selected from following ligands in combination with the transition metal as central metal as indicated in each case:

L.2.3, wherein $R^1$ and $R^2$ have the following meanings:

| No. | $R^1$ | $R^2$ | metal |
|---|---|---|---|
| L.2.3.6 | phenyl | tert-butyl | Ir |

L.3.2, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.2.2 | phenyl | phenyl | methyl | methyl | Rh |

L.3.3, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.3.1 | 3,5-dimethyl-4-methoxyphenyl | 3,5-dimethyl-4-methoxyphenyl | methyl | methyl | Rh |

L.4.2, wherein $R^1$ and $R^2$ have the following meanings:

| No. | $R^1$ | $R^2$ | metal |
|---|---|---|---|
| L.4.2.4 | cyclohexyl | 3,5-di-(trifluoromethyl)-phenyl | Rh |

L.5.1, wherein $R^1$ and $R^2$ have the following meanings:

| No. | $R^1$ | $R^2$ | metal |
|---|---|---|---|
| L.5.1.1 | 1-naphthyl | isopropyl | Ir |

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.3 | H | $OCH_3$ | $OCH_3$ | H | isopropyl | Ir, Rh |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.2.3 | H | $OCH_3$ | $OCH_3$ | H | 2-furyl | Ru |

E.42. The method according to any of the preceding embodiments, where the catalyst, in addition to the phosphine ligands as defined in any of embodiments E. 12 to E.41, contains one or two further ligands coordinated to the central metal.

E.43. The method according to embodiment E.42, where the further ligands are selected from halogenide ligands (e.g. Cl, Br or I; among which Cl is preferred), sulfonate ligands (e.g. triflate, mesylate, tosylate or nonaflate; among which triflate is preferred), carboxylate ligands (e.g. acetate, trifluoroacetate, benzoate) and neutral ligands selected from ethylene, COD (cycloocta-1,5-diene), NBD (norbornadiene) and an aromatic ring, such as Cp, Cp*, benzene, mesitylene or para-cymene, where in case that the catalyst contains only neutral ligands, the positive charge is neutralized by a counteranion selected from halogenides, such as $Cl^-$, $Br^-$ or $I^-$; sulfonates, such as triflate, mesylate, tosylate or nonaflate; carboxylates, such as acetate, trifluoroacetate or benzoate; and non-nucleophilic anions, such as BARF (tetrakis (3,5-bis(trifluoromethyl)phenyl)borate; also abbreviated as $BAR_F$ or $[BAr_4^F]^-$.

E.44. The method according to any of the preceding embodiments, where the reaction is carried out at a hydrogen pressure of from 1 to 100 bar.

E.45. The method according to embodiment 44, where the reaction is carried out at a hydrogen pressure of from 2 to 80 bar.

E.46. The method according to embodiment 45, where the reaction is carried out at a hydrogen pressure of from 10 to 60 bar.

E.47. The method according to embodiment 46, where the reaction is carried out at a hydrogen pressure of from 40 to 60 bar.

E.48. The method according to any of the preceding embodiments, where the reaction is carried out at a temperature of from −5 to 120° C.

E.49. The method according to embodiment 48, where the reaction is carried out at a temperature of from 10 to 80° C.

E.50. The method according to embodiment 49, where the reaction is carried out at a temperature of from 30 to 60° C.

E.51. The method according to any of the preceding embodiments, where the reaction is carried out in the presence of a solvent.

E.52. The method according to embodiment 51, where the solvent is selected from the group consisting of polar aprotic solvents, polar protic solvents, $C_1$-$C_4$-alkyl acetates, chlorinated alkanes, open-chained ethers, aromatic solvents and mixtures thereof.

E.53. The method according to embodiment 52, where the solvent is selected from the group consisting of tetrahydrofuran, 2-methyltetrahydrofuran, 1,3-dioxane, 1,4-dioxane, dimethylsulfoxide (DMSO), N,N-dimethylformamide (DMF), N, N-dimethylacetamide (DMAC), $C_1$-$C_4$-alkanols, fluorinated $C_1$-$C_4$-alkanols, $C_1$-$C_4$-alkyl acetates, chlorinated $C_1$-$C_2$-alkanes, di-($C_1$-$C_4$-alkyl)-ethers, benzene, toluene, trifluorotoluene, the xylenes, chlorobenzene, dichlorobenzene, anisole and mixtures of the aforementioned solvents.

E.54. The method according to embodiment 53, where the solvent is selected from the group consisting of 2-methyltetrahydrofuran, 1,4-dioxane, DMSO, DMF, $C_1$-$C_3$-alkanols, 2,2,2-trifluoroethanol, ethyl acetate, chlorinated $C_1$-$C_2$-alkanes, di-($C_1$-$C_4$-alkyl)-ethers, toluene, anisole and mixtures of the aforementioned solvents.

E.55. The method according to embodiment 54, where the solvent is selected from the group consisting of 2-methyltetrahydrofuran, mixtures of 2-methyltetrahydrofuran and a $C_1$-$C_3$-alkanol; mixtures of 1,4-dioxane and a $C_1$-$C_3$-alkanol, 2,2,2-trifluoroethanol or DMSO; ethyl acetate, mixtures of ethyl acetate and a $C_1$-$C_3$-alkanol; mixtures of a di-($C_1$-$C_4$-alkyl)-ether and a $C_1$-$C_3$-alkanol; and mixtures of anisole a $C_1$-$C_3$-alkanol.

E.56. The method according to embodiment 55, where the solvent is selected from the group consisting of 2-methyltetrahydrofuran and mixtures of 2-methyltetrahydrofuran and a $C_1$-$C_3$-alkanol.

E.57. The method according to embodiment 56, where the solvent is selected from the group consisting of 2-methyltetrahydrofuran and mixtures of 2-methyltetrahydrofuran and methanol.

E.58. The method according to any of the preceding embodiments, where the reaction is carried out in the presence of an additive selected from the group consisting of organic bases, organic or inorganic Brønsted or Lewis acids, borate esters, zinc halides and zinc sulfonates.

E.59. The method according to embodiment 58, where the additive is selected from the group consisting of $C_1$-$C_6$-trialkylamines, $BF_3$ and adducts thereof, borate esters, zinc halides and zinc sulfonates.

E.60. The method according to embodiment 59, where the additive is selected from the group consisting of $BF_3$, $BF_3$ adducts and borate esters.

E.61. The method according to embodiment 60, where the additive is selected from the group consisting of a $BF_3$ adduct and a tri-($C_1$-$C_4$-alkyl)-borate ester.

E.62. The method according to embodiment 61, where the additive is selected from the group consisting of $BF_3$ etherate and $B(OiPr)_3$ (OiPr=isopropoxy=—$OCH(CH_3)_2$).

E.63. The method according to any of embodiment 58 to 62, where the additive is used in such an amount that the molar ratio of additive and the compound 1 is in the range of from 1:100 to 10:1.

E.64. The method according to embodiment 63, where the additive is used in such an amount that the molar ratio of additive and the compound 1 is in the range of from 1:10 to 5:1.

E.65. The method according to embodiment 64, where the additive is used in such an amount that the molar ratio of additive and the compound 1 is in the range of from 1:10 to 1:1.

The reaction sequence of the method of the invention can be depicted as follows:

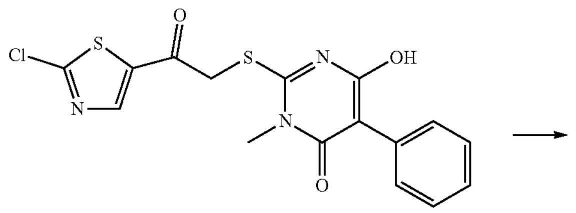

1

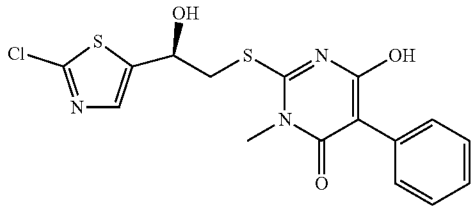

(I)

The chiral transition metal catalyst is preferably selected from group VIII metal catalysts. Group VIII metal catalysts refer to catalysts having a metal from group VIII of the periodic system of elements as central metal. Group VIII relates to the IUPAC group definition valid before 1985 and corresponds to groups 8, 9 and 10 of the current IUPAC group designation. Group 8 comprises Fe, Ru and Os, group 9 Co, Rh and Ir and group 10 Ni, Pd and Pt. Preference is given to group 8 and 9 metal catalysts. Among these, in turn, preference is given to Ru, Rh and Ir catalysts. Specifically, the chiral transition metal catalyst is one with Rh or Ir as central atom.

Preferably, the chiral transition metal catalyst, calculated on the basis of the transition metal content, is used in an amount of 0.01 to 10 mol %, more preferably from 0.05 to 5 mol-%, even more preferably from 0.1 to 5 mol-%, and in particular from 1 to 5 mol-%, relative to 1 mol of the compound 1 (i.e. 1 mol of the compound 1 corresponds to 100 mol-%).

Chirality of the chiral transition metal catalyst is preferably based on the presence of one or more chiral ligands coordinatively bound to the central transition metal.

The chiral transition metal catalyst can be used in preformed form. In the preformed catalyst, the central metal is coordinatively bound to one or more chiral ligands. Alternatively, the chiral transition metal catalyst is formed in situ by reaction of a transition metal precursor compound and one or more chiral ligands.

The chiral ligands are preferably selected from chiral phosphine ligands. The chiral phosphine ligands comprise one or more phosphino groups. The chiral phosphine ligands are preferably at least bidentate ligands. In case that the chiral ligands comprise just one phosphino group, they comprise additionally at least one of a phosphine oxide group or an amino group or an imino group which serve as further coordination points.

Preferably, the chiral transition metal catalyst comprises one or more chiral ligands coordinated to a transition metal, where the chiral ligands are selected from the group consisting of the chiral forms of the ligands of formulae L.1 to L.15:

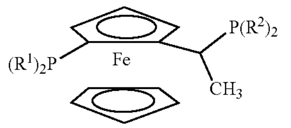

L.1

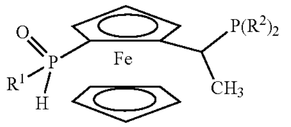

L.2

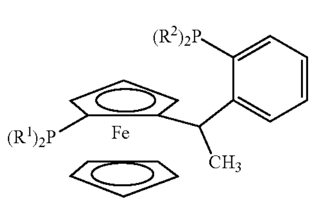

L.3

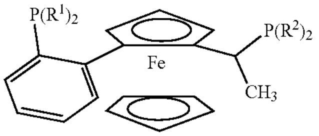

L.4

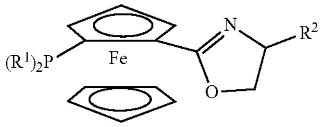

L.5

-continued

L.6

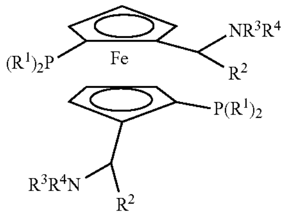

L.7

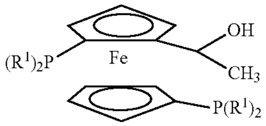

L.8

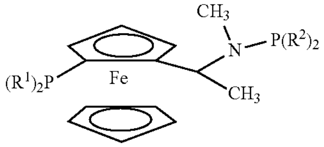

L.9

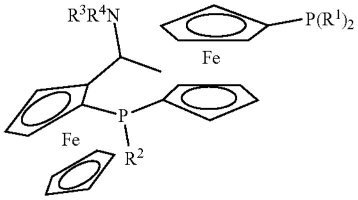

L.10

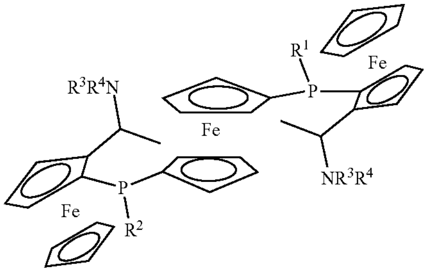

L.11

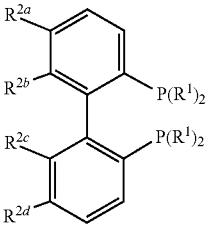

L.12

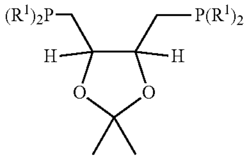

L.13

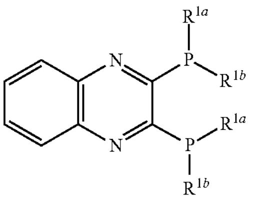

-continued

L.14.1

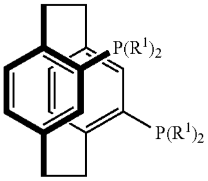

L.14.2

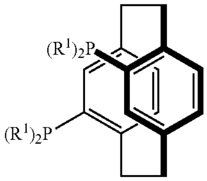

L.15

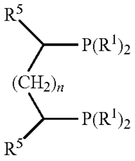

where in L.1:

$R^1$ and $R^2$, independently of each other and independently of each occurrence, are selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl;

in L.2:

$R^1$ and $R^2$, independently of each other and independently of each occurrence, are selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl;

in L.3:

$R^1$ and $R^2$, independently of each other and independently of each occurrence, are selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and $R^3$ and $R^4$ are methyl;

in L.4:

$R^1$ and $R^2$, independently of each other and independently of each occurrence, are selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

in L.5:

$R^1$ is phenyl or naphthyl, where phenyl and naphthyl may carry 1, 2 or 3 substituents selected from the group consisting of $C_1$-$C_4$-alkyl and $C_1$-$C_4$-haloalkyl; and $R^2$ is $C_1$-$C_4$-alkyl;

in L.6:

$R^1$ is selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

$R^2$ is phenyl; and $R^3$ and $R^4$, independently of each other, are $C_1$-$C_4$-alkyl;

in L.7:

$R^1$ is phenyl;

in L.8:

$R^1$ and $R^2$ are phenyl;

in L.9:

$R^1$ is $C_3$-$C_6$-cycloalkyl;

$R^2$ is phenyl; and $R^3$ and $R^4$, independently of each other, are $C_1$-$C_4$-alkyl;

in L.10:

$R^1$ and $R^2$ are phenyl; and $R^3$ and $R^4$, independently of each other, are $C_1$-$C_4$-alkyl;

in L.11:

each $R^1$ is independently selected from the group consisting of $C_1$-$C_6$-alkyl, phenyl which may carry 1, 2 or 3 substituents selected from the group consisting of $C_1$-$C_4$-alkyl, $C_1$-$C_4$-alkoxy, amino, $C_1$-$C_4$-alkylamino and di-($C_1$-$C_4$-alkyl)-amino; and a 5- or 6-membered heteroaromatic ring having 1, 2 or 3 heteroatoms selected from O, N and S are ring members;

$R^{2a}$ and $R^{2d}$ are hydrogen; and $R^{2b}$ and $R^{2c}$ are $C_1$-$C_4$-alkoxy; or $R^{2a}$ and $R^{2b}$ form together a bridging group —CH═CH—CH═CH— or —O—$CH_2$—O—; and $R^{2c}$ and $R^{2d}$ form together a bridging group —CH═CH—CH═CH— or —O—$CH_2$—O—;

in L.12:

each $R^1$ is independently phenyl which may carry 1, 2 or 3 substituents selected from the group consisting of $C_1$-$C_4$-alkyl and $C_1$-$C_4$-alkoxy;

in L.13:

each $R^{1a}$ is independently $C_1$-$C_6$-alkyl;

each $R^{1b}$ is independently $C_1$-$C_6$-alkyl;

where $R^{1a}$ and $R^{1b}$ bound on the same P atom are not identical;

in L.14.1 and L.14.2:

$R^1$ is phenyl;

in L.15:

each $R^1$ is independently phenyl which may carry 1, 2 or 3 substituents selected from the group consisting of $C_1$-$C_4$-alkyl and $C_1$-$C_4$-alkoxy;

each $R^5$ is independently H or methyl; and n is 0, 1 or 2.

When in L.11 $R^{2a}$ and $R^{2b}$ or $R^{2c}$ and $R^{2d}$ form together a bridging group, this results in a condensed ring system. If $R^{2a}$ and $R^{2b}$ or $R^{2c}$ and $R^{2d}$ form together a bridging group —CH═CH—CH═CH—, the resulting ring system is a naphthyl ring. If $R^{2a}$ and $R^{2b}$ as well as $R^{2c}$ and $R^{2d}$ form respectively a bridging group —CH═CH—CH═CH—, the overall resulting system is a binaphthyl(carrying in 2- and 2'-positions a $P(R^1)_2$ group). If $R^{2a}$ and $R^{2b}$ or $R^{2c}$ and $R^{2d}$ form together a bridging group —O—$CH_2$—O—, the resulting ring system is a 1,3-benzodioxole ring. If $R^{2a}$ and $R^{2b}$ as well as $R^{2c}$ and $R^{2d}$ form respectively a bridging group —O—$CH_2$—O—, the overall resulting system is a 4-(1,3-benzodioxol-4-yl)-1,3-benzodioxole (carrying in the respective 5-positions a $P(R^1)_2$ group).

Specifically, the chiral forms of the ligands of formulae L.1, L.2, L.3, L.4, L.5, L.10 or L.11 are used.

Such ligands are principally known in the art and generally commercially available. If not commercially available, they can be prepared in analogy to methods used for preparing the commercial products.

Ligands L.1 are known as Josiphos ligands. Ligands L.2 are known an JoSPOphos ligands. Ligands L.3 are known as Taniaphos ligands. Ligands L.4 are known as Wal-phos ligands. Ligands L.5 are known as POx ligands. Ligands L.6 are known as Man-dyphos ligands.

The ferrocenyl-containing ligands L.1 to L.10 show at least planar chirality at the ferrocenyl system. Moreover, L.1 to L.4 and L.6 to L.10 contain at least one stereogenic center (asymmetric carbon atom) (in L.1 to L.4 and L.6 to L.8 the carbon atom via which the "right" substituent (as shown above) is bound to the upper cyclopentadienyl ring; in L.9 and L.10 the carbon atom carrying the methyl group and $NR^3R^4$). L.6 and L.10 contain a further stereogenic center (asymmetric carbon atom). In L.2, the phosphorus atom in the P(═O)(H)$R^1$ substituent is a further stereogenic center. In L.5, the carbon atom carrying the $R^2$ radical is a stereogenic center. If in groups $P(R^1)_2$ and $P(R^2)_2$ the two $R^1$ or $R^2$ radicals are not identical, the phosphorus atom is principally also a stereogenic center. However, if the two $R^1$ or $R^2$ radicals are not bulky, the swinging of the free electron pair is generally too fast and does not allow a distinction of the two isomers at this stereogenic center. L.11, L.13 and L.14 show planar chirality, and L.12 and L.15 have stereogenic centers (asymmetric carbon atoms). The elements of chirality will become more evident in the following display:

Preferably, the chiral ligands are selected from the group consisting of the ligands of formulae L.1.1 to L.15.2:

L.1.1

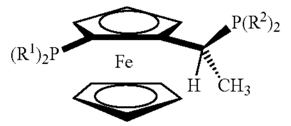

L.1.2

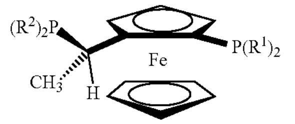

L.1.3

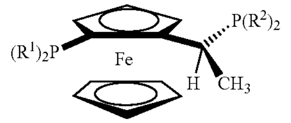

L.1.4

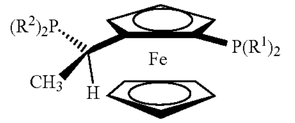

L.2.1

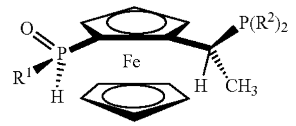

L.2.2

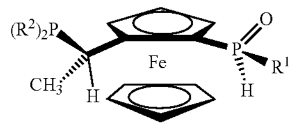

L.2.3

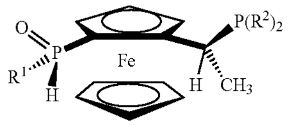

L.2.4

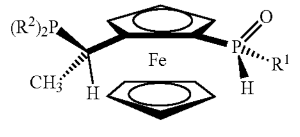

-continued
L.2.5
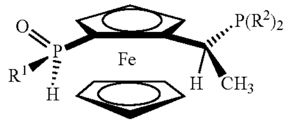
L.2.6
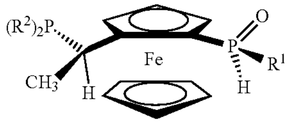
L.2.7
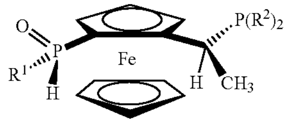
L.2.8
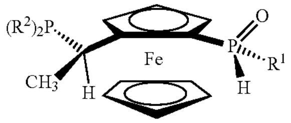
L.3.1
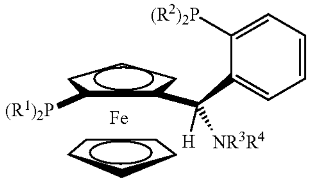
L.3.2
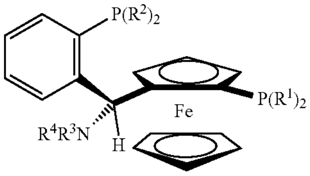
L.3.3
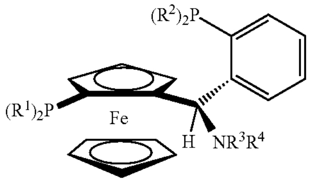
L.3.4
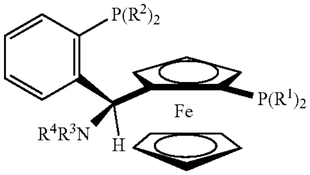
L.4.1
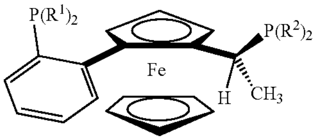
L.4.2
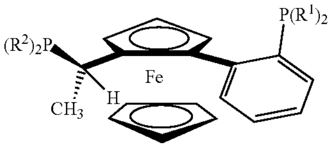
-continued
L.4.3
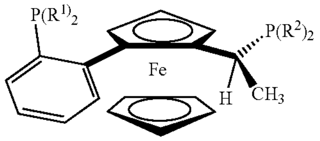
L.4.4
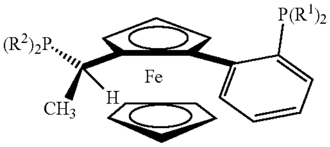
L.5.1
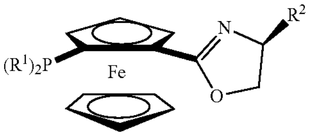
L.5.2
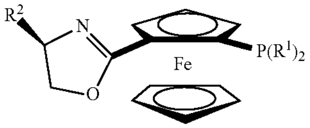
L.5.3
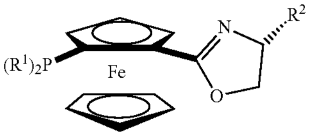
L.5.4
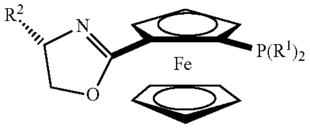
L.6.1
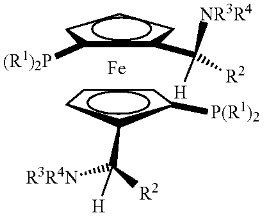
L.6.2
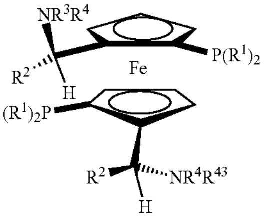
L.6.3
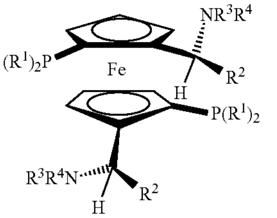

-continued
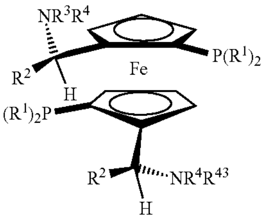
L.6.4
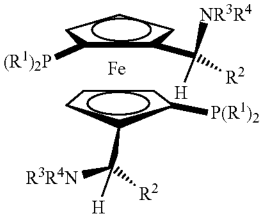
L.6.5
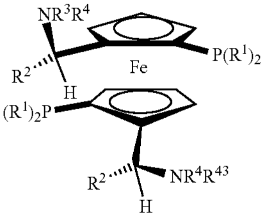
L.6.6
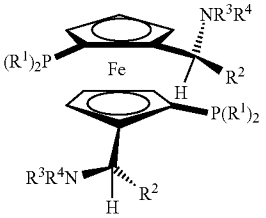
L.6.7
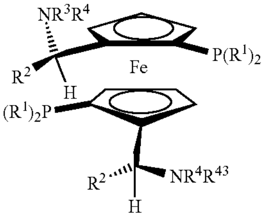
L.6.8
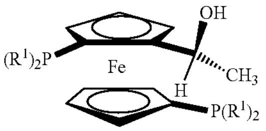
L.7.1
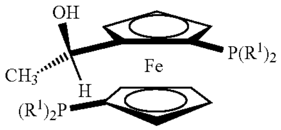
L.7.2
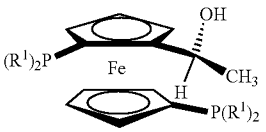
L.7.3
-continued
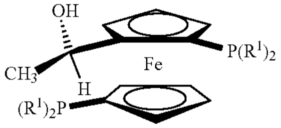
L.7.4
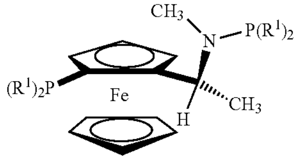
L.8.1
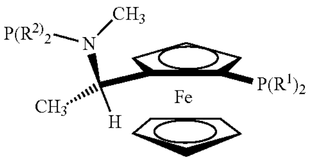
L.8.2
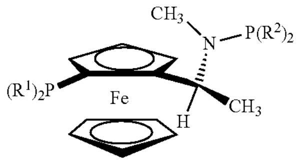
L.8.3
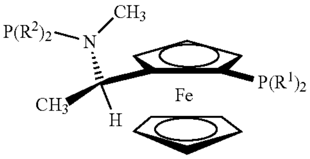
L.8.4
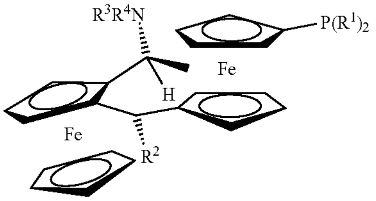
L.9.1
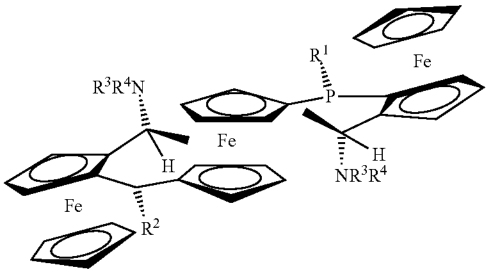
L.10.1
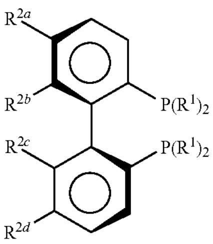
L.11.1

-continued

L.11.2

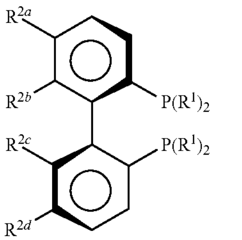

L.12.1

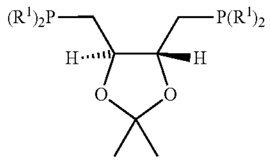

L.12.2

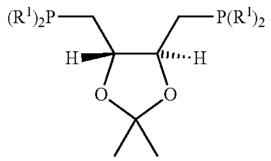

L.13.1

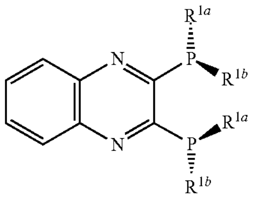

L.13.2

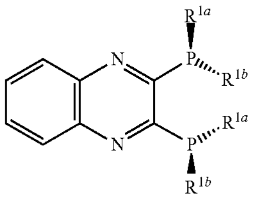

L.14.1

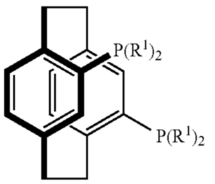

L.14.2

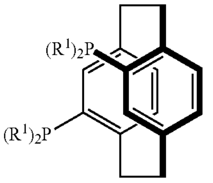

L.15.1

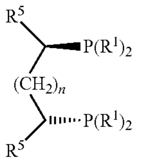

-continued

L.15.2

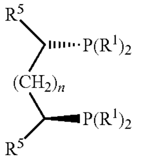

where $R^1$, $R^2$, $R^3$, $R^4$, $R^5$ and n are as defined above.

Preferably, however:

in L.1.1, L.1.2, L.1.3 and L.1.4:

the two radicals $R^1$ are identical and selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl; and the two radicals $R^2$ are identical and selected from the group consisting of $C_1$-$C_6$-alkyl, $C_3$-$C_6$-cycloalkyl, phenyl and naphthyl, where phenyl and naphthyl may carry 1, 2 or 3 substituents selected from the group consisting of $C_1$-$C_4$-alkyl and $C_1$-$C_4$-haloalkyl;

in L.2.1, L.2.2, L.2.3, L.2.4, L.2.5, L.2.6, L.2.7 and L.2.8:

$R^1$ is selected from the group consisting of $C_1$-$C_6$-alkyl and phenyl which may carry 1, 2 or 3 substituents selected from the group consisting of $C_1$-$C_4$-alkyl; and the two radicals $R^2$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl;

in L.3.1, L.3.2, L.3.3 and L.3.4:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

the two radicals $R^2$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and $R^3$ and $R^4$ are methyl;

in L.4.1, L.4.2, L.4.3 and L.4.4:

the two radicals $R^1$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

the two radicals $R^2$ are identical and selected from the group consisting of $C_1$-$C_6$-alkyl, $C_3$-$C_6$-cycloalkyl and phenyl which may carry 1, 2 or 3 substituents selected from the group consisting of $C_1$-$C_4$-alkyl and $C_1$-$C_4$-haloalkyl;

in L.5.1, L.5.2, L.5.3 and L.5.4:

the two radicals $R^1$ are identical and selected from the group consisting of phenyl or naphthyl, where phenyl and naphthyl may carry 1, 2 or 3 substituents selected from the group consisting of $C_1$-$C_4$-alkyl and $C_1$-$C_4$-haloalkyl; and $R^2$ is $C_1$-$C_4$-alkyl;

in L.6.1, L.6.2, L.6.3, L.6.4, L.6.5, L.6.6, L.6.7 and L.6.8:

the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;

$R^2$ is phenyl; and $R^3$ and $R^4$ are identical and are $C_1$-$C_4$-alkyl;

in L.7.1, L.7.2, L.7.3 and L.7.4:
$R^1$ is phenyl;
in L.8.1, L.8.2, L.8.3 and L.8.4:
$R^1$ and $R^2$ are phenyl;
in L.9.1:
the two radicals $R^1$ are identical and are $C_3$-$C_6$-cycloalkyl;
$R^2$ is phenyl; and
$R^3$ and $R^4$ are identical and are $C_1$-$C_4$-alkyl;
in L.10.1:
$R^1$ and $R^2$ are phenyl; and
$R^3$ and $R^4$ are identical and are $C_1$-$C_4$-alkyl;
in L.11.1 and L.11.2:
the four radicals $R^1$ are identical and selected from the group consisting of $C_1$-$C_6$-alkyl, phenyl which may carry 1, 2 or 3 substituents selected from the group consisting of $C_1$-$C_4$-alkyl, $C_1$-$C_4$-alkoxy, amino, $C_1$-$C_4$-alkylamino and di-($C_1$-$C_4$-alkyl)-amino; and a 5- or 6-membered heteroaromatic ring having 1, 2 or 3 heteroatoms selected from O, N and S are ring members;
$R^{2a}$ and $R^{2d}$ are hydrogen; and
$R^{2b}$ and $R^{2c}$ are identical and are $C_1$-$C_4$-alkoxy; or
$R^{2a}$ and $R^{2b}$ form together a bridging group —CH═CH—CH═CH—; and simultaneously $R^{2c}$ and $R^{2d}$ form together a bridging group —CH═CH—CH═CH—; or
$R^{2a}$ and $R^{2b}$ form together a bridging group —O—$CH_2$—O—; and simultaneously $R^{2c}$ and $R^{2d}$ form together a bridging group —O—$CH_2$—O—;
in L.12.1 and L.12.2:
the four radicals $R^1$ are identical and are phenyl which may carry 1, 2 or 3 substituents selected from the group consisting of $C_1$-$C_4$-alkyl and $C_1$-$C_4$-alkoxy;
in L.13.1 and L.13.2:
the two radicals $R^{1a}$ are identical and are $C_1$-$C_6$-alkyl;
the two radicals $R^{1b}$ are identical and are $C_1$-$C_6$-alkyl;
where $R^{1a}$ and $R^{1b}$ bound on the same P atom are not identical;
in L.14.1 and L.14.2:
$R^1$ is phenyl;
in L.15:
the four radicals $R^1$ are identical and are phenyl which may carry 1, 2 or 3 substituents selected from the group consisting of $C_1$-$C_4$-alkyl and $C_1$-$C_4$-alkoxy;
each $R^5$ is independently H or methyl; and
n is 0, 1 or 2.
In particular:
in L.1.1, L.1.2, L.1.3 and L.1.4:
the two radicals $R^1$ are identical and selected from the group consisting of $C_3$-$C_6$-alkyl, cyclohexyl, phenyl which may carry 1, 2 or 3 substituents selected from the group consisting of $C_1$-$C_4$-alkyl and $C_1$-$C_4$-haloalkyl; and naphthyl; and
the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl and $C_1$-$C_4$-haloalkyl;
in L.2.1, L.2.2, L.2.3, L.2.4, L.2.5, L.2.6, L.2.7 and L.2.8:
$R^1$ is selected from the group consisting of $C_3$-$C_6$-alkyl and phenyl which may carry 1, 2 or 3 substituents selected from the group consisting of $C_1$-$C_4$-alkyl; and the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl;
in L.3.1, L.3.2, L.3.3 and L.3.4:
the two radicals $R^1$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy;
the two radicals $R^2$ are identical and selected from the group consisting of $C_3$-$C_6$-cycloalkyl and phenyl which may carry 1, 2 or 3 substituents selected from the group consisting of $C_1$-$C_4$-alkyl and $C_1$-$C_4$-alkoxy; and
$R^3$ and $R^4$ are methyl;
in L.4.1, L.4.2, L.4.3 and L.4.4:
the two radicals $R^1$ are identical and selected from the group consisting of $C_3$-$C_6$-alkyl, cyclohexyl and phenyl;
the two radicals $R^2$ are identical and selected from the group consisting of $C_3$-$C_6$-alkyl, cyclohexyl and phenyl which may carry 1, 2 or 3 substituents selected from the group consisting of $C_1$-$C_4$-alkyl and $C_1$-$C_4$-haloalkyl;
in L.5.1, L.5.2, L.5.3 and L.5.4:
the two radicals $R^1$ are identical and are naphthyl; and
$R^2$ is $C_3$-$C_4$-alkyl;
in L.6.1, L.6.2, L.6.3, L.6.4, L.6.5, L.6.6, L.6.7 and L.6.8:
the two radicals $R^1$ are identical and selected from the group consisting cyclohexyl and phenyl which may carry 1, 2 or 3 substituents selected from the group consisting of
$C_1$-$C_4$-alkyl and $C_1$-$C_4$-alkoxy;
$R^2$ is phenyl; and
$R^3$ and $R^4$ are identical and methyl;
in L.7.1, L.7.2, L.7.3 and L.7.4:
$R^1$ is phenyl;
in L.8.1, L.8.2, L.8.3 and L.8.4:
$R^1$ and $R^2$ are phenyl;
in L.9.1:
the two radicals $R^1$ are identical and are cyclohexyl;
$R^2$ is phenyl; and
$R^3$ and $R^4$ are methyl;
in L.10.1:
$R^1$ and $R^2$ are phenyl; and
$R^3$ and $R^4$ are methyl;
in L.11.1 and L.11.2:
the four radicals $R^1$ are identical and selected from the group consisting of $C_3$-$C_6$-alkyl, phenyl which may carry 1, 2 or 3 substituents selected from the group consisting of $C_3$-$C_4$-alkyl, $C_1$-$C_4$-alkoxy and di-($C_1$-$C_4$-alkyl)-amino; and furyl;
$R^{2a}$ and $R^{2d}$ are hydrogen; and
$R^{2b}$ and $R^{2c}$ are identical and are $C_1$-$C_4$-alkoxy; or
$R^{2a}$ and $R^{2b}$ form together a bridging group —CH═CH—CH═CH—; and simultaneously $R^{2c}$ and $R^{2d}$ form together a bridging group —CH═CH—CH═CH—; or
$R^{2a}$ and $R^{2b}$ form together a bridging group —O—$CH_2$—O—; and simultaneously $R^{2c}$ and $R^{2d}$ form together a bridging group —O—$CH_2$—O—;
in L.12.1 and L.12.2:
the four radicals $R^1$ are identical and are phenyl which may carry 1, 2 or 3 substituents selected from the group consisting of $C_1$-$C_4$-alkyl and $C_1$-$C_4$-alkoxy,
in L.13.1 and L.13.2:
the two radicals $R^{1a}$ are identical and are $C_3$-$C_6$-alkyl;
the two radicals $R^{1b}$ are identical and are $C_1$-$C_6$-alkyl;
where $R^{1a}$ and $R^{1b}$ bound on the same P atom are not identical;
in L.14.1 and L.14.2:
$R^1$ is phenyl;

in L.15:

the four radicals $R^1$ are identical and are phenyl which may carry 1, 2 or 3 substituents selected from the group consisting of $C_1$-$C_4$-alkyl and $C_1$-$C_4$-alkoxy;

each $R^5$ is independently H or methyl; and n is 0, 1 or 2.

The chiral ligands are in particular selected from the group consisting of the ligands of formulae L.1.1, L.1.2, L.2.1, L.2.2, L.2.3, L.2.4, L.3.1, L.3.2, L.3.3, L.3.4, L.4.1, L.4.2, L.5.1, L.5.2, L.6.1, L.6.2, L.7.1, L.7.2, L.8.1, L.8.2, L.9.1, L.10.1, L.11.1, L.11.2, L.12.1, L.12.2, L.13.1, L.13.2, L.14.1, L.14.2, L.15.1 and L.15.2, and specifically from the group consisting of the ligands of formulae L.2.1, L.2.3, L.3.1, L.3.2, L.3.3, L.3.4, L.4.1, L.4.2, L.5.1, L.5.2, L.10.1, L.11.1 and L.11.2.

In a preferred embodiment, the method of the invention serves for preparing 2-[(2S)-2-(2-chlorothiazol-5-yl)-2-hydroxy-ethyl]sulfanyl-6-hydroxy-3-methyl-5-phenyl-pyrimidin-4-one of the formula (I—S)

(I-S)

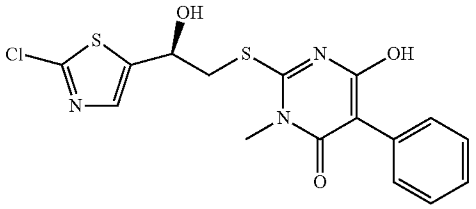

or a tautomer thereof in an enantiomeric excess of at least 50% ee, preferably at least 55% ee, more preferably at least 60% ee, even more preferably at least 70% ee, in particular at least 80% ee.

To this purpose, preferably, a chiral transition metal catalyst is used which comprises a chiral ligand selected from following ligands:

L.1.1, wherein $R^1$ and $R^2$ have the following meanings:

| No. | $R^1$ | $R^2$ |
|---|---|---|
| L.1.1.1 | phenyl | tert-butyl |
| L.1.1.2 | cyclohexyl | phenyl |
| L.1.1.3 | 3,5-di-(trifluoromethyl)-phenyl | cyclohexyl |
| L.1.1.4* | 4-(trifluoromethyl)-phenyl | tert-butyl |
| L.1.1.5 | 1-naphthyl | tert-butyl |

*with Ir

L.1.2, wherein $R^1$ and $R^2$ have the following meanings:

| No. | $R^1$ | $R^2$ |
|---|---|---|
| L.1.2.1 | 1-naphthyl | tert-butyl |
| L.1.2.2 | tert-butyl | 2-methylphenyl |
| L.1.2.3 | phenyl | tert-butyl |
| L.1.2.4 | cyclohexyl | cyclohexyl |
| L.1.2.5** | 4-(trifluoromethyl)-phenyl | tert-butyl |

**with Rh

L.2.1, wherein $R^1$ and $R^2$ have the following meanings:

| No. | $R^1$ | $R^2$ |
|---|---|---|
| L.2.1.1 | tert-butyl | phenyl |
| L.2.1.2 | phenyl | tert-butyl |
| L.2.1.3 | phenyl | phenyl |
| L.2.1.4 | tert-butyl | 3,5-dimethylphenyl |
| L.2.1.5 | tert-butyl | tert-butyl |
| L.2.1.6 | tert-butyl | cyclohexyl |

-continued

L.2.2, wherein $R^1$ and $R^2$ have the following meanings:

| No. | $R^1$ | $R^2$ |
|---|---|---|
| L.2.2.1 | tert-butyl | phenyl |

L.2.3, wherein $R^1$ and $R^2$ have the following meanings:

| No. | $R^1$ | $R^2$ |
|---|---|---|
| L.2.3.1 | tert-butyl | phenyl |
| L.2.3.2 | phenyl | phenyl |
| L.2.3.3 | tert-butyl | 3,5-dimethylphenyl |
| L.2.3.4 | tert-butyl | tert-butyl |
| L.2.3.5 | tert-butyl | cyclohexyl |

L.2.4, wherein $R^1$ and $R^2$ have the following meanings:

| No. | $R^1$ | $R^2$ |
|---|---|---|
| L.2.4.1 | phenyl | tert-butyl |

L.3.1, wherein $R^3$ and $R^4$ are methyl and $R^1$ and $R^2$ have the following meanings:

| No. | $R^1$ | $R^2$ |
|---|---|---|
| L.3.1.1 | phenyl | phenyl |
| L.3.1.2* | cyclohexyl | cyclohexyl |

*with Ir

L.3.2, wherein $R^3$ and $R^4$ are methyl and $R^1$ and $R^2$ have the following meanings:

| No. | $R^1$ | $R^2$ |
|---|---|---|
| L.3.2.1** | cyclohexyl | cyclohexyl |

**with Rh

L.3.4, wherein $R^3$ and $R^4$ are methyl and $R^1$ and $R^2$ have the following meanings:

| No. | $R^1$ | $R^2$ |
|---|---|---|
| L.3.4.1 | 3,5-dimethyl-4-methoxyphenyl | 3,5-dimethyl-4-methoxyphenyl |

L.4.1, wherein $R^1$ and $R^2$ have the following meanings:

| No. | $R^1$ | $R^2$ |
|---|---|---|
| L.4.1.1 | phenyl | tert-butyl |
| L.4.1.2 | tert-butyl | tert-butyl |
| L.4.1.3 | cyclohexyl | 3,5-di-(trifluoromethyl)-phenyl |

L.4.2, wherein $R^1$ and $R^2$ have the following meanings:

| No. | $R^1$ | $R^2$ |
|---|---|---|
| L.4.2.1 | phenyl | cyclohexyl |

L.5.2, wherein $R^1$ and $R^2$ have the following meanings:

| No. | $R^1$ | $R^2$ |
|---|---|---|
| L.5.2.1 | 1-naphthyl | isopropyl |

L.6.1, wherein $R^3$ and $R^4$ are methyl and $R^1$ and $R^2$ have the following meanings:

| No. | $R^1$ | $R^2$ |
|---|---|---|
| L.6.1.1 | cyclohexyl | phenyl |
| L.6.1.2 | 3,5-dimethyl-4-methoxyphenyl | phenyl |

L.7.1, wherein $R^1$ is phenyl(ligand no. L.7.1.1)

L.8.1, wherein $R^1$ and $R^2$ are phenyl(ligand no. L.8.1.1)

L.9.1, wherein $R^1$ is cyclohexyl, $R^2$ is phenyl and $R^3$ and $R^4$ are methyl(ligand no. L.9.1.1)

L.10.1, wherein $R^1$ is phenyl, $R^2$ is phenyl and $R^3$ and $R^4$ are methyl(ligand no. L.10.1.1)

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.1 | H | $OCH_3$ | $OCH_3$ | H | 3,5-di-(tert-butyl)-4-methoxyphenyl |
| L.11.1.2* | H | $OCH_3$ | $OCH_3$ | H | 2-furyl |

*with Ru

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.2.1 | H | $OCH_3$ | $OCH_3$ | H | isopropyl |
| L.11.2.2 | H | $OCH_3$ | $OCH_3$ | H | 3,5-diisopropyl-4-(dimethylamino)-phenyl |
| L.11.2.3** | H | $OCH_3$ | $OCH_3$ | H | 2-furyl |
| L.11.2.4 | —O—$CH_2$—O— | | —O—$CH_2$—O— | | xylyl |
| L.11.2.5 | —CH═CH—CH═CH— | | —CH═CH—CH═CH— | | phenyl |

**with Ir

L.12.2, wherein $R^1$ is 3,5-dimethyl-4-methoxyphenyl(ligand no. L.12.2.1)

L.13.1, wherein $R^{1a}$ is tert-butyl and $R^{1b}$ is methyl(ligand no. L.13.1.1)

L.14.1, wherein $R^1$ is phenyl(ligand no. L.14.1.1)

L.15.2, wherein $R^1$ is phenyl, $R^5$ is methyl and n is 1 (ligand no. L.15.2.1)

It has to be noticed that in case of the preferred Rh, Ir or Ru catalysts, a few of the chiral ligands yield the desired enantiomer of compound (I) in the desired enantioselectivity if used in combination with a specific metal of the three aforementioned. This is indicated above and below by asterisks; in each case the suitable metal is compiled below the respective table. In some very rare instances, also the solvent or an anion optionally present in the catalyst complex or catalyst precursor to counterbalance the charge, if necessary, might have an influence on enantioselectivity. The vast majority of the chiral ligands are however less sensitive and work with any of the group VIII metals and especially with any of Rh, Ir and Ru ("work" meaning that the complex formed leads to the desired (I—S) enantiomer in sufficient enantioselectivity), and in most cases, solvent and anion have only minor influence on enantioselectivity. Nevertheless, also these less sensitive ligands work better with some central metals than with others.

Therefore, more preferably, for preparing compounds (I—S), the chiral transition metal catalyst comprises a chiral ligand selected from following ligands in combination with the transition metal as central metal as indicated in each case:

L.1.1, wherein $R^1$ and $R^2$ have the following meanings:

| No. | $R^1$ | $R^2$ | metal |
|---|---|---|---|
| L.1.1.1 | phenyl | tert-butyl | Ir |
| L.1.1.2 | cyclohexyl | phenyl | Ir, Rh |
| L.1.1.3 | 3,5-di-(trifluoromethyl)-phenyl | cyclohexyl | Ir, Rh |
| L.1.1.4 | 4-(trifluoromethyl)-phenyl | tert-butyl | Ir |
| L.1.1.5 | 1-naphthyl | tert-butyl | Ir |

L.1.2, wherein $R^1$ and $R^2$ have the following meanings:

| No. | $R^1$ | $R^2$ | metal |
|---|---|---|---|
| L.1.2.1 | 1-naphthyl | tert-butyl | Ir |
| L.1.2.2 | tert-butyl | 2-methylphenyl | Ir, Rh |
| L.1.2.3 | phenyl | tert-butyl | Ir, Rh |
| L.1.2.4 | cyclohexyl | cyclohexyl | Ir, Rh |
| L.1.2.5 | 4-(trifluoromethyl)-phenyl | tert-butyl | Rh |

L.2.1, wherein $R^1$ and $R^2$ have the following meanings:

| No. | $R^1$ | $R^2$ | metal |
|---|---|---|---|
| L.2.1.1 | tert-butyl | phenyl | Ir, Rh |
| L.2.1.2 | phenyl | tert-butyl | Ir, Rh |
| L.2.1.3 | phenyl | phenyl | Ir |
| L.2.1.4 | tert-butyl | 3,5-dimethylphenyl | Ir |
| L.2.1.5 | tert-butyl | tert-butyl | Ir |
| L.2.1.6 | tert-butyl | cyclohexyl | Ir |

L.2.2, wherein $R^1$ and $R^2$ have the following meanings:

| No. | $R^1$ | $R^2$ | metal |
|---|---|---|---|
| L.2.2.1 | tert-butyl | phenyl | Ir, Rh |

L.2.3, wherein $R^1$ and $R^2$ have the following meanings:

| No. | $R^1$ | $R^2$ | metal |
|---|---|---|---|
| L.2.3.1 | tert-butyl | phenyl | Ir |
| L.2.3.2 | phenyl | phenyl | Ir |
| L.2.3.3 | tert-butyl | 3,5-dimethylphenyl | Ir |
| L.2.3.4 | tert-butyl | tert-butyl | Ir |
| L.2.3.5 | tert-butyl | cyclohexyl | Ir |

L.2.4, wherein $R^1$ and $R^2$ have the following meanings:

| No. | $R^1$ | $R^2$ | metal |
|---|---|---|---|
| L.2.4.1 | phenyl | tert-butyl | Ir |

L.3.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.1.1 | phenyl | phenyl | methyl | methyl | Rh |
| L.3.1.2 | cyclohexyl | cyclohexyl | methyl | methyl | Ir |

| No. | $R^1$ | $R^2$ | $R^3$ | $R^4$ | metal |
|---|---|---|---|---|---|
| L.3.2.1 | cyclohexyl | cyclohexyl | methyl | methyl | Rh |

L.3.2, wherein $R^1$, $R^2$, $R^3$ and $R^4$ have the following meanings:

L.3.4, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.4.1 | 3,5-dimethyl-4-methoxyphenyl | 3,5-dimethyl-4-methoxyphenyl | methyl | methyl | Rh |

L.4.1, wherein $R^1$ and $R^2$ have the following meanings:

| No. | $R^1$ | $R^2$ | metal |
|---|---|---|---|
| L.4.1.1 | phenyl | tert-butyl | Rh |
| L.4.1.2 | tert-butyl | tert-butyl | Rh |
| L.4.1.3 | cyclohexyl | 3,5-di-(trifluoromethyl)-phenyl | Rh |

L.4.2, wherein $R^1$ and $R^2$ have the following meanings:

| No. | $R^1$ | $R^2$ | metal |
|---|---|---|---|
| L.4.2.1 | phenyl | cyclohexyl | Ir, Rh |

L.5.2, wherein $R^1$ and $R^2$ have the following meanings:

| No. | $R^1$ | $R^2$ | metal |
|---|---|---|---|
| L.5.2.1 | 1-naphthyl | isopropyl | Ir |

L.6.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.6.1.1 | cyclohexyl | phenyl | methyl | methyl | Rh |
| L.6.1.2 | 3,5-dimethyl-4-methoxyphenyl | phenyl | methyl | methyl | Rh |

L.7.1, wherein $R^1$ is phenyl(ligand no. L.7.1.1); metal=Ir

L.8.1, wherein $R^1$ and $R^2$ are phenyl(ligand no. L.8.1.1); metal=Ir, Rh

L.9.1, wherein $R^1$ is cyclohexyl, $R^2$ is phenyl and $R^3$ and $R^4$ are methyl(ligand no. L.9.1.1); metal=Ir, Rh L.10.1, wherein $R^1$ is phenyl, $R^2$ is phenyl and $R^3$ and $R^4$ are methyl(ligand no. L.10.1.1); metal=Ir L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.1 | H | $OCH_3$ | $OCH_3$ | H | 3,5-di-(tert-butyl)-4-methoxyphenyl | Rh |
| L.11.1.2 | H | $OCH_3$ | $OCH_3$ | H | 2-furyl | Ru |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.2.1 | H | $OCH_3$ | $OCH_3$ | H | isopropyl | Ir, Rh |
| L.11.2.2 | H | $OCH_3$ | $OCH_3$ | H | 3,5-diisopropyl-4-(dimethylamino)-phenyl | Ir |
| L.11.2.3 | H | $OCH_3$ | $OCH_3$ | H | 2-furyl | Ir |
| L.11.2.4 | $—O—CH_2—O—$ | | $—O—CH_2—O—$ | | xylyl | Ir |
| L.11.2.5 | —CH═CH—CH═CH— | | —CH═CH—CH═CH— | | phenyl | Ir |

L.12.2, wherein $R^1$ is 3,5-dimethyl-4-methoxyphenyl(ligand no. L.12.2.1); metal=Ir L.13.1, wherein $R^{1a}$ is tert-butyl and $R^{1b}$ is methyl(ligand no. L.13.1.1); metal=Ir L.14.1, wherein $R^1$ is phenyl(ligand no. L.14.1.1); metal=Ir, Rh L.15.2, wherein $R^1$ is phenyl, $R^5$ is methyl and n is 1 (ligand no. L.15.2.1); metal=Ir More preferably, the chiral ligand is selected from following ligands:

L.2.1, wherein $R^1$ and $R^2$ have the following meanings:

| No. | $R^1$ | $R^2$ |
|---|---|---|
| L.2.1.2 | phenyl | tert-butyl |

L.3.1, wherein $R^3$ and $R^4$ are methyl and $R^1$ and $R^2$ have the following meanings:

| No. | $R^1$ | $R^2$ |
|---|---|---|
| L.3.1.1 | phenyl | phenyl |

L.4.1, wherein $R^1$ and $R^2$ have the following meanings:

| No. | $R^1$ | $R^2$ |
|---|---|---|
| L.4.1.2 | tert-butyl | tert-butyl |

L.10.1, wherein $R^1$ is phenyl, $R^2$ is phenyl and $R^3$ and $R^4$ are methyl(ligand no. L.10.1.1)

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.1 | H | $OCH_3$ | $OCH_3$ | H | 3,5-di-(tert-butyl)-4-methoxyphenyl |

Particular preference is given to L.2.1.2. This ligand is R,S(p),R(SPO)-1-phenyl-phosphinoyl)-2-[1-(di-t-butylphosphino)ethyl]ferrocene (S(p)=S planar chirality of the ferrocenyl system; R(SPO)=R chirality at the secondary phosphine oxide (i.e. at the P atom of the P(=O) group).

Even more preferably, for preparing compounds (I—S), the chiral transition metal catalyst comprises a chiral ligand selected from following ligands in combination with the transition metal as central metal as indicated in each case:

L.2.1, wherein $R^1$ and $R^2$ have the following meanings:

| No. | $R^1$ | $R^2$ | metal |
|---|---|---|---|
| L.2.1.2 | phenyl | tert-butyl | Ir |

L.3.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.1.1 | phenyl | phenyl | methyl | methyl | Rh |

L.4.1, wherein $R^1$ and $R^2$ have the following meanings:

| No. | $R^1$ | $R^2$ | metal |
|---|---|---|---|
| L.4.1.2 | tert-butyl | tert-butyl | Rh |

L.10.1, wherein $R^1$ is phenyl, $R^2$ is phenyl and $R^3$ and $R^4$ are methyl(ligand no. L.10.1.1); metal=Ir L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.1 | H | $OCH_3$ | $OCH_3$ | H | 3,5-di-(tert-butyl)-4-methoxyphenyl | Rh |

Particularly preferably, for preparing compounds (I—S), the chiral transition metal catalyst comprises L.2.1.2 as chiral ligand coordinated to Ir as central metal.

In an alternatively preferred embodiment, the method of the invention serves for preparing 2-[(2R)-2-(2-chlorothiazol-5-yl)-2-hydroxy-ethyl]sulfanyl-6-hydroxy-3-methyl-5-phenyl-pyrimidin-4-one of the formula (I-R)

(I-R)

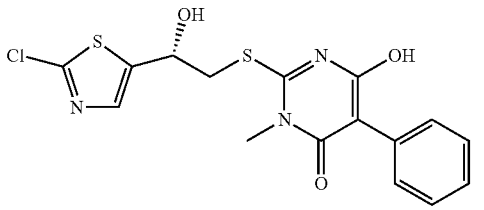

or a tautomer thereof in an enantiomeric excess of at least 50% ee, preferably at least 55% ee, more preferably at least 60% ee, even more preferably at least 70% ee, in particular at least 80% ee.

To this purpose, preferably, a chiral transition metal catalyst is used which comprises a chiral ligand selected from following ligands:

L.1.1, wherein $R^1$ and $R^2$ have the following meanings:

| No. | $R^1$ | $R^2$ |
|---|---|---|
| L.1.1.5 | 1-naphthyl | tert-butyl |
| L.1.1.6 | tert-butyl | 2-methylphenyl |
| L.1.1.1 | phenyl | tert-butyl |
| L.1.1.7 | cyclohexyl | cyclohexyl |
| L.1.1.4* | 4-(trifluoromethyl)-phenyl | tert-butyl |

*with Rh

L.1.2, wherein $R^1$ and $R^2$ have the following meanings:

| No. | $R^1$ | $R^2$ |
|---|---|---|
| L.1.2.3 | phenyl | tert-butyl |
| L.1.2.6 | cyclohexyl | phenyl |
| L.1.2.7 | 3,5-di-(trifluoromethyl)-phenyl | cyclohexyl |
| L.1.2.5** | 4-(trifluoromethyl)-phenyl | tert-butyl |
| L.1.2.1 | 1-naphthyl | tert-butyl |

**with Ir

L.2.1, wherein $R^1$ and $R^2$ have the following meanings:

| No. | $R^1$ | $R^2$ |
|---|---|---|
| L.2.1.1 | tert-butyl | phenyl |

L.2.2, wherein $R^1$ and $R^2$ have the following meanings:

| No. | $R^1$ | $R^2$ |
|---|---|---|
| L.2.2.1 | tert-butyl | phenyl |
| L.2.2.2 | phenyl | tert-butyl |
| L.2.2.3 | phenyl | phenyl |
| L.2.2.4 | tert-butyl | 3,5-dimethylphenyl |
| L.2.2.5 | tert-butyl | tert-butyl |
| L.2.2.6 | tert-butyl | cyclohexyl |

L.2.3, wherein $R^1$ and $R^2$ have the following meanings:

| No. | $R^1$ | $R^2$ |
|---|---|---|
| L.2.3.6 | phenyl | tert-butyl |
| L.2.3.1 | tert-butyl | phenyl |

L.2.4, wherein $R^1$ and $R^2$ have the following meanings:

| No. | $R^1$ | $R^2$ |
|---|---|---|
| L.2.4.2 | tert-butyl | phenyl |
| L.2.4.3 | phenyl | phenyl |
| L.2.4.4 | tert-butyl | 3,5-dimethylphenyl |
| L.2.4.5 | tert-butyl | tert-butyl |
| L.2.4.6 | tert-butyl | cyclohexyl |

L.3.1, wherein $R^3$ and $R^4$ are methyl and $R^1$ and $R^2$ have the following meanings:

| No. | $R^1$ | $R^2$ |
|---|---|---|
| L.3.1.2* | cyclohexyl | cyclohexyl |

*with Rh

L.3.2, wherein $R^3$ and $R^4$ are methyl and $R^1$ and $R^2$ have the following meanings:

| No. | $R^1$ | $R^2$ |
|---|---|---|
| L.3.2.2 | phenyl | phenyl |
| L.3.2.1** | cyclohexyl | cyclohexyl |

**with Ir

L.3.3, wherein $R^3$ and $R^4$ are methyl and $R^1$ and $R^2$ have the following meanings:

| No. | $R^1$ | $R^2$ |
|---|---|---|
| L.3.3.1 | 3,5-dimethyl-4-methoxyphenyl | 3,5-dimethyl-4-methoxyphenyl |

L.4.1, wherein $R^1$ and $R^2$ have the following meanings:

| No. | $R^1$ | $R^2$ |
|---|---|---|
| L.4.1.4 | phenyl | cyclohexyl |

L.4.2, wherein $R^1$ and $R^2$ have the following meanings:

| No. | $R^1$ | $R^2$ |
|---|---|---|
| L.4.2.2 | phenyl | tert-butyl |
| L.4.2.3 | tert-butyl | tert-butyl |
| L.4.2.4 | cyclohexyl | 3,5-di-(trifluoromethyl)-phenyl |

L.5.1, wherein $R^1$ and $R^2$ have the following meanings:

| No. | $R^1$ | $R^2$ |
|---|---|---|
| L.5.1.1 | 1-naphthyl | isopropyl |

L.6.2, wherein $R^3$ and $R^4$ are methyl and $R^1$ and $R^2$ have the following meanings:

| No. | $R^1$ | $R^2$ |
|---|---|---|
| L.6.2.1 | cyclohexyl | phenyl |
| L.6.2.2 | 3,5-dimethyl-4-methoxyphenyl | phenyl |

L.7.2, wherein $R^1$ is phenyl(ligand no. L.7.2.1)

L.8.2, wherein $R^1$ and $R^2$ are phenyl(ligand no. L.8.2.1)

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.3 | H | $OCH_3$ | $OCH_3$ | H | isopropyl |
| L.11.1.4 | H | $OCH_3$ | $OCH_3$ | H | 3,5-diisopropyl-4-(dimethylamino)-phenyl |
| L.11.1.2* | H | $OCH_3$ | $OCH_3$ | H | 2-furyl |
| L.11.1.5 | —O—$CH_2$—O— | | —O—$CH_2$—O— | | xylyl |
| L.11.1.6 | —CH═CH—CH═CH— | | —CH═CH—CH═CH— | | phenyl |

*with Ir

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.2.6 | H | $OCH_3$ | $OCH_3$ | H | 3,5-di-(tert-butyl)-4-methoxyphenyl |
| L.11.2.3** | H | $OCH_3$ | $OCH_3$ | H | 2-furyl |

**with Ru

L.12.1, wherein $R^1$ is 3,5-dimethyl-4-methoxyphenyl(ligand no. L.12.1.1)

L.13.2, wherein $R^{1a}$ is tert-butyl and $R^{1b}$ is methyl(ligand no. L.13.2.1)

L.14.2, wherein $R^1$ is phenyl(ligand no. L.14.2.1)

L.15.1, wherein $R^1$ is phenyl, $R^5$ is methyl and n is 1 (ligand no. L.15.1.1)

L.15.2, wherein $R^1$ is phenyl, $R^5$ is methyl and n is 1 (ligand no. L.15.2.1)

Analogously to what has already been mentioned above, it has to be noticed that in case of the preferred Rh, Ir or Ru catalysts, a few of the chiral ligands yield the desired enantiomer of compound (I) in the desired enantioselectivity if used in combination with a specific metal of the three aforementioned. This is indicated above and below by asterisks; in each case the suitable metal is compiled below the respective table. In some very rare instances, also the solvent or an anion optionally present in the catalyst complex or catalyst precursor to counterbalance the charge, if necessary, might have an influence on enantioselectivity. The vast majority of the ligands are however less sensitive and work with any of the group VIII metals and especially with any of Rh, Ir and Ru ("work" meaning that the complex formed leads to the desired (I-R) enantiomer in sufficient enantioselectivity), and in most cases, solvent and anion have only minor influence on enantioselectivity. Nevertheless, also these less sensitive ligands work better with some central metals than with others.

Therefore, more preferably, for preparing compounds (I-R), the chiral transition metal catalyst comprises a chiral ligand selected from following ligands in combination with the transition metal as central metal as indicated in each case:

L.1.1, wherein $R^1$ and $R^2$ have the following meanings:

| No. | $R^1$ | $R^2$ | metal |
|---|---|---|---|
| L.1.1.5 | 1-naphthyl | tert-butyl | Ir |
| L.1.1.6 | tert-butyl | 2-methylphenyl | Ir, Rh |
| L.1.1.1 | phenyl | tert-butyl | Ir, Rh |
| L.1.1.7 | cyclohexyl | cyclohexyl | Ir, Rh |
| L.1.1.4 | 4-(trifluoromethyl)-phenyl | tert-butyl | Rh |

L.1.2, wherein $R^1$ and $R^2$ have the following meanings:

| No. | $R^1$ | $R^2$ | metal |
|---|---|---|---|
| L.1.2.3 | phenyl | tert-butyl | Ir |
| L.1.2.6 | cyclohexyl | phenyl | Ir, Rh |
| L.1.2.7 | 3,5-di-(trifluoromethyl)-phenyl | cyclohexyl | Ir, Rh |
| L.1.2.5 | 4-(trifluoromethyl)-phenyl | tert-butyl | Ir |
| L.1.2.1 | 1-naphthyl | tert-butyl | Ir |

L.2.1, wherein $R^1$ and $R^2$ have the following meanings:

| No. | $R^1$ | $R^2$ | metal |
|---|---|---|---|
| L.2.1.1 | tert-butyl | phenyl | Ir, Rh |

L.2.2, wherein $R^1$ and $R^2$ have the following meanings:

| No. | $R^1$ | $R^2$ | metal |
|---|---|---|---|
| L.2.2.1 | tert-butyl | phenyl | Ir, Rh |
| L.2.2.2 | phenyl | tert-butyl | Ir, Rh |
| L.2.2.3 | phenyl | phenyl | Ir |
| L.2.2.4 | tert-butyl | 3,5-dimethylphenyl | Ir |
| L.2.2.5 | tert-butyl | tert-butyl | Ir |
| L.2.2.6 | tert-butyl | cyclohexyl | Ir |

L.2.3, wherein $R^1$ and $R^2$ have the following meanings:

| No. | $R^1$ | $R^2$ | metal |
|---|---|---|---|
| L.2.3.6 | phenyl | tert-butyl | Ir |
| L.2.3.1 | tert-butyl | phenyl | Ir |

L.2.4, wherein $R^1$ and $R^2$ have the following meanings:

| No. | $R^1$ | $R^2$ | metal |
|---|---|---|---|
| L.2.4.2 | tert-butyl | phenyl | Ir |
| L.2.4.3 | phenyl | phenyl | Ir |
| L.2.4.4 | tert-butyl | 3,5-dimethylphenyl | Ir |
| L.2.4.5 | tert-butyl | tert-butyl | Ir |
| L.2.4.6 | tert-butyl | cyclohexyl | Ir |

L.3.1, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.1.2 | cyclohexyl | cyclohexyl | methyl | methyl | Rh |

L.3.2, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.2.2 | phenyl | phenyl | methyl | methyl | Rh |
| L.3.2.1 | cyclohexyl | cyclohexyl | methyl | methyl | Ir |

L.3.3, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.3.1 | 3,5-dimethyl-4-methoxyphenyl | 3,5-dimethyl-4-methoxyphenyl | methyl | methyl | Rh |

L.4.1, wherein $R^1$ and $R^2$ have the following meanings:

| No. | $R^1$ | $R^2$ | metal |
|---|---|---|---|
| L.4.1.4 | phenyl | cyclohexyl | Ir, Rh |

L.4.2, wherein $R^1$ and $R^2$ have the following meanings:

| No. | $R^1$ | $R^2$ | metal |
|---|---|---|---|
| L.4.2.2 | phenyl | tert-butyl | Rh |
| L.4.2.3 | tert-butyl | tert-butyl | Rh |
| L.4.2.4 | cyclohexyl | 3,5-di-(trifluoromethyl)-phenyl | Rh |

L.5.1, wherein $R^1$ and $R^2$ have the following meanings:

| No. | $R^1$ | $R^2$ | metal |
|---|---|---|---|
| L.5.1.1 | 1-naphthyl | isopropyl | Ir |

L.6.2, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.6.2.1 | cyclohexyl | phenyl | methyl | methyl | Rh |
| L.6.2.2 | 3,5-dimethyl-4-methoxyphenyl | phenyl | methyl | methyl | Rh |

L.7.2, wherein $R^1$ is phenyl(ligand no. L.7.2.1); metal=Ir

L.8.2, wherein $R^1$ and $R^2$ are phenyl(ligand no. L.8.2.1); metal=Ir, Rh

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.3 | H | $OCH_3$ | $OCH_3$ | H | isopropyl | Ir, Rh |
| L.11.1.4 | H | $OCH_3$ | $OCH_3$ | H | 3,5-diisopropyl-4-(dimethylamino)-phenyl | Ir |
| L.11.1.2 | H | $OCH_3$ | $OCH_3$ | H | 2-furyl | Ir |
| L.11.1.5 | —O—$CH_2$—O— | | —O—$CH_2$—O— | | xylyl | Ir |
| L.11.1.6 | —CH═CH—CH═CH— | | —CH═CH—CH═CH— | | phenyl | Ir |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.2.6 | H | $OCH_3$ | $OCH_3$ | H | 3,5-di-(tert-butyl)-4-methoxyphenyl | Rh |
| L.11.2.3 | H | $OCH_3$ | $OCH_3$ | H | 2-furyl | Ru |

L.12.1, wherein $R^1$ is 3,5-dimethyl-4-methoxyphenyl(ligand no. L.12.1.1); metal=Ir L.13.2, wherein $R^{1a}$ is tert-butyl and $R^{1b}$ is methyl(ligand no. L.13.2.1); metal=Ir L.14.2, wherein $R^1$ is phenyl(ligand no. L.14.2.1); metal=Ir, Rh L.15.1, wherein $R^1$ is phenyl, $R^5$ is methyl and n is 1 (ligand no. L.15.1.1); metal=Ir L.15.2, wherein $R^1$ is phenyl, $R^5$ is methyl and n is 1 (ligand no. L.15.2.1); metal=Ir More preferably, the chiral ligand is selected from:

L.2.3, wherein $R^1$ and $R^2$ have the following meanings:

| No. | $R^1$ | $R^2$ |
|---|---|---|
| L.2.3.6 | phenyl | tert-butyl |

L.3.2, wherein $R^3$ and $R^4$ are methyl and $R^1$ and $R^2$ have the following meanings:

| No. | $R^1$ | $R^2$ |
|---|---|---|
| L.3.2.2 | phenyl | phenyl |

L.3.3, wherein $R^3$ and $R^4$ are methyl and $R^1$ and $R^2$ have the following meanings:

| No. | $R^1$ | $R^2$ |
|---|---|---|
| L.3.3.1 | 3,5-dimethyl-4-methoxyphenyl | 3,5-dimethyl-4-methoxyphenyl |

L.4.2, wherein $R^1$ and $R^2$ have the following meanings:

| No. | $R^1$ | $R^2$ |
|---|---|---|
| L.4.2.4 | cyclohexyl | 3,5-di-(trifluoromethyl)-phenyl |

L.5.1, wherein $R^1$ and $R^2$ have the following meanings:

| No. | $R^1$ | $R^2$ |
|---|---|---|
| L.5.1.1 | 1-naphthyl | isopropyl |

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.3 | H | $OCH_3$ | $OCH_3$ | H | isopropyl |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.2.3** | H | $OCH_3$ | $OCH_3$ | H | 2-furyl |

**with Ru

Even more preferably, for preparing compounds (I-R), the chiral transition metal catalyst comprises a chiral ligand selected from following ligands in combination with the transition metal as central metal as indicated in each case:

L.2.3, wherein $R^1$ and $R^2$ have the following meanings:

| No. | $R^1$ | $R^2$ | metal |
|---|---|---|---|
| L.2.3.6 | phenyl | tert-butyl | Ir |

L.3.2, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.2.2 | phenyl | phenyl | methyl | methyl | Rh |

L.3.3, wherein $R^1$, $R^2$, $R^3$ and $R^4$ have the following meanings:

| No. | $R^1$ | $R^2$ | $R^3$ | $R^4$ | metal |
|---|---|---|---|---|---|
| L.3.3.1 | 3,5-dimethyl-4-methoxyphenyl | 3,5-dimethyl-4-methoxyphenyl | methyl | methyl | Rh |

L.4.2, wherein $R^1$ and $R^2$ have the following meanings:

| No. | $R^1$ | $R^2$ | metal |
|---|---|---|---|
| L.4.2.4 | cyclohexyl | 3,5-di-(trifluoromethyl)-phenyl | Rh |

L.5.1, wherein $R^1$ and $R^2$ have the following meanings:

| No. | $R^1$ | $R^2$ | metal |
|---|---|---|---|
| L.5.1.1 | 1-naphthyl | isopropyl | Ir |

1 L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.1.3 | H | $OCH_3$ | $OCH_3$ | H | isopropyl | Ir, Rh |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ | metal |
|---|---|---|---|---|---|---|
| L.11.2.3 | H | $OCH_3$ | $OCH_3$ | H | 2-furyl | Ru |

The chiral transition metal catalyst generally contains just one bidentate phosphine ligand.

Generally, the catalysts contain one or two further ligands coordinated to the central metal. The further ligands can be selected from any of the ligands typically present in pre-catalysts, such as halogenide ligands (e.g. Cl, Br or I; among which Cl is preferred), sulfonate ligands (e.g. triflate, mesylate, tosylate or nonaflate; among which triflate is preferred), carboxylate ligands (e.g. acetate, trifluoroacetate, benzoate) or a neutral ligand, such as ethylene, COD (cycloocta-1,5-diene), NBD (norbornadiene) or an aromatic ring, such as Cp, Cp*, benzene, mesitylene or para-cymene. If the catalyst contains only neutral ligands, the positive charge has to be neutralized by a counteranion. Suitable counteranions are for example halogenides, such as $Cl^-$, $Br^-$ or $I^-$; sulfonates, such as triflate, mesylate, tosylate or nonaflate; carboxylates, such as acetate, trifluoroacetate or benzoate; or non-nucleophilic anions, such as BARF (tetrakis(3,5-bis(trifluoromethyl)phenyl)borate; also abbreviated as $BAR_F$ or $[BAr_4^F]^-$).

Catalyst precursors are generally salts of the central metal or complexes of the central metal with ligands different from the chiral ligand. In case of the preferably used catalysts with Ru, Rh or Ir as central metal, the catalyst precursor is for example a binuclear complex containing a neutral ligand and a charged ligand, such as a halogen, sulfonate hydroxyl or carboxylate ligand, e.g. $[M(COD)Cl]_2$, where M is Ru, Rh or Ir; especially Rh or Ir; or is a charged complex containing 2 neutral ligands and a counteranion, such as $[M(COD)_2]X$, where X is an anion, e.g. a halide, sulfonate, carboxylate or BARF anion. Non-exhaustive examples are $[Rh(NBD)Cl]_2$, $[Rh(NBD)Br]_2$, $[Rh(NBD)(OH)]_2$, $[Rh(NBD)OAc]_2$, $[Rh(NBD)TFA]_2$, $[Rh(NBD)(PhCOO)]_2$, $[Ir(COD)Cl]_2$, $[Rh(COD)_2]OTf$ or $[Ir(COD)_2]BARF$. OAc is acetate, TFA is trifluoroacetate, PhCOO is benzoate, and OTf is triflate. In case of the preferably used catalysts with Ru as central metal, the catalyst precursor is specifically a binuclear complex containing an aromatic ring ligand and 2 halogen ligands. Non-exhaustive examples are $[Ru(para\text{-}cymene)Cl_2]_2$, $[Ru(para\text{-}cymene)I_2]_2$ and $[Ru(mesitylene)Cl_2]_2$. Such complexes are generally commercially available or can be prepared by standard methods.

Preformed catalysts are generally prepared by mixing the catalyst precursor with the chiral ligand. The reaction is generally carried out in a solvent. The catalyst precursor and the chiral ligand are generally mixed in a molar ratio of from 2:1 to 1:2, preferably 1.5:1 to 1:1.5, in particular 1.3:1 to 1:1.3 and specifically 1:1 to 1:1.3, where the molar ratio is based on the amount of transition metal (in mol) in the catalyst precursor. The formed catalyst can either be isolated before being used in the reaction or the obtained reaction mixture can be used without isolation of the complex.

If the catalyst is formed in situ, catalyst precursor and chiral ligand come into contact with each other in the presence of at least one of the reactants, e.g. of starting compound 1 and/or hydrogen. In this case, too, the catalyst precursor and the chiral ligand are generally used in a molar ratio of from 2:1 to 1:2, preferably from 1.5:1 to 1:1.5, in particular from 1.3:1 to 1:1.3 and specifically from 1:1 to 1:1.3, where the molar ratio is based on the amount of transition metal (in mol) in the catalyst precursor.

Preferably, the catalyst is preformed. In a particular embodiment, catalyst precursor and the chiral ligand are reacted with each other and the obtained reaction mixture is used, i.e. it is brought into contact with compound 1, without isolation of the preformed catalyst. In another particular embodiment, catalyst precursor and the chiral ligand are reacted with each other and the obtained complex is isolated and if desired purified before being used in the reduction method of the present invention. Isolation can be carried out by usual means, such as simply removing the solvent, optionally after aqueous workup, or extracting the reaction mixture and then removing the solvent. Further purification can for example be carried out by (re)crystallization.

Specifically, the catalyst is obtainable by reacting one of the aforementioned ligands with $[Rh(NBD)Cl]_2$, $[Rh(NBD)Br]_2$, $[Rh(NBD)(OH)]_2$, $[Rh(NBD)OAc]_2$, $[Rh(NBD)TFA]_2$, $[Rh(NBD)(PhCOO)]_2$, $[Ir(COD)Cl]_2$, $[Rh(COD)_2]OTf$, $[Ir(COD)_2]BARF$, $[Ru(para\text{-}cymene)Cl_2]_2$, $[Ru(para\text{-}cymene)I_2]_2$ or $[Ru(mesitylene)Cl_2]_2$ in a molar ratio of from 2:1 to 1:2, preferably from 1.5:1 to 1:1.5, in particular from 1.3:1 to 1:1.3 and specifically from 1:1 to 1:1.3, where the molar ratio is based on the amount of transition metal (in mol) in the catalyst precursor.

A specifically preferred catalyst is obtainable by reacting ligand L.2.1.2 with $[Ir(COD)_2]$BARF in a molar ratio of from 2:1 to 1:2, preferably from 1.5:1 to 1:1.5, in particular from 1.3:1 to 1:1.3 and specifically from 1:1 to 1:1.3, where the molar ratio is based on the amount of transition metal (in mol) in the catalyst precursor.

The reaction is preferably carried out at a pressure of from 1 to 100 bar (100 kPa to 10 MPa), preferably from 2 to 80 bar (200 kPa to 8 MPa), in particular from 10 to 60 bar (1 to 6 MPa), specifically from 40 to 60 bar (4 to 6 MPa). The pressure is generally ex-erted by hydrogen alone, but an additional, inert, gas, such as argon, can also be used for pressure build-up. Preferably, the reaction is carried out at a hydrogen pressure of from 1 to 100 bar (100 kPa to 10 MPa), preferably from 2 to 80 bar (200 kPa to 8 MPa), in particular from 10 to 60 bar (1 to 6 MPa), specifically from 40 to 60 bar (4 to 6 MPa).

The hydrogen required for the hydrogenation may be used either in pure form or in the form of hydrogen-containing gas mixtures (such as mixtures with inert gases, e.g. with argon). As a matter of course, the gas mixtures must not comprise any gas which inter-feres negatively with the reaction. Preference is given to using hydrogen in pure form.

The reaction is carried out at a temperature of preferably from −5 to 120° C., more preferably from 10 to 80° C., and in particular from 30 to 60° C.

The reaction time depends on various factors, such as the reaction temperature, the concentration of the reactants in the reaction mixture and the like. Typically, it is in the range of from about 0 to 48 h, preferably from 1 to 24 h, in particular from 1 to 18 h, specifically from 10 to 18 h. A reaction time of "0 h" in this context means that after complete addition of all components, the reaction can be sufficiently complete to con-tinue with the isolation of the desired compound (I). This can for example be the case if the addition of the reactants has lasted rather long or if it is intended to recycle the non-reacted starting material.

The reaction is preferably carried out in the presence of a solvent. The solvent is preferably selected from the group consisting of polar aprotic solvents, polar protic solvents, $C_1$-$C_4$-alkyl acetates, chlorinated alkanes, open-chained ethers, aromatic solvents and mixtures thereof.

Polar aprotic solvents are polar solvents without a functional group from which a proton can dissociate. Examples for suitable polar aprotic solvents are amides, such as dimethylformamide (DMF), diethylformamide, dibutylformamide, and dimethylacetamide; cyclic ethers, such as tetrahydrofuran, 2-methyltetrahydrofuran, 1,3-dioxane and 1,4-dioxane; sulfoxides, such as dimethylsulfoxide (DMSO); nitriles, such as acetonitrile; lactams, such as N-methylpyrrolidone (NMP), N-(n-butyl)-pyrrolidone or N-(tert-butyl)-pyrrolidone; sulfones, such as sulfolane; carbonic acid esters, such as dimethylcarbonate, ethylenecarbonate or propylene carbonate; lactones, such as γ-butyrolactone or γ-valerolactone; ureas, such as N,N, N',N'-tetramethyl urea, N,N,N',N'-tetrabutyl urea, dimethylpropylene urea (DMPU) or 1,3-dimethyl-2-imidazolinone (DMEU; DMI); and nitro compounds, such as nitromethane.

Polar protic solvents are solvents with a functional group from which a proton can dissociate. Examples of suitable polar protic solvents are $C_1$-$C_4$-alkanols, fluorinated $C_1$-$C_4$-alkanols, glycols and mixtures thereof. $C_1$-$C_4$-Alkanols are for example methanol, ethanol, n-propanol, isopropanol, n-butanol, sec-butanol, isobutanol and tert-butanol. Fluorinated $C_1$-$C_4$-alkanols are for example 2-fluoroethanol, 3-fluoropropanol, 1-fluoropropan-2-ol, 4-fluorobutanol, 1,1-difluoroethanol, 2,2-difluoroethanol, 2,2-difluoropropanol, 3,3-difluoropropanol, 1,1-difluoropropan-2-ol, 2,2,2-trifluoroethanol, 3,3,3-trifluoropropanol, 4,4,4-trifluorobutanol and the like. Examples for glycols are ethylene glycol, diethylene glycol and triethylene glycol.

Examples for suitable $C_1$-$C_4$-alkyl acetates are methyl acetate, ethyl acetate, n-propyl acetate, isopropyl acetate and n-butyl acetate.

Examples for suitable chlorinated alkanes are dichloromethane, trichloromethane or dichloroethane.

Open-chained ethers are compounds of formula R—O—R', where R and R', independently of each other, are an aliphatic, cycloaliphatic or aromatic group. In contrast to cyclic ethers, R and R' do not form together a bridging group; i.e. the ether oxygen atom is not a ring member of a cyclic ring system. Examples are di-($C_1$-$C_4$-alkyl)-ethers, such as diethylether, dipropylether, diisopropylether, dibutylether or methyl-tert-butylether; and anisol(methoxybenzene).

Examples for suitable aromatic solvents are benzene, toluene, trifluorotoluene, the xylenes (i.e. 1,2-xylene, 1,3-xylene or 1,4-xylene), chlorobenzene, dichlorobenzene or anisol.

More preferably, the solvent is selected from the group consisting of tetrahydrofuran, 2-methyltetrahydrofuran, the dioxanes (i.e. 1,3 or 1,4-dioxane), dimethylsulfoxide (DMSO), dimethylformamide (DMF), dimethylacetamide (DMAC), $C_1$-$C_4$-alkanols, fluorinated $C_1$-$C_4$-alkanols, $C_1$-$C_4$-alkyl acetates, chlorinated $C_1$-$C_2$-alkanes, di-($C_1$-$C_4$-alkyl)-ethers, benzene, toluene, trifluorotoluene, the xylenes, chlorobenzene, dichlorobenzene, anisole and mixtures of the aforementioned solvents. Even more preferably, the solvent is selected from the group consisting of 2-methyltetrahydrofuran, 1,4-dioxane, DMSO, DMF, $C_1$-$C_3$-alkanols (i.e. methanol, ethanol, n-propanol or isopropanol), 2,2,2-trifluoroethanol, ethyl acetate, chlorinated $C_1$-$C_2$-alkanes (e.g. dichloromethane, trichloromethane or dichloroethane), di-($C_1$-$C_4$-alkyl)-ethers (e.g. diethylether, dipropylether, diisopropylether, dibutylether or methyl-tert-butylether), toluene, anisole and mixtures of the aforementioned solvents. In particular, the solvent is selected from the group consisting of 2-methyltetrahydrofuran, mixtures of 2-methyltetrahydrofuran and a $C_1$-$C_3$-alkanol; mixtures of 1,4-dioxane and a $C_1$-$C_3$-alkanol, 2,2,2-trifluoroethanol or DMSO; ethyl acetate, mixtures of ethyl acetate and a $C_1$-$C_3$-alkanol; mixtures of a di-($C_1$-$C_4$-alkyl)-ether and a $C_1$-$C_3$-alkanol; and mixtures of anisole a $C_1$-$C_3$-alkanol.

The reaction can be carried out in the presence of an additive which accelerates the reaction rate. Typical additives are organic bases, organic or inorganic Brønsted or Lewis acids, borate esters, zinc halides and zinc sulfonates.

Suitable organic bases are for example $C_1$-$C_6$-trialkylamines and basic heterocycles, such as pyridine, the picolines or the lutidines (especially 2,6-lutidine).

$C_1$-$C_6$-Trialkylamines are compounds NRR'R", where R, R' and R" are independently a $C_1$-$C_6$-trialkyl group. Suitable $C_1$-$C_6$-trialkylamines are for example trimethylamine, tripropylamine, tributylamine, diisopropylethylamine (Hünig's base)dimethylisopropyl-amine, ethyl-tert-butylamine, isopropyl-tert-butylamine and the like.

Suitable organic or inorganic Brønsted acids are for example HCl and sulfonic acids, such as methylsulfonic acid, trifluoromethylsulfonic acid and p-toluenesulfonic acid.

Suitable Lewis acids are boron halides, such as $BF_3$ or BCl3 or adducts thereof, e.g. with aliphatic or cyclic ethers, such as diethylether or tetrahydrofuran; or with phenol; aluminium halides, such as $AlCl_3$, and iron(III) halides, such as $FeCl_3$. Among these, preference is given to $BF_3$ and adducts thereof.

Suitable $BF_3$ adducts are for example adducts of $BF_3$ with diethylether (also called "$BF_3$ etherate"), tetrahydrofuran or phenol (also called "$BF_3$ phenolate").

Borate esters are the esters of boric acid ($B(OH)_3$). Suitable borate esters are for example tri-($C_1$-$C_4$-alkyl)-borate esters, i.e. compounds of formula $B(OR)_3$, where each R is independently $C_1$-$C_4$-alkyl.

Suitable zinc halides and zinc sulfonates are for example $ZnCl_2$, $ZnBr_2$, $ZnI_2$, and $Zn(OTf)_2$, where OTf is triflate.

Among the above-mentioned additives, preference is given to $C_1$-$C_6$-trialkylamines, $BF_3$ and adducts thereof, borate esters, zinc halides and zinc sulfonates. More preference is given to $BF_3$ adducts, especially $BF_3$ etherate; and borate esters, such as tri-($C_1$-$C_4$-alkyl)-borate esters. Specifically, a tri-($C_1$-$C_4$-alkyl)-borate ester, such as $B(OiPr)_3$ (iPrO=isopropoxy), is used.

Preferably, the additive is used in such an amount that the molar ratio of additive and the compound 1 is in the range of from 1:100 to 10:1, in particular from 1:10 to 5:1, specifically from 1:10 to 1:1.

The reaction is generally carried out by mixing the starting compound 1, the chiral catalyst (either in preformed form or in form of a catalyst precursor and a chiral ligand), optionally the solvent and optionally the additive at the desired reaction temperature and introducing hydrogen, or mixing the components, introducing hydrogen, and bringing then the temperature to the desired range. The order of addition is not particularly criti-cal.

For instance, (i) the starting compound 1 is dissolved in a solvent, the catalyst (or catalyst precursor and ligand, if the catalyst is to be prepared in situ), optionally dissolved in a solvent, is added, and hydrogen is inserted; or (ii) the starting compound 1, optionally dissolved in a solvent, is added to the catalyst (or a mixture of catalyst precursor and ligand, if the catalyst is to be prepared in situ) dissolved in a solvent, and hydrogen is inserted.

For the reaction under pressure, customary pressure vessels known in the art, such as autoclaves, stirred autoclaves or pressure reactors, may be used. When the reaction is carried out at atmospheric pressure, customary prior art reaction apparatuses suitable for standard pressure can be used. Examples thereof are customary stirred tanks which may be equipped with evaporated cooling, suitable mixers, introduction devices, if appropriate heat exchanger elements and inertization devices.

After completion of the reaction and release of the pressure, the pyrimidinone of the formula (I) in enantiomerically enriched form is generally isolated from the reaction mixture. Isolation typically comprises adding water to the reaction mixture, isolating and optionally purifying the pyrimidinone of the formula (I) precipitated upon addition of water. Alternatively, and preferably, isolation comprises setting the pH of the reaction mixture acidic; removing at least a part of the solvent, if any, to obtain a concentrate; adding water and a solvent which has low or no miscibility with water to the concentrate; extracting the pyrimidinone of the formula (I) into the solvent which has low or no miscibility with water; and isolating the pyrimidinone of the formula (I) from the extract. The solvent which has low or no miscibility with water is preferably selected from the group consisting of 2-methyltetrahydrofuran, methyl acetate, ethyl acetate, isopropyl acetate, n-butyl acetate, isobutyl acetate, methylisopropyl ketone, and chlorobenzene.

The starting compound 1 is obtainable by reaction of N-methylthiourea with an alkyl 2-phenylmalonate to 6-hydroxy-3-methyl-5-phenyl-2-sulfanyl-pyrimidin-4-one or the corresponding thiolate and reaction thereof with 2-chloro-1-(2-chlorothiazol-5-yl)-ethanone to the compound 1. These reactions are described under separate cover.

N-methylthiourea and alkyl 2-phenylmalonates are commercially available. 2-Chloro-1-(2-chlorothiazol-5-yl)ethanone can be prepared, for example, as described in WO 2018/197541 or WO 2018/202654 by reaction of 2-chlorothiazole with a Grignard reagent to the corresponding chloro-(2-chlorothiazol-5-yl) magnesium species and reaction thereof with 2-chloro-N-methoxy-N-methyl-acetamide. Alternatively, the compound 3 can be prepared from thiourea according the method described by T. Chalopin et al. in Org. Biomol. Chem., 2016, 14, 3913-3925.

The present method leads to the compound (I) in high yields and stereoselectivity.

The compound (I) can be converted in just one further step into 3-(2-chlorothiazol-5-yl)-8-methyl-7-oxo-6-phenyl-2,3-dihydrothiazolo[3,2-a]pyrimidin-4-ium-5-olate, and especially into enantiomerically enriched forms thereof. For this purpose, the compound (I) is subjected to an internal cyclization by a nucleophilic attack of the unsubstituted nitrogen atom of the pyrimidine ring on the carbon atom carrying the aliphatic OH group. This reaction is described under separate cover, e.g. in PCT/EP2022/051368.

While the compound (I) can be converted in just one step into 3-(2-chlorothiazol-5-yl)-8-methyl-7-oxo-6-phenyl-2,3-dihydrothiazolo[3,2-a]pyrimidin-4-ium-5-olate and enantiomerically enriched forms thereof, it can also be first subjected to some modifications, such as etherification of the hydroxyl group on the pyrimidine ring, substitution of the Cl atom on the thiazole ring or introduction of substituents on the phenyl ring, so as to allow formation of 2,3-dihydrothiazolo[3,2-a]pyrimidinium compounds other than 3-(2-chlorothiazol-5-yl)-8-methyl-7-oxo-6-phenyl-2,3-dihydrothiazolo[3,2-a]pyrimidin-4-ium-5-olate.

The present invention is further illustrated in the following examples.

EXAMPLES

Abbreviations

TFA trifluoroacetic acid
MeCN acetonitrile
THF tetrahydrofuran
2-MeTHF 2-methyltetrahydrofuran
DMSO dimethylsulfoxide
DMF N,N-dimethylformamide
MeOH methanol
EtOAc ethyl acetate
iPrOH isopropanol
TFE trifluoroethanol
MTBE methyl-tert-butylether
DCE dichloroethane
OTf triflate ($-OS(O)_2CF_3$)
OiPr isopropoxy ($-OCH(CH_3)_2$)
t time min minute(s)
h hour(s)
rc.t. reaction time
r.t. room temperature
rt retention time Methods The compounds were characterized by coupled High Performance Liquid Chromatog-raphy/mass spectrometry (HPLC/MS), by NMR or by melting points.

Achiral HPLC for conversion and chemoselectivity:
Software: Agilent Series 1100
Column: Dr. Maisch Retrospher 100 C18, 4.6×75 mm, 3.0 µm
Eluent: A: $H_2O$ with 0.1 vol % TFA
B: MeCN with 0.1 vol % TFA

| t (min) | % B | Flow (mL/min) |
|---|---|---|
| 0 | 5 | 1 |
| 0.5 | 5 | 1 |
| 7.5 | 100 | 1 |
| 9.5 | 100 | 1 |
| 10 | 5 | 1 |
| 15 | 5 | 1 |

Detector: UV detector λ=220 nm, band width=4 nm
Inject. vol.: 2 µL
Temperature: 30° ° C.
Analysis time: 15 min
Chiral HPLC for % ee:
Software: Agilent Series 1260
Column: Chiralpak AD-RH 5 µm 150*4.6 mm from Daicel
Eluent: A: $H_2O$ with 0.1 vol % $H_3PO_4$
B: MeCN/2-Propanol (1:1)

| t (min) | % B | Flow (mL/min) |
|---|---|---|
| 0 | 30 | 0.9 |
| 10 | 50 | 0.9 |
| 15 | 100 | 0.9 |
| 20 | 100 | 0.9 |
| 20.1 | 50 | 0.9 |

Detector: UV detector =216 nm, band width=4 nm
Inject. vol.: 3 µL
Temperature: 40° C.
Analysis time: 22 min
Pressure: ca. 95 bar 1H-NMR: The signals are characterized by chemical shift (ppm) vs. tetramethylsilane, by their multiplicity and by their integral (relative number of hydrogen atoms given). The following abbreviations are used to characterize the multiplicity of the signals: m=mul-tiplet, q=quartet, t=triplet, d=doublet, s=singlet, dd=doublet of doublets.

Example 1: Preparation of 2-[(2S)-2-(2-chlorothiazol-5-yl)-2-hydroxy-ethyl]sulfanyl-6-hydroxy-3-methyl-5-phenyl-pyrimidin-4-one (I—S)

1.1 Preparation of 2-[2-(2-chlorothiazol-5-yl)-2-oxo-ethyl]sulfanyl-6-hydroxy-3-methyl-5-phenyl-pyrimidin-4-one 1

In a 20 L jacketed reactor, a solution of N-methylthiourea (778 g, 8.38 mol) and $NaOCH_3$ (1584 g, 8.79 mol, 30 wt % solution in methanol) and methanol (384 g, 12 mol) under $N_2$ was warmed to an internal temperature of 65° C. Then diethyl 2-phenylmalonate (2121 g, 8.79 mol) was dosed over 30 min, and the pump was washed with methanol (384 g, 12 mol). The reaction was then stirred for 4 h at an internal temperature of 65° C., and then for 18 h at 50° C. Over this time a suspension formed. Then a solution of 2-chloro-1-(2-chlorothiazole-5-yl)ethanone (1859 g, 9.00 mol) in ethanol (8.050 g, 175 mol) was dosed over 30 min. The reaction was stirred 75 min at 50° C., and a large precipitation of solid occurred. At this point ethanol (2.300 g, 50 mol) was added, and the stirring speed was increased. The reaction was stirred at 50° C. a further 36 h and then reaction was then cooled to 20° C. over 16 h. The formed solid was then isolated via filtration in three 4 L fritted funnels. Each filtercake was washed with 500 mL of ethanol. The filtercake was then returned to the 20 L reactor and slurried with 15 L of water at 75° C. for 1 h. The slurry was then filtered in two 4 L fritted funnels, and each filtercake washed three times with 500 mL of room temperature water, and then dried at 80° C. and 5 mbar in a vacuum drying oven. After drying 3040 g (91%) of the title compound in form of a brown solid in 99 wt % purity were isolated.

1H NMR (400 MHZ, DMSO-d6): δ=8.75 (s, 1H), 7.15-7.45 (m, 5H), 4.9 (s, 2H), 3.46 (s, 3H).

1.2 Preparation of 2-[(2S)-2-(2-chlorothiazol-5-yl)-2-hydroxy-ethyl]sulfanyl-6-hydroxy-3-methyl-5-phenyl-pyrimidin-4-one (I—S)

A catalyst solution was prepared as follows: In a 10 ml Schlenk tube, equipped with stirring bar and caped with a septum $[Ir(cod)_2]$BARF (60.5 mg, 0.048 mmol, 0.03 eq.) and R,S(p),R(SPO)-1-phenylphosphinoyl)-2-[1-(di-t-butylphosphino)ethyl]ferrocene (S(p)═S planar chirality of the ferrocenyl system; R(SPO)═R chirality at the secondary phosphine oxide (i.e. at the P atom of the P(═O) group) (27.6 mg, 0.057 mmol, 0.037 eq.; ligand L.2.1.2; commercially available) were placed. The Schlenk tube was placed under inert atmosphere by 3 cycles of vacuum/argon, 1 ml of 2-MeTHF was added and the catalyst solution was stirred for 1 h at room temperature to allow catalyst preformation. A red solution was obtained. Then, 2-[2-(2-chlorothiazol-5-yl)-2-oxo-ethyl]sulfanyl-6-hydroxy-3-methyl-5-phenyl-pyrimidin-4-one 1 (600 mg, 1.523 mmol) was weighted in a 20 ml Schlenk tube equipped with stirring bar and capped with a septum and placed under argon (3× vacuum/argon). 9.9 ml of 2-MeTHF was then added and a fine suspension was obtained. The ketone suspension was transferred to the autoclave under a counter flow of argon followed by the catalyst solution. The autoclave was closed, and placed under inert atmosphere by pressurization to 8 bar of argon and subsequent release of pressure (3 cycles), flushed with hydrogen by pressurization to 5 bar and subsequent release of pressure (3 cycles). Finally, the pressure was set to 50 bar, stirring was started and the reaction was heated to 45° C. for 16 h. An HPLC was taken after 16 h reaction time. After 16 h the hydrogen pressure was released and the reaction cooled to room temperature. The solvent was then removed in vacuo to afford 2-[(2S)-2-(2-chlorothiazol-5-yl)-2-hydroxy-ethyl]sulfanyl-6-hydroxy-3-methyl-5-phenyl-pyrimidin-4-one (I—S) as a beige solid (0.462 g, 77% yield, 85% ee). 1H NMR (400 MHZ, DMSO-d6): δ=11.15 (s, 1H), 7.7 (s, 1H), 7.18-7.47 (m, 5H), 6.5 (s, 1H), 5.2 (m, 1H), 3.72 (dd, 1H), 3.54 (dd, 1H), 3.4 (s, 3H).

Example 2: Preparation of 2-[(2S)-2-(2-chlorothiazol-5-yl)-2-hydroxy-ethyl]sulfanyl-6-hydroxy-3-methyl-5-phenyl-pyrimidin-4-one (I—S) using various reaction conditions The procedure was carried out in analogy example 1.2, using however the catalysts, solvents and reaction times compiled in table 1.

TABLE 1

| No. | cat. prec.[1] | asym. lig.[2] | solvent | rc. t. [h] | conversion [%] | selectivity [%] | (I-S) % ee |
|---|---|---|---|---|---|---|---|
| 1 | $[Ir(COD)_2]BARF$ | L.2.1.2 | 2-MeTHF | 16 | 88 | 89 | 85 |
| 2 | $[Ir(COD)_2]BARF$* | L.2.1.2* | 2-MeTHF | 41 | 98 | 92 | 85 |
| 3 | $[Ir(COD)_2]BARF$* | L.2.1.2* | 2-MeTHF/ MeOH 9:1 | 18 | 77 | 90 | 83 |
| 4[#] | $[Ir(COD)_2]BARF$* | L.2.1.2* | 2-MeTHF | 21 | 88 | 88 | 85 |
| 5 | $[Ir(COD)_2]BARF$ | L.2.1.2 | dioxane | 16 | 46 | 86 | 87 |
| 6 | $[Ir(COD)_2]BARF$* | L.2.1.2* | dioxane/ MeOH 9:1 | 18 | 70 | 91 | 85 |
| 7 | $[Ir(COD)_2]BARF$* | L.2.1.2* | dioxane/ MeOH 4:1 | 20 | 84 | 92 | 80 |
| 8 | $[Ir(COD)_2]BARF$* | L.2.1.2* | dioxane/ MeOH 1:4 | 16 | 89 | 92 | 78 |
| 9 | $[Ir(COD)_2]BARF$* | L.2.1.2* | dioxane/ iPrOH 4:1 | 16 | 84 | 92 | 80 |
| 10 | $[Ir(COD)_2]BARF$* | L.2.1.2* | dioxane/ DMSO 9:1 | 20 | 44 | 85 | 75 |
| 11 | $[Ir(COD)_2]BARF$* | L.2.1.2* | dioxane/ DMF 9:1 | 20 | 42 | 87 | 66 |
| 12 | $[Ir(COD)_2]BARF$* | L.2.1.2* | EtOAc/ MeOH 9:1 | 20 | 44 | 72 | 74 |
| 13 | $[Ir(COD)_2]BARF$* | L.2.1.2* | dioxane/ TFE 9:1 | 20 | 37 | 74 | 84 |
| 14 | $[Ir(COD)_2]BARF$* | L.2.1.2* | MTBE/ MeOH 9:1 | 21 | 24 | 57 | 78 |
| 15 | $[Ir(COD)_2]BARF$* | L.2.1.2* | anisole/ MeOH 9:1 | 21 | 33 | 65 | 73 |
| 16 | $[Rh(NBD)Cl]_2$ | L.3.1.1 | DCE/ iPrOH 3:7 | 16 | 100 | 95 | 59 |

[1]catalyst precursor
[2]asymmetric ligand
*1: 600 mg (1.52 mmol); asym. lig.:cat. prec. = 1.2:1
[#]in the presence of 0.5 eq. $B(OiPr)_3$ Example 3: Preparation of 2-[(2R)-2-(2-chlorothiazol-5-yl)-2-hydroxy-ethyl]sulfanyl-6-hydroxy-3-methyl-5-phenyl-pyrimidin-4-one (I-R) using various reaction conditions The procedure was carried out in analogy example 1.2, using however the catalysts, solvents and reaction times compiled in table 2.

TABLE 2

| No. | cat. prec.[1] | asym. lig.[2] | solvent | rc. t. [h] | conversion [%] | selectivity [%] | (I-R) % ee |
|---|---|---|---|---|---|---|---|
| 17 | $[Ir(COD)Cl]_2$ | L.2.3.6 | 2-MeTHF | 16 | 58 | 98 | 50 |
| 18 | $[Ir(COD)_2]BARF$ | L.2.3.6 | dioxane/ MeOH 4:1 | 16 | 33 | 82 | 55 |
| 19 | $[Rh(NBD)Cl]_2$ | L.3.2.2 | 2-MeTHF | 16 | 99 | 98 | 59 |

[1]catalyst precursor
[2]asymmetric ligand

Example 4: Preparation of 2-[(2S)-2-(2-chlorothiazol-5-yl)-2-hydroxy-ethyl]sulfanyl-6-hydroxy-3-methyl-5-phenyl-pyrimidin-4-one (I—S) using various reaction conditions A catalyst solution was prepared as follows: In an argon filled glove box in a 1 ml flask equipped with stirring bar, the metal precursor (1.6 μmol, 0.031 eq.) and ligand (2.0 μmol, 0.037 eq.) were placed. 400 μL of solvent were added and the catalyst solution was stirred for 1 h at room temperature to allow catalyst preformation. Then, 2-[2-(2-chlorothiazol-5-yl)-2-oxo-ethyl]sulfanyl-6-hydroxy-3-methyl-5-phenyl-pyrimidin-4-one 1 (21.3 mg, 54 μmol) was added. The flask was then capped and removed from the glovebox. The flask was transferred to the autoclave, the autoclave was closed, and placed under inert atmosphere by pressurization to 8 bar of argon and subsequent release of pressure (3 cycles), flushed with hydrogen by pressurization to 5 bar and subsequent release of pressure (3 cycles). Finally, the pressure was set to 50 bar, stirring was started and the reaction was heated to 45° C. for 16 h. An HPLC was taken after 16 h reaction time. After 16 h the hydrogen pressure was released and the reaction cooled to room temperature. The solvent was then removed in vacuo to afford 2-[(2S)-2-(2-chlorothiazol-5-yl)-2-hydroxy-ethyl]sulfanyl-6-hydroxy-3-methyl-5-phenyl-pyrimidin-4-one (I—S) as a beige solid.

TABLE 3

| No. | cat. prec.[1] | asym. lig.[2] | solvent | rc. t. [h] | conversion [%] | selectivity [%] | (I-S) % ee |
|---|---|---|---|---|---|---|---|
| 20 | $[Rh(NBD)Cl]_2$ | L.4.1.2 | 2-MeTHF | 16 | 23 | 70 | 72 |
| 21 | $[Ir(COD)Cl]_2$ | L.10.1.1 | 2-MeTHF | 16 | 16 | 30 | 53 |
| 22 | $[Rh(COD)_2]OTf$ | L.11.1.1 | DCE/ EtOH 3:7 | 16 | 29 | 14 | 93 |

[1]catalyst precursor
[2]asymmetric ligand

Example 5: Preparation of 2-[(2R)-2-(2-chlorothiazol-5-yl)-2-hydroxy-ethyl]sulfanyl-6-hydroxy-3-methyl-5-phenyl-pyrimidin-4-one (I-R) using various reaction conditions The procedure was carried out in analogy example 4, using however the catalysts, solvents and reaction times compiled in table 4.

TABLE 4

| No. | cat. prec.[1] | asym. lig.[2] | solvent | rc. t. [h] | conversion [%] | selectivity [%] | (I-R) % ee |
|---|---|---|---|---|---|---|---|
| 23 | $[Rh(NBD)Cl]_2$ | L.3.2.2 | dioxane/ iPrOH 1:4 | 16 | 99 | 98 | 60 |
| 24 | $[Rh(NBD)Cl]_2$ | L.3.2.2 | TFE | 16 | 56 | 94 | 64 |
| 25 | $[Rh(NBD)Cl]_2$ | L.3.2.2 | EtOAc | 16 | 96 | 99 | 70 |
| 26 | $[Rh(NBD)Br]_2$ | L.3.2.2 | EtOAc | 16 | 89 | 99 | 72 |
| 27 | $[Rh(NBD)Cl]_2$ | L.3.2.2 | dioxane/ iPrOH 1:4 | 16 | 100 | 99 | 61 |
| 28 | $[Rh(NBD)Cl]_2$ | L.3.3.1 | EtOAc | 16 | 100 | 96 | 67 |
| 29 | $[Rh(NBD)Cl]_2$ | L.4.2.4 | dioxane/ iPrOH 3:7 | 16 | 49 | 85 | 53 |
| 30 | $[Rh(COD)_2]OTf$ | L.4.2.4 | DCE/ EtOH 3:7 | 16 | 40 | 88 | 51 |
| 31 | $[Ir(COD)_2]BARF$ | L.5.1.1 | DCE/ EtOH 3:7 | 16 | 15 | 28 | 60 |
| 32 | $[Ir(COD)Cl]_2$ | L.11.1.3 | 2-MeTHF | 16 | 99 | 97 | 56 |
| 33 | $Rh(NBD)Cl]_2$ | L.11.1.3 | 2-MeTHF | 16 | 48 | 87 | 53 |
| 33# | $[RuI_2(p\text{-cymene})]_2$ | L.11.2.3 | DCE/ EtOH 3:7 | 16 | 19 | 49 | 100 |

[1]catalyst precursor
[2]asymmetric ligand
#in the presence of 20 mol % $BF_3$ etherate (relative to 1 mol of 1)

The invention claimed is:

1. A method for preparing an enantiomerically enriched form of 2-[2-(2-chlorothiazol-5-yl)-2-hydroxy-ethyl]sulfanyl-6-hydroxy-3-methyl-5-phenyl-pyrimidin-4-one of formula (I):

(I)

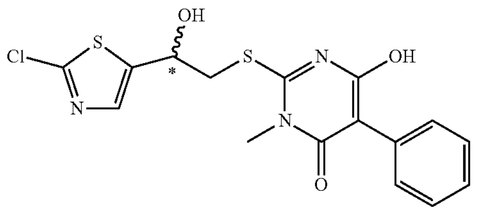

where asterisk * shows a stereogenic center; or of a tautomer thereof;

which method comprises reducing 2-[2-(2-chlorothiazol-5-yl)-2-oxo-ethyl]sulfanyl-6-hydroxy-3-methyl-5-phenyl-pyrimidin-4-one of the formula 1

1

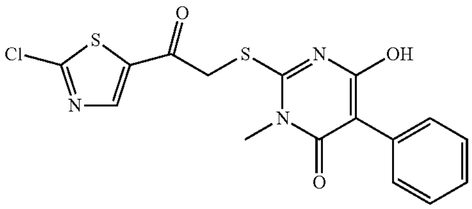

or a tautomer thereof with hydrogen in the presence of a chiral transition metal catalyst to obtain an enantiomerically enriched form of the pyrimidinone of formula (I) or a tautomer thereof.

2. The method according to claim 1, where the chiral transition metal catalyst is selected from a group VIII metal catalyst.

3. The method according to claim 2, where the chiral transition metal catalyst is selected from an Ru, Rh, and Ir catalyst.

4. The method according to claim 1, where the chiral transition metal catalyst, calculated on a basis of the transition metal content, is used in an amount of from 0.01 to 10 mol % relative to 1 mol of the compound of formula 1.

5. The method according to claim 4, where the chiral transition metal catalyst, calculated on the basis of the transition metal content, is used in an amount of from 0.1 to 5 mol-% relative to 1 mol of the compound of formula 1.

6. The method according to claim 1, where the chiral transition metal catalyst is either preformed and contains one or more chiral ligands coordinated to a transition metal; or is formed in situ by reaction of a transition metal precursor compound and one or more chiral ligands.

7. The method according to claim 1, where the chiral transition metal catalyst comprises one or more chiral ligands coordinated to a transition metal, where the chiral ligands are chiral phosphine ligands comprising one or more phosphino groups, where in case that the chiral ligands comprise just one phosphino group, they comprise additionally at least one of a phosphine oxide group, an amino group, or an imino group.

8. The method according to claim 7, where the chiral transition metal catalyst comprises one or more chiral ligands coordinated to a transition metal, where the chiral ligands are selected from the group consisting of the chiral forms of the ligands of formulae L.1 to L.15:

L.1

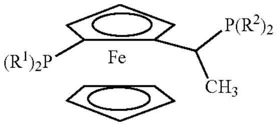

L.2

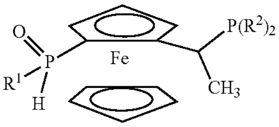

-continued

L.3

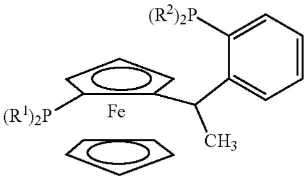

L.4

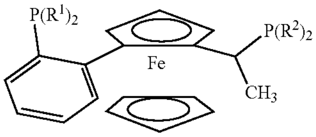

L.5

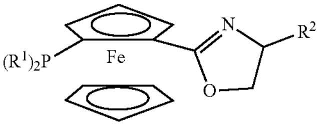

L.6

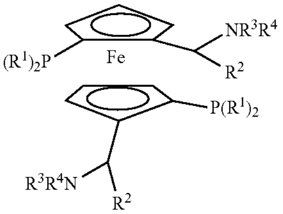

L.7

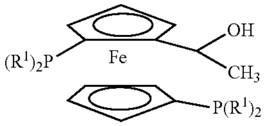

L.8

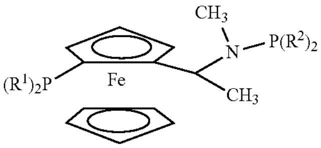

L.9

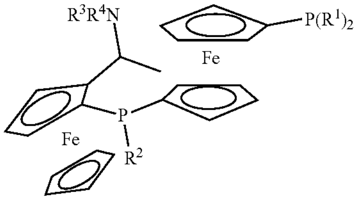

L.10

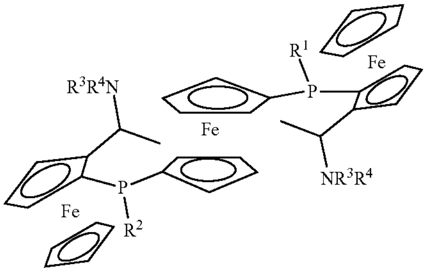

-continued

L.11

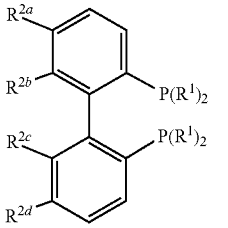

L.12

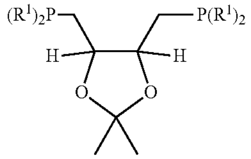

L.13

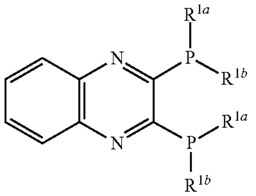

L.14.1

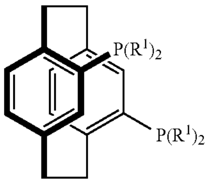

L.14.2

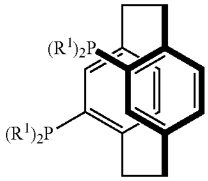

L.15

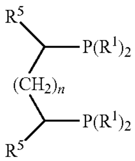

where in L.1:

$R^1$ and $R^2$, independently of each other and independently of each occurrence, are selected from the group consisting of $C_1$-$C_6$-alkyl, $C_3$-$C_6$-cycloalkyl, phenyl, and naphthyl, where phenyl and naphthyl optionally carry 1, 2, or 3 substituents selected from the group consisting of $C_1$-$C_4$-alkyl and $C_1$-$C_4$-haloalkyl;

in L.2:

$R^1$ and $R^2$, independently of each other and independently of each occurrence, are selected from the group consisting of $C_1$-$C_6$-alkyl, $C_3$-$C_6$-cycloalkyl and phenyl which optionally carry 1, 2, or 3 substituents selected from $C_1$-$C_4$-alkyl;

in L.3:

$R^1$ and $R^2$, independently of each other and independently of each occurrence, are selected from the group consisting of $C_3$-$C_6$-cycloalkyl and phenyl which optionally carry 1, 2, or 3 substituents selected from $C_1$-$C_4$-alkyl and $C_1$-$C_4$-alkoxy; and $R^3$ and $R^4$ are methyl;

in L.4:

$R^1$ and $R^2$, independently of each other and independently of each occurrence, are selected from the group consisting of $C_1$-$C_6$-alkyl, $C_3$-$C_6$-cycloalkyl, and phenyl which optionally carry 1, 2, or 3 substituents selected from the group consisting of $C_1$-$C_4$-alkyl and $C_1$-$C_4$-haloalkyl;

in L.5:

$R^1$ is phenyl or naphthyl, where phenyl and naphthyl optionally carry 1, 2, or 3 substituents selected from the group consisting of $C_1$-$C_4$-alkyl and $C_1$-$C_4$-haloalkyl; and $R^2$ is $C_1$-$C_4$-alkyl;

in L.6:

$R^1$ is selected from the group consisting of $C_3$-$C_6$-cycloalkyl and phenyl which optionally carry 1, 2, or 3 substituents selected from the group consisting of $C_1$-$C_4$-alkyl and $C_1$-$C_4$-alkoxy;

$R^2$ is phenyl; and $R^3$ and $R^4$, independently of each other, are $C_1$-$C_4$-alkyl;

in L.7:

$R^1$ is phenyl;

in L.8:

$R^1$ and $R^2$ are phenyl in L.9:

$R^1$ is $C_3$-$C_6$-cycloalkyl;

$R^2$ is phenyl; and $R^3$ and $R^4$, independently of each other, are $C_1$-$C_4$-alkyl;

in L.10:

$R^1$ and $R^2$ are phenyl; and $R^3$ and $R^4$, independently of each other, are $C_1$-$C_4$-alkyl;

in L.11:

each $R^1$ is independently selected from the group consisting of $C_1$-$C_6$-alkyl, phenyl which optionally carry 1, 2, or 3 substituents selected from the group consisting of $C_1$-$C_4$-alkyl, $C_1$-$C_4$-alkoxy, amino, $C_1$-$C_4$-alkylamino, and di-($C_1$-$C_4$-alkyl)-amino; and a 5- or 6-membered heteroaromatic ring having 1, 2, or 3 heteroatoms selected from O, N, and S are ring members;

$R^{2a}$ and $R^{2d}$ are hydrogen; and $R^{2b}$ and $R^{2c}$ are $C_1$-$C_4$-alkoxy;

or $R^{2a}$ and $R^{2b}$ form together a bridging group $—CH{=}CH—CH{=}CH—$ or $—O—CH_2—O—$; and $R^{2c}$ and $R^{2d}$ form together a bridging group $—CH{=}CH—CH{=}CH—$ or $—O—CH_2—O—$;

in L.12:

each $R^1$ is independently phenyl which optionally carry 1, 2, or 3 substituents selected from the group consisting of $C_1$-$C_4$-alkyl and $C_1$-$C_4$-alkoxy;

in L.13:

each $R^{1a}$ is independently $C_1$-$C_6$-alkyl;

each $R^{1b}$ is independently $C_1$-$C_6$-alkyl;

where $R^{1a}$ and $R^{1b}$ bound on the same P atom are not identical;

in L.14.1 and L.14.2:

$R^1$ is phenyl;

in L.15:

each $R^1$ is independently phenyl which optionally carry 1, 2, or 3 substituents selected from the group consisting of $C_1$-$C_4$-alkyl and $C_1$-$C_4$-alkoxy;

each $R^5$ is independently H or methyl; and n is 0, 1 or 2.

9. The method according to claim 8, where the chiral ligands are selected from the group consisting of the ligands of formulae L.1.1 to L.15.2:
L.1.1
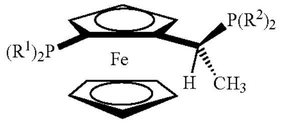
L.1.2
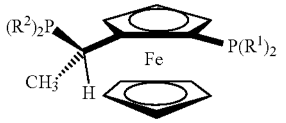
L.1.3
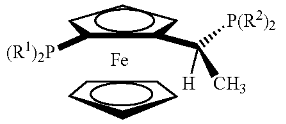
L.1.4
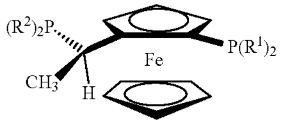
L.2.1
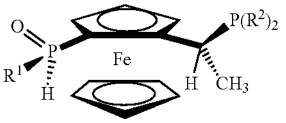
L.2.2
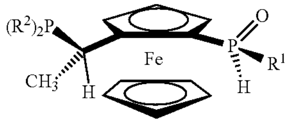
L.2.3
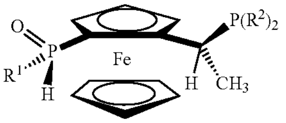
L.2.4
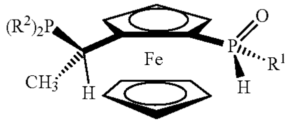
L.2.5
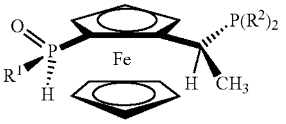
L.2.6
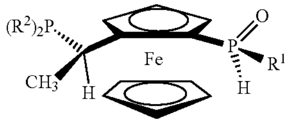
L.2.7
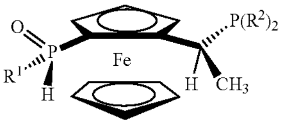
-continued
L.2.8
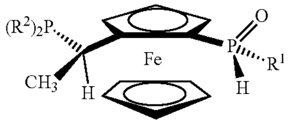
L.3.1
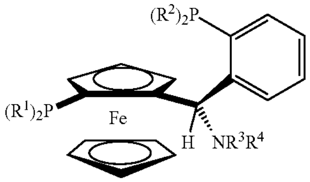
L.3.2
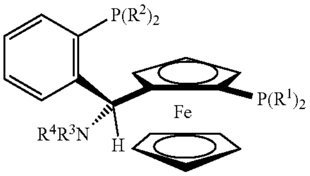
L.3.3
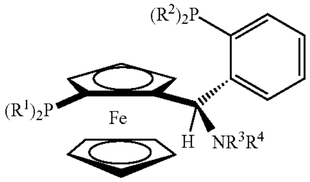
L.3.4
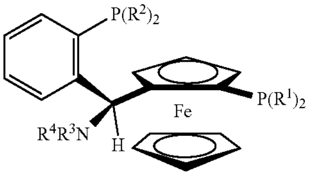
L.4.1
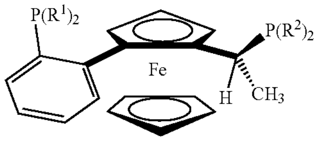
L.4.2
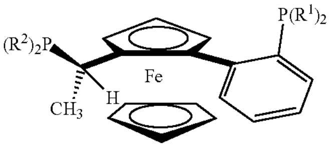
L.4.3
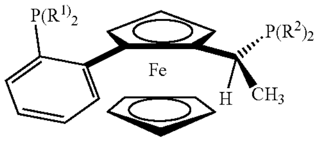
L.4.4
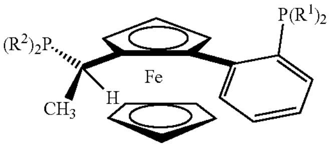

-continued
L.5.1
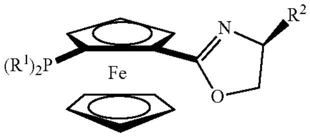
L.5.2
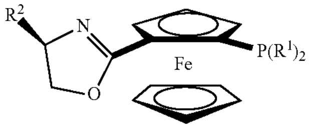
L.5.3
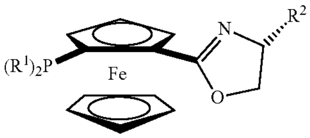
L.5.4
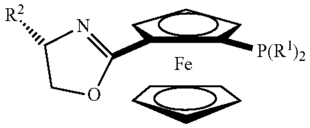
L.6.1
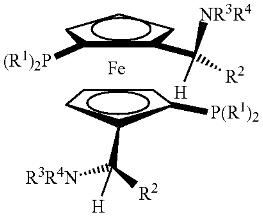
L.6.2
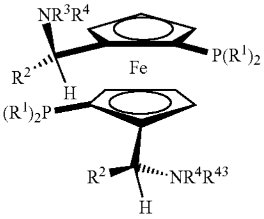
L.6.3
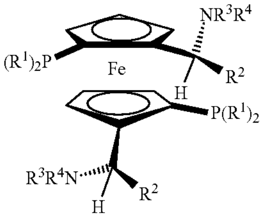
L.6.4
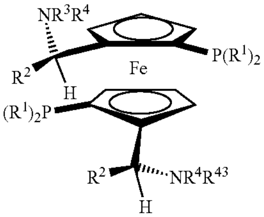
-continued
L.6.5
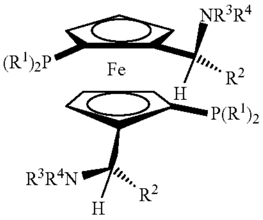
L.6.6
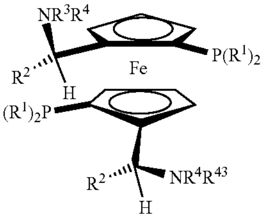
L.6.7
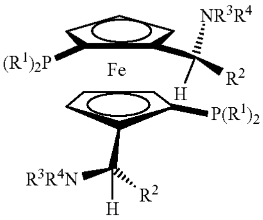
L.6.8
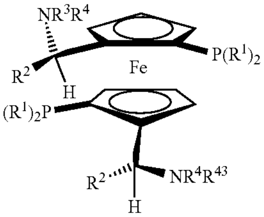
L.7.1
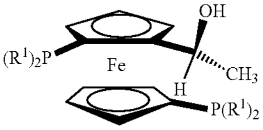
L.7.2
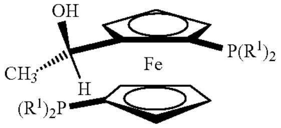
L.7.3
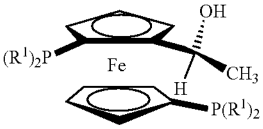
L.7.4
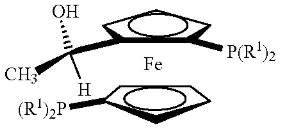

-continued
L.8.1
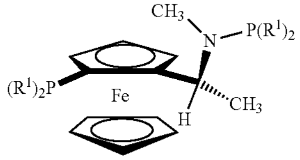
L.8.2
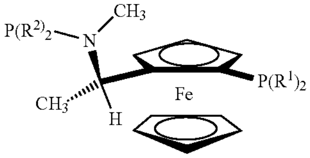
L.8.3
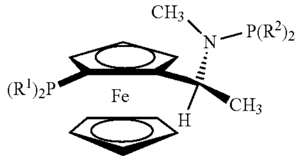
L.8.4
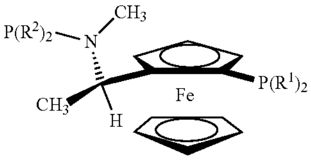
L.9.1
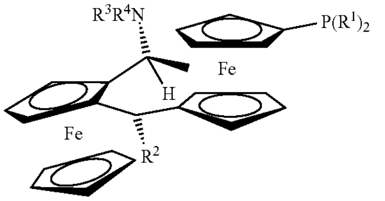
L.10.1
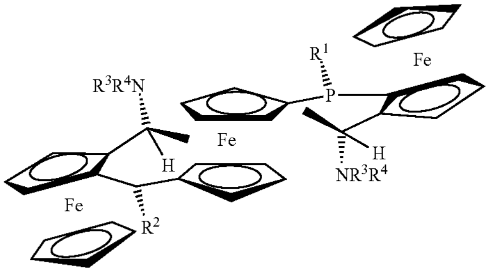
L.11.1
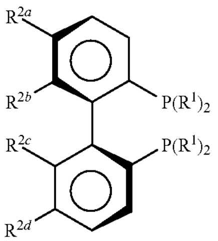
-continued
L.11.2
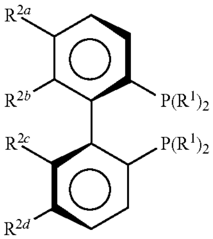
L.12.1
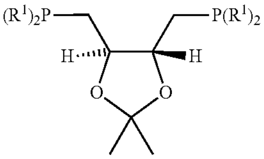
L.12.2
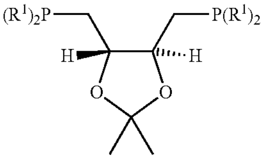
L.13.1
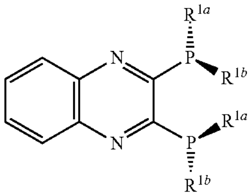
L.13.2
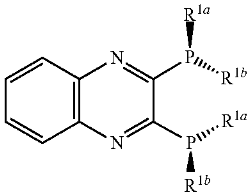
L.14.1
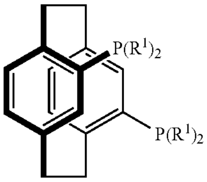
L.14.2
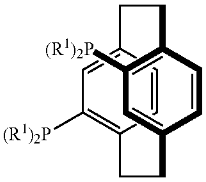
L.15.1
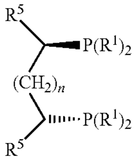

-continued

L.15.2

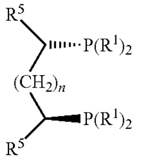

where $R^1$, $R^2$, $R^3$, $R^4$, $R^5$ and n are as defined in claim 8.

10. The method according to claim 9, where:

in L.1.1, L.1.2, L.1.3 and L.1.4:

the two radicals $R^1$ are identical and selected from the group consisting of $C_1$-$C_6$-alkyl, $C_3$-$C_6$-cycloalkyl, phenyl, and naphthyl, where phenyl and naphthyl optionally carry 1, 2, or 3 substituents selected from the group consisting of $C_1$-$C_4$-alkyl and $C_1$-$C_4$-haloalkyl; and the two radicals $R^2$ are identical and selected from the group consisting of $C_1$-$C_6$-alkyl, $C_3$-$C_6$-cycloalkyl, phenyl, and naphthyl, where phenyl and naphthyl optionally carry 1, 2, or 3 substituents selected from the group consisting of $C_1$-$C_4$-alkyl and $C_1$-$C_4$-haloalkyl;

in L.2.1, L.2.2, L.2.3, L.2.4, L.2.5, L.2.6, L.2.7 and L.2.8:

$R^1$ is selected from the group consisting of $C_1$-$C_6$-alkyl and phenyl which optionally carry 1, 2, or 3 substituents selected from $C_1$-$C_4$-alkyl; and the two radicals $R^2$ are identical and selected from the group consisting of $C_1$-$C_6$-alkyl, $C_3$-$C_6$-cycloalkyl, and phenyl which optionally carry 1, 2, or 3 substituents selected from the group consisting of $C_1$-$C_4$-alkyl;

in L.3.1, L.3.2, L.3.3 and L.3.4:

the two radicals $R^1$ are identical and selected from the group consisting of $C_3$-$C_6$-cycloalkyl and phenyl which optionally carry 1, 2, or 3 substituents selected from the group consisting of $C_1$-$C_4$-alkyl and $C_1$-$C_4$-alkoxy;

the two radicals $R^2$ are identical and selected from the group consisting of $C_3$-$C_6$-cycloalkyl and phenyl which optionally carry 1, 2, or 3 substituents selected from the group consisting of $C_1$-$C_4$-alkyl and $C_1$-$C_4$-alkoxy; and $R^3$ and $R^4$ are methyl;

in L.4.1, L.4.2, L.4.3 and L.4.4:

the two radicals $R^1$ are identical and selected from the group consisting of $C_1$-$C_6$-alkyl, $C_3$-$C_6$-cycloalkyl, and phenyl which optionally carry 1, 2, or 3 substituents selected from the group consisting of $C_1$-$C_4$-alkyl and $C_1$-$C_4$-haloalkyl;

the two radicals $R^2$ are identical and selected from the group consisting of $C_1$-$C_6$-alkyl, $C_3$-$C_6$-cycloalkyl, and phenyl which optionally carry 1, 2, or 3 substituents selected from the group consisting of $C_1$-$C_4$-alkyl and $C_1$-$C_4$-haloalkyl;

in L.5.1, L.5.2, L.5.3 and L.5.4:

the two radicals $R^1$ are identical and selected from the group consisting of phenyl or naphthyl, where phenyl and naphthyl optionally carry 1, 2, or 3 substituents selected from the group consisting of $C_1$-$C_4$-alkyl and $C_1$-$C_4$-haloalkyl; and $R^2$ is $C_1$-$C_4$-alkyl;

in L.6.1, L.6.2, L.6.3, L.6.4, L.6.5, L.6.6, L.6.7 and L.6.8:

the two radicals $R^1$ are identical and selected from the group consisting of $C_3$-$C_6$-cycloalkyl and phenyl which optionally carry 1, 2, or 3 substituents selected from the group consisting of $C_1$-$C_4$-alkyl and $C_1$-$C_4$-alkoxy;

$R^2$ is phenyl; and $R^3$ and $R^4$ are identical and are $C_1$-$C_4$-alkyl;

in L.7.1, L.7.2, L.7.3 and L.7.4:

$R^1$ is phenyl;

in L.8.1, L.8.2, L.8.3 and L.8.4

$R^1$ and $R^2$ are phenyl;

in L.9.1:

the two radicals $R^1$ are identical and are $C_3$-$C_6$-cycloalkyl;

$R^2$ is phenyl; and $R^3$ and $R^4$ are identical and are $C_1$-$C_4$-alkyl;

in L.10.1:

$R^1$ and $R^2$ are phenyl; and $R^3$ and $R^4$ are identical and are $C_1$-$C_4$-alkyl;

in L.11.1 and L.11.2:

the four radicals $R^1$ are identical and selected from the group consisting of $C_1$-$C_6$-alkyl, phenyl which optionally carry 1, 2, or 3 substituents selected from the group consisting of $C_1$-$C_4$-alkyl, $C_1$-$C_4$-alkoxy, amino, $C_1$-$C_4$-alkylamino, and di-($C_1$-$C_4$-alkyl)-amino; and a 5- or 6-membered heteroaromatic ring having 1, 2, or 3 heteroatoms selected from O, N, and S are ring members;

$R^{2a}$ and $R^{2d}$ are hydrogen; and $R^{2b}$ and $R^{2c}$ are identical and are $C_1$-$C_4$-alkoxy; or $R^{2a}$ and $R^{2b}$ form together a bridging group —CH=CH—CH=CH—; and simultaneously $R^{2c}$ and $R^{2d}$ form together a bridging group —CH=CH—CH=CH—;

or $R^{2a}$ and $R^{2b}$ form together a bridging group —O—$CH_2$—O—; and simultaneously $R^{2c}$ and $R^{2d}$ form together a bridging group —O—$CH_2$—O—;

in L.12.1 and L.12.2:

the four radicals $R^1$ are identical and are phenyl which optionally carry 1, 2, or 3 substituents selected from the group consisting of $C_1$-$C_4$-alkyl and $C_1$-$C_4$-alkoxy;

in L.13.1 and L.13.2:

the two radicals $R^{1a}$ are identical and are $C_1$-$C_6$-alkyl;

the two radicals $R^{1b}$ are identical and are $C_1$-$C_6$-alkyl;

where $R^{1a}$ and $R^{1b}$ bound on the same P atom are not identical;

in L.14.1 and L.14.2:

$R^1$ is phenyl;

in L.15:

the four radicals $R^1$ are identical and are phenyl which optionally carry 1, 2, or 3 substituents selected from the group consisting of $C_1$-$C_4$-alkyl and $C_1$-$C_4$-alkoxy;

each $R^5$ is independently H or methyl; and n is 0, 1 or 2.

11. The method according to claim 9, for preparing 2-[(2S)-2-(2-chlorothiazol-5-yl)-2-hydroxy-ethyl]sulfanyl-6-hydroxy-3-methyl-5-phenyl-pyrimidin-4-one of the formula (I-S)

(I-S)

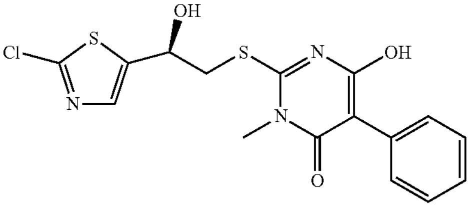

or a tautomer thereof in an enantiomeric excess of at least 50% ee, where a chiral transition metal catalyst used comprises a chiral ligand selected from following ligands:

L.1.1, wherein $R^1$ and $R^2$ have the following meanings:

| No. | $R^1$ | $R^2$ |
|---|---|---|
| L.1.1.1 | phenyl | tert-butyl |
| L.1.1.2 | cyclohexyl | phenyl |
| L.1.1.3 | 3,5-di-(trifluoromethyl)-phenyl | cyclohexyl |
| L.1.1.4 | 4-(trifluoromethyl)-phenyl | tert-butyl |
| L.1.1.5 | 1-naphthyl | tert-butyl |

L.1.2, wherein $R^1$ and $R^2$ have the following meanings:

| No. | $R^1$ | $R^2$ |
|---|---|---|
| L.1.2.1 | 1-naphthyl | tert-butyl |
| L.1.2.2 | tert-butyl | 2-methylphenyl |
| L.1.2.3 | phenyl | tert-butyl |
| L.1.2.4 | cyclohexyl | cyclohexyl |
| L.1.2.5 | 4-(trifluoromethyl)-phenyl | tert-butyl |

where in case that the chiral ligand is L.1.2.5, the transition metal of the chiral transition metal catalyst is Rh L.2.1, wherein $R^1$ and $R^2$ have the following meanings:

| No. | $R^1$ | $R^2$ |
|---|---|---|
| L.2.1.1 | tert-butyl | phenyl |
| L.2.1.2 | phenyl | tert-butyl |
| L.2.1.3 | phenyl | phenyl |
| L.2.1.4 | tert-butyl | 3,5-dimethylphenyl |
| L.2.1.5 | tert-butyl | tert-butyl |
| L.2.1.6 | tert-butyl | cyclohexyl |

L.2.2, wherein $R^1$ and $R^2$ have the following meanings:

| No. | $R^1$ | $R^2$ |
|---|---|---|
| L.2.2.1 | tert-butyl | phenyl |

L.2.3, wherein $R^1$ and $R^2$ have the following meanings:

| No. | $R^1$ | $R^2$ |
|---|---|---|
| L.2.3.1 | tert-butyl | phenyl |
| L.2.3.2 | phenyl | phenyl |
| L.2.3.3 | tert-butyl | 3,5-dimethylphenyl |
| L.2.3.4 | tert-butyl | tert-butyl |
| L.2.3.5 | tert-butyl | cyclohexyl |

L.2.4, wherein $R^1$ and $R^2$ have the following meanings:

| No. | $R^1$ | $R^2$ |
|---|---|---|
| L.2.4.1 | phenyl | tert-butyl |

L.3.1, wherein $R^3$ and $R^4$ are methyl and $R^1$ and $R^2$ have the following meanings:

| No. | $R^1$ | $R^2$ |
|---|---|---|
| L.3.1.1 | phenyl | phenyl |
| L.3.1.2 | cyclohexyl | cyclohexyl |

where in case that the chiral ligand is L.3.1.2, the transition metal of the chiral transition metal catalyst is Ir L.3.2, wherein $R^3$ and $R^4$ are methyl and $R^1$ and $R^2$ have the following meanings:

| No. | $R^1$ | $R^2$ |
|---|---|---|
| L.3.2.1 | cyclohexyl | cyclohexyl |

where in case that the chiral ligand is L.3.2.1, the transition metal of the chiral transition metal catalyst is Rh L.3.4, wherein $R^3$ and $R^4$ are methyl and $R^1$ and $R^2$ have the following meanings:

| No. | $R^1$ | $R^2$ |
|---|---|---|
| L.3.4.1 | 3,5-dimethyl-4-methoxyphenyl | 3,5-dimethyl-4-methoxyphenyl |

L.4.1, wherein $R^1$ and $R^2$ have the following meanings:

| No. | $R^1$ | $R^2$ |
|---|---|---|
| L.4.1.1 | phenyl | tert-butyl |
| L.4.1.2 | tert-butyl | tert-butyl |
| L.4.1.3 | cyclohexyl | 3,5-di-(trifluoromethyl)-phenyl |

L.4.2, wherein $R^1$ and $R^2$ have the following meanings:

| No. | $R^1$ | $R^2$ |
|---|---|---|
| L.4.2.1 | phenyl | cyclohexyl |

L.5.2, wherein $R^1$ and $R^2$ have the following meanings:

| No. | $R^1$ | $R^2$ |
|---|---|---|
| L.5.2.1 | 1-naphthyl | isopropyl |

L.6.1, wherein $R^3$ and $R^4$ are methyl and $R^1$ and $R^2$ have the following meanings:

| No. | $R^1$ | $R^2$ |
|---|---|---|
| L.6.1.1 | cyclohexyl | phenyl |
| L.6.1.2 | 3,5-dimethyl-4-methoxyphenyl | phenyl |

L.7.1, wherein $R^1$ is phenyl

L.8.1, wherein $R^1$ and $R^2$ are phenyl

L.9.1, wherein $R^1$ is cyclohexyl, $R^2$ is phenyl and $R^3$ and $R^4$ are methyl L.10.1, wherein $R^1$ is phenyl, $R^2$ is phenyl and $R^3$ and $R^4$ are methyl L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | R |
|---|---|---|---|---|---|
| L.11.1.1 | H | $OCH_3$ | $OCH_3$ | H | 3,5-di-(tert-butyl)-4-methoxyphenyl |
| L.11.1.2 | H | $OCH_3$ | $OCH_3$ | H | 2-furyl |

where in case that the chiral ligand is L.11.1.2, the transition metal of the chiral transition metal catalyst is Ru L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.2.1 | H | $OCH_3$ | $OCH_3$ | H | isopropyl |
| L.11.2.2 | H | $OCH_3$ | $OCH_3$ | H | 3,5-diisopropyl-4-(dimethylamino)-phenyl |
| L.11.2.3 | H | $OCH_3$ | $OCH_3$ | H | 2-furyl |
| L.11.2.4 | —O—$CH_2$—O— | | —O—$CH_2$—O— | | xylyl |
| L.11.2.5 | —CH═CH—CH═CH— | | —CH═CH—CH═CH— | | phenyl |

where in case that the chiral ligand is L.11.2.3, the transition metal of the chiral transition metal catalyst is Ir L.12.2, wherein $R^1$ is 3,5-dimethyl-4-methoxyphenyl L.13.1, wherein $R^{1a}$ is tert-butyl and $R^{1b}$ is methyl L.14.1, wherein $R^1$ is phenyl L.15.2, wherein $R^1$ is phenyl, $R^5$ is methyl and n is 1.

12. The method according to claim 11, where the chiral ligand is selected from following ligands:

L.2.1, wherein $R^1$ and $R^2$ have the following meanings:

| No. | $R^1$ | $R^2$ |
|---|---|---|
| L.2.1.2 | phenyl | tert-butyl |

L.3.1, wherein $R^3$ and $R^4$ are methyl and $R^1$ and $R^2$ have the following meanings:

| No. | $R^1$ | $R^2$ |
|---|---|---|
| L.3.1.1 | Phenyl | phenyl |

L.4.1, wherein $R^1$ and $R^2$ have the following meanings:

| No. | $R^1$ | $R^2$ |
|---|---|---|
| L.4.1.2 | tert-butyl | tert-butyl |

L.10.1, wherein $R^1$ is phenyl, $R^2$ is phenyl and $R^3$ and $R^4$ are methyl

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.1 | H | $OCH_3$ | $OCH_3$ | H | 3,5-di-(tert-butyl)-4-methoxyphenyl. |

13. The method according to claim 9, for preparing 2-[(2R)-2-(2-chlorothiazol-5-yl)-2-hydroxy-ethyl]sulfanyl-6-hydroxy-3-methyl-5-phenyl-pyrimidin-4-one of formula (I-R)

(I-R)

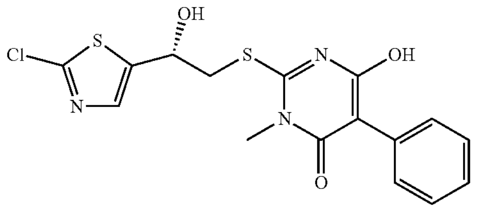

or a tautomer thereof in an enantiomeric excess of at least 50% ee, where a chiral transition metal catalyst is used which comprises a chiral ligand selected from following ligands:

L.1.1, wherein $R^1$ and $R^2$ have the following meanings:

| No. | $R^1$ | $R^2$ |
|---|---|---|
| L.1.1.5 | 1-naphthyl | tert-butyl |
| L.1.1.6 | tert-butyl | 2-methylphenyl |
| L.1.1.1 | Phenyl | tert-butyl |
| L.1.1.7 | cyclohexyl | cyclohexyl |
| L.1.1.4 | 4-(trifluoromethyl)-phenyl | tert-butyl |

where in case that the chiral ligand is L.1.1.4, the transition metal of the chiral transition metal catalyst is Rh L.1.2, wherein $R^1$ and $R^2$ have the following meanings:

| No. | $R^1$ | $R^2$ |
|---|---|---|
| L.1.2.3 | phenyl | tert-butyl |
| L.1.2.6 | cyclohexyl | phenyl |
| L.1.2.7 | 3,5-di-(trifluoromethyl)-phenyl | cyclohexyl |
| L.1.2.5 | 4-(trifluoromethyl)-phenyl | tert-butyl |
| L.1.2.1 | 1-naphthyl | tert-butyl |

where in case that the chiral ligand is L.1.2.5, the transition metal of the chiral transition metal catalyst is Ir L.2.1, wherein $R^1$ and $R^2$ have the following meanings:

| No. | $R^1$ | $R^2$ |
|---|---|---|
| L.2.1.1 | tert-butyl | phenyl |

L.2.2, wherein $R^1$ and $R^2$ have the following meanings:

| No. | $R^1$ | $R^2$ |
|---|---|---|
| L.2.2.1 | tert-butyl | phenyl |
| L.2.2.2 | phenyl | tert-butyl |
| L.2.2.3 | phenyl | phenyl |
| L.2.2.4 | tert-butyl | 3,5-dimethylphenyl |

-continued

| No. | $R^1$ | $R^2$ |
|---|---|---|
| L.2.2.5 | tert-butyl | tert-butyl |
| L.2.2.6 | tert-butyl | cyclohexyl |

L.2.3, wherein $R^1$ and $R^2$ have the following meanings:

| No. | $R^1$ | $R^2$ |
|---|---|---|
| L.2.3.6 | phenyl | tert-butyl |
| L.2.3.1 | tert-butyl | phenyl |

L.2.4, wherein $R^1$ and $R^2$ have the following meanings:

| No. | $R^1$ | $R^2$ |
|---|---|---|
| L.2.4.2 | tert-butyl | phenyl |
| L.2.4.3 | phenyl | phenyl |
| L.2.4.4 | tert-butyl | 3,5-dimethylphenyl |
| L.2.4.5 | tert-butyl | tert-butyl |
| L.2.4.6 | tert-butyl | cyclohexyl |

L.3.1, wherein $R^3$ and $R^4$ are methyl and $R^1$ and $R^2$ have the following meanings:

| No. | $R^1$ | $R^2$ |
|---|---|---|
| L.3.1.2 | cyclohexyl | cyclohexyl |

where in case that the chiral ligand is L.3.1.2, the transition metal of the chiral transition metal catalyst is Rh L.3.2, wherein $R^3$ and $R^4$ are methyl and $R^1$ and $R^2$ have the following meanings:

| No. | $R^1$ | $R^2$ |
|---|---|---|
| L.3.2.2 | phenyl | phenyl |
| L.3.2.1 | cyclohexyl | cyclohexyl |

where in case that the chiral ligand is L.3.2.1, the transition metal of the chiral transition metal catalyst is Ir L.3.3, wherein $R^3$ and $R^4$ are methyl and $R^1$ and $R^2$ have the following meanings:

| No. | $R^1$ | $R^2$ |
|---|---|---|
| L.3.3.1 | 3,5-dimethyl-4-methoxyphenyl | 3,5-dimethyl-4-methoxyphenyl |

L.4.1, wherein $R^1$ and $R^2$ have the following meanings:

| No. | $R^1$ | $R^2$ |
|---|---|---|
| L.4.1.4 | phenyl | Cyclohexyl |

L.4.2, wherein $R^1$ and $R^2$ have the following meanings:

| No. | $R^1$ | $R^2$ |
|---|---|---|
| L.4.2.2 | phenyl | tert-butyl |
| L.4.2.3 | tert-butyl | tert-butyl |
| L.4.2.4 | cyclohexyl | 3,5-di-(trifluoromethyl)-phenyl |

L.5.1, wherein $R^1$ and $R^2$ have the following meanings:

| No. | $R^1$ | $R^2$ |
|---|---|---|
| L.5.1.1 | 1-naphthyl | Isopropyl |

L.6.2, wherein $R^3$ and $R^4$ are methyl and $R^1$ and $R^2$ have the following meanings:

| No. | $R^1$ | $R^2$ |
|---|---|---|
| L.6.2.1 | cyclohexyl | Phenyl |
| L.6.2.2 | 3,5-dimethyl-4-methoxyphenyl | Phenyl |

L.7.2, wherein $R^1$ is phenyl

L.8.2, wherein $R^1$ and $R^2$ are phenyl

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.3 | H | $OCH_3$ | $OCH_3$ | H | isopropyl |
| L.11.1.4 | H | $OCH_3$ | $OCH_3$ | H | 3,5-diisopropyl-4-(dimethylamino)-phenyl |
| L.11.1.2 | H | $OCH_3$ | $OCH_3$ | H | 2-furyl |
| L.11.1.5 | | $—O—CH_2—O—$ | | $—O—CH_2—O—$ | xylyl |
| L.11.1.6 | | —CH═CH—CH═CH— | | —CH═CH—CH═CH— | phenyl |

where in case that the chiral ligand is L.11.1.2, the transition metal of the chiral transition metal catalyst is Ir L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L. 11.2.6 | H | $OCH_3$ | $OCH_3$ | H | 3,5-di-(tert-butyl)-4-methoxyphenyl |
| L. 11.2.3 | H | $OCH_3$ | $OCH_3$ | H | 2-furyl |

where in case that the chiral ligand is L.11.2.3, the transition metal of the chiral transition metal catalyst is Ru L.12.1, wherein $R^1$ is 3,5-dimethyl-4-methoxyphenyl L.13.2, wherein $R^{1a}$ is tert-butyl and $R^{1b}$ is methyl L.14.2, wherein $R^1$ is phenyl L.15.1, wherein $R^1$ is phenyl, $R^5$ is methyl and n is 1

L.15.2, wherein $R^1$ is phenyl, $R^5$ is methyl and n is 1.

14. The method according to claim 1, where the reducing is carried out at a hydrogen pressure of from 1 to 100 bar.

15. The method according to claim 1 where the reducing is carried out at a temperature of from −5 to 120° C.

16. The method according to claim 1, carried out in the presence of a solvent, where the solvent is selected from the group consisting of polar aprotic solvents, polar protic solvents, $C_1$-$C_4$-alkyl acetates, chlorinated alkanes, open-chained ethers, aromatic solvents, and mixtures thereof.

17. The method according to claim 16, where the solvent is selected from the group consisting of tetrahydrofuran, 2-methyltetrahydrofuran, 1,3-dioxane, 1,4-dioxane, dimethylsulfoxide, N, N-dimethylformamide, N, N-dimethylacetamide, $C_1$-$C_4$-alkanols, fluorinated $C_1$-$C_4$-alkanols, $C_1$-$C_4$-alkyl acetates, chlorinated $C_1$-$C_2$-alkanes, di-($C_1$-$C_4$-alkyl)-ethers, benzene, toluene, trifluorotoluene, the xylenes, chlorobenzene, dichlorobenzene, anisole, and mixtures of the aforementioned solvents.

18. The method according to claim 1, where the reducing is carried out in the presence of an additive selected from the group consisting of organic bases, organic or inorganic Brønsted or Lewis acids, borate esters, zinc halides, and zinc sulfonates.

19. The method according to claim 18, where the additive is used in such an amount that the molar ratio of additive and the compound (I) is in a range of from 1:100 to 10:1.

20. The method according to claim 2 wherein the group VIII metal catalyst is a group 8 or 9 catalyst.

21. The method according to claim 13, where a chiral transition metal catalyst is used which comprises a chiral ligand selected from the following ligands:

L.2.3, wherein $R^1$ and $R^2$ have the following meanings:

| No. | $R^1$ | $R^2$ |
|---|---|---|
| L.2.3.6 | phenyl | tert-butyl |

L.3.2, wherein $R^3$ and $R^4$ are methyl and $R^1$ and $R^2$ have the following meanings:

| No. | $R^1$ | $R^2$ |
|---|---|---|
| L.3.2.2 | phenyl | phenyl |

L.3.3, wherein $R^3$ and $R^4$ are methyl and $R^1$ and $R^2$ have the following meanings:

| No. | $R^1$ | $R^2$ |
|---|---|---|
| L.3.3.1 | 3,5-dimethyl-4-methoxyphenyl | 3,5-dimethyl-4-methoxyphenyl |

L.4.2, wherein $R^1$ and $R^2$ have the following meanings:

| No. | $R^1$ | $R^2$ |
|---|---|---|
| L.4.2.4 | cyclohexyl | 3,5-di-(trifluoromethyl)-phenyl |

L.5.1, wherein $R^1$ and $R^2$ have the following meanings:

| No. | $R^1$ | $R^2$ |
|---|---|---|
| L.5.1.1 | 1-naphthyl | isopropyl |

L.11.1, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L.11.1.3 | H | $OCH_3$ | $OCH_3$ | H | isopropyl |

L.11.2, wherein $R^{2a}$, $R^{2b}$, $R^{2c}$, $R^{2d}$ and $R^1$ have the following meanings:

| No. | $R^{2a}$ | $R^{2b}$ | $R^{2c}$ | $R^{2d}$ | $R^1$ |
|---|---|---|---|---|---|
| L. 11.2.3 | H | $OCH_3$ | $OCH_3$ | H | 2-furyl |

where in case that the chiral ligand is L.11.2.3, the transition metal of the chiral transition metal catalyst is Ru.

* * * * *